(12) United States Patent
Lazar et al.

(10) Patent No.: US 7,276,585 B2
(45) Date of Patent: Oct. 2, 2007

(54) IMMUNOGLOBULIN VARIANTS OUTSIDE THE FC REGION

(75) Inventors: Gregory Alan Lazar, Los Angeles, CA (US); Sher Bahadur Karki, Pomona, CA (US)

(73) Assignee: Xencor, Inc., Monrovia, CA (US)

( * ) Notice: Subject to any disclaimer, the term of this patent is extended or adjusted under 35 U.S.C. 154(b) by 0 days.

(21) Appl. No.: 11/090,981

(22) Filed: Mar. 24, 2005

(65) Prior Publication Data

US 2005/0244403 A1 Nov. 3, 2005

Related U.S. Application Data

(60) Provisional application No. 60/556,353, filed on Mar. 24, 2004, provisional application No. 60/573,302, filed on May 21, 2004, provisional application No. 60/585,328, filed on Jul. 1, 2004, provisional application No. 60/586,837, filed on Jul. 9, 2004, provisional application No. 60/599,741, filed on Aug. 6, 2004, provisional application No. 60/607,398, filed on Sep. 2, 2004, provisional application No. 60/614,944, filed on Sep. 29, 2004, provisional application No. 60/619,409, filed on Oct. 14, 2004.

(51) Int. Cl.
C07K 16/00 (2006.01)
C12P 21/08 (2006.01)

(52) U.S. Cl. .............................. 530/387.1; 530/387.3; 530/388.1

(58) Field of Classification Search ...................... None
See application file for complete search history.

(56) References Cited

U.S. PATENT DOCUMENTS

| | | | |
|---|---|---|---|
| 4,816,397 A | 3/1989 | Boss et al. | |
| 5,225,348 A | 7/1993 | Nagata et al. | |
| 5,266,491 A | 11/1993 | Nagata et al. | |
| 5,328,987 A | 7/1994 | Maliszewski | |
| 5,530,101 A * | 6/1996 | Queen et al. | 530/387.3 |
| 5,541,087 A | 7/1996 | Lo et al. | |
| 5,576,184 A | 11/1996 | Better et al. | |
| 5,623,053 A | 4/1997 | Gastinel et al. | |
| 5,624,821 A | 4/1997 | Winter et al. | |
| 5,633,162 A | 5/1997 | Keen et al. | |
| 5,648,237 A | 7/1997 | Carter | |
| 5,648,260 A | 7/1997 | Winter et al. | |
| 5,821,337 A | 10/1998 | Carter et al. | |
| 5,834,597 A | 11/1998 | Tso et al. | |
| 5,885,573 A | 3/1999 | Bluestone et al. | |
| 6,030,613 A | 2/2000 | Blumberg et al. | |
| 6,086,875 A | 7/2000 | Blumberg et al. | |
| 6,121,022 A | 9/2000 | Presta et al. | |
| 6,165,745 A | 12/2000 | Ward et al. | |
| 6,188,965 B1 | 2/2001 | Mayo et al. | |
| 6,194,551 B1 | 2/2001 | Idusogie et al. | |
| 6,242,195 B1 | 6/2001 | Idusogie et al. | |
| 6,269,312 B1 | 7/2001 | Mayo et al. | |
| 6,277,375 B1 | 8/2001 | Ward | |
| 6,331,415 B1 | 12/2001 | Cabilly et al. | |
| 6,358,733 B1 | 3/2002 | Motwani et al. | |
| 6,365,161 B1 | 4/2002 | Deo et al. | |
| 6,403,312 B1 | 6/2002 | Dahiyat et al. | |
| 6,444,789 B1 | 9/2002 | Luo | |
| 6,485,726 B1 | 11/2002 | Blumberg et al. | |
| 6,528,624 B1 | 3/2003 | Idusogie et al. | |
| 6,538,124 B1 | 3/2003 | Idusogie et al. | |
| 6,632,927 B2 | 10/2003 | Adair et al. | |
| 6,649,165 B2 | 11/2003 | Schubert | |
| 6,708,120 B1 | 3/2004 | Mayo et al. | |
| 6,719,971 B1 | 4/2004 | Carter et al. | |
| 6,737,056 B1 | 5/2004 | Presta | |
| 6,792,356 B2 | 9/2004 | Mayo et al. | |
| 6,797,492 B2 | 9/2004 | Daugherty et al. | |
| 6,801,861 B2 | 10/2004 | Mayo et al. | |
| 6,804,611 B2 | 10/2004 | Mayo et al. | |
| 6,821,505 B2 | 11/2004 | Ward | |
| 6,933,368 B2 | 8/2005 | Co et al. | |
| 6,946,292 B2 | 9/2005 | Kanda et al. | |
| 6,950,754 B2 | 9/2005 | Mayo et al. | |
| 6,982,321 B2 | 1/2006 | Winter | |
| 6,992,234 B2 | 1/2006 | Roopenian | |
| 2001/0036459 A1 | 11/2001 | Ravetch | |
| 2002/0004587 A1 | 1/2002 | Miller et al. | |
| 2002/0048772 A1 | 4/2002 | Dahiyat et al. | |
| 2002/0062010 A1 | 5/2002 | Arathoon et al. | |
| 2002/0090648 A1 | 7/2002 | Dahiyat et al. | |
| 2002/0142374 A1 | 10/2002 | Gallo et al. | |
| 2002/0155537 A1 | 10/2002 | Carter et al. | |
| 2002/0164328 A1 | 11/2002 | Shinkawa et al. | |
| 2002/0192222 A1 | 12/2002 | Blumberg et al. | |
| 2003/0012789 A1 | 1/2003 | Blumberg et al. | |
| 2003/0049654 A1 | 3/2003 | Dahiyat et al. | |
| 2003/0078385 A1 | 4/2003 | Arathoon et al. | |
| 2003/0105294 A1 | 6/2003 | Gilles et al. | |

(Continued)

FOREIGN PATENT DOCUMENTS

EP   0 268 636 B1   1/1997

(Continued)

OTHER PUBLICATIONS

Shields et al. The Journal of Biological Chemistry, 2001. 276;(9):6591-6604.*

(Continued)

*Primary Examiner*—Maher M. Haddad
*Assistant Examiner*—Chun Crowder
(74) *Attorney, Agent, or Firm*—Morgan Lewis & Bockius LLP; Robin M. Silva, Esq.

(57) ABSTRACT

The present invention relates to antibody variants outside the Fc region that alter binding affinity to one or more effector ligands, methods for their generation, and their therapeutic application.

1 Claim, 32 Drawing Sheets

U.S. PATENT DOCUMENTS

| | | |
|---|---|---|
| 2003/0108548 A1 | 6/2003 | Bluestone et al. |
| 2003/0118592 A1 | 6/2003 | Ledbetter et al. |
| 2003/0130827 A1 | 7/2003 | Bentzien et al. |
| 2003/0133939 A1 | 7/2003 | Ledbetter et al. |
| 2003/0143682 A1 | 7/2003 | Nicolaides et al. |
| 2003/0157108 A1 | 8/2003 | Presta |
| 2003/0158289 A1 | 8/2003 | Rusin et al. |
| 2003/0158389 A1 | 8/2003 | Idusogie et al. |
| 2003/0166868 A1 | 9/2003 | Presta et al. |
| 2003/0175884 A1 | 9/2003 | Umana et al. |
| 2003/0190311 A1 | 10/2003 | Dall'Acqua et al. |
| 2003/0208054 A1 | 11/2003 | Olsen et al. |
| 2003/0224397 A1 | 12/2003 | Lowman et al. |
| 2003/0229208 A1 | 12/2003 | Queen et al. |
| 2003/0232972 A1 | 12/2003 | Bowdish et al. |
| 2003/0235536 A1 | 12/2003 | Blumberg et al. |
| 2004/0002587 A1 | 1/2004 | Watkins et al. |
| 2004/0043429 A1 | 3/2004 | Dahiyat et al. |
| 2004/0043430 A1 | 3/2004 | Dahiyat et al. |
| 2004/0062763 A1 | 4/2004 | Mosser et al. |
| 2004/0185045 A1 | 9/2004 | Koenig et al. |
| 2004/0191244 A1 | 9/2004 | Presta |
| 2004/0191256 A1 | 9/2004 | Raju |
| 2004/0192897 A2 | 9/2004 | Winter |
| 2004/0228856 A1 | 11/2004 | Presta |
| 2004/0258677 A1 | 12/2004 | Waldmann et al. |
| 2004/0258682 A1 | 12/2004 | Leung et al. |
| 2004/0259150 A1 | 12/2004 | Nakamura et al. |
| 2005/0014934 A1 | 1/2005 | Hinton et al. |
| 2005/0031626 A1 | 2/2005 | Stevenson |
| 2005/0032114 A1 | 2/2005 | Hinton et al. |
| 2005/0033029 A1 | 2/2005 | Lu |
| 2005/0037000 A1 | 2/2005 | Stavenhagen et al. |
| 2005/0037002 A1 | 2/2005 | Velardi et al. |
| 2005/0038610 A1 | 2/2005 | Mayo et al. |
| 2005/0054046 A1 | 3/2005 | Presta et al. |
| 2005/0064514 A1 | 3/2005 | Stavenhagen et al. |
| 2005/0118174 A1 | 6/2005 | Presta |
| 2005/0152894 A1 | 7/2005 | Krummen et al. |
| 2005/0175614 A1 | 8/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0215767 A1 | 9/2005 | Koenig et al. |
| 2005/0226864 A1 | 10/2005 | Hinton et al. |
| 2005/0233382 A1 | 10/2005 | Presta |
| 2005/0272128 A1 | 12/2005 | Umana et al. |
| 2005/0276799 A1 | 12/2005 | Hinton et al. |
| 2006/0019316 A1 | 1/2006 | Mayo et al. |

FOREIGN PATENT DOCUMENTS

| | | |
|---|---|---|
| EP | 1 176 195 A1 | 1/2002 |
| EP | 1 229 125 A1 | 8/2002 |
| EP | 1 255 209 A2 | 11/2002 |
| EP | 0 753 065 B1 | 5/2003 |
| EP | 0 805 628 B1 | 5/2003 |
| EP | 1 323 346 A2 | 11/2003 |
| EP | 1 323 346 A3 | 11/2003 |
| EP | 0 888 125 B1 | 5/2004 |
| EP | 0 904 107 B1 | 10/2004 |
| EP | 0 383 799 B2 | 2/2005 |
| EP | 1 255 826 B1 | 9/2005 |
| WO | WO 88/07089 A1 | 9/1988 |
| WO | WO 91/06305 A1 | 5/1991 |
| WO | WO 91/19515 A1 | 12/1991 |
| WO | WO 92/04053 A1 | 3/1992 |
| WO | WO 92/16562 A1 | 10/1992 |
| WO | WO 92/22324 A1 | 12/1992 |
| WO | WO 94/29351 A2 | 12/1994 |
| WO | WO 94/29351 A3 | 12/1994 |
| WO | WO 95/05468 A1 | 2/1995 |
| WO | WO 96/22024 A1 | 7/1996 |
| WO | WO 97/28267 A1 | 8/1997 |
| WO | WO 97/34631 A1 | 9/1997 |
| WO | WO 98/02462 A1 | 1/1998 |
| WO | WO 98/05787 A1 | 2/1998 |
| WO | WO 98/23289 A1 | 6/1998 |
| WO | WO 98/47089 A1 | 11/1998 |
| WO | WO 99/04813 A1 | 2/1999 |
| WO | WO 99/51642 A1 | 10/1999 |
| WO | WO 99/54342 A1 | 10/1999 |
| WO | WO 99/58572 A1 | 11/1999 |
| WO | WO 00/09560 A2 | 2/2000 |
| WO | WO 00/09560 A3 | 2/2000 |
| WO | WO 00/23564 A2 | 4/2000 |
| WO | WO 00/23564 A3 | 4/2000 |
| WO | WO 00/24782 A2 | 5/2000 |
| WO | WO 00/24782 A3 | 5/2000 |
| WO | WO 00/42072 A2 | 7/2000 |
| WO | WO 00/42072 A3 | 7/2000 |
| WO | WO 00/61739 A1 | 10/2000 |
| WO | WO 01/29246 A1 | 4/2001 |
| WO | WO 01/38490 A2 | 5/2001 |
| WO | WO 01/57088 A1 | 8/2001 |
| WO | WO 01/59066 A2 | 8/2001 |
| WO | WO 01/59066 A3 | 8/2001 |
| WO | WO 02/30954 A1 | 4/2002 |
| WO | WO 02/31140 A1 | 4/2002 |
| WO | WO 02/44215 A2 | 6/2002 |
| WO | WO 02/060919 A2 | 8/2002 |
| WO | WO 02/060919 A3 | 8/2002 |
| WO | WO 02/061090 A3 | 8/2002 |
| WO | WO 02/061093 A1 | 8/2002 |
| WO | WO 03/014325 A2 | 2/2003 |
| WO | WO 03/014325 A3 | 2/2003 |
| WO | WO 03/016470 A2 | 2/2003 |
| WO | WO 03/025019 A | 3/2003 |
| WO | WO 03/035835 A2 | 5/2003 |
| WO | WO 03/035835 A3 | 5/2003 |
| WO | WO 03/054213 A2 | 7/2003 |
| WO | WO 03/074679 * | 9/2003 |
| WO | WO 03/089624 A2 | 10/2003 |
| WO | WO 2004/004662 A2 | 1/2004 |
| WO | WO 2004/004798 A2 | 1/2004 |
| WO | WO 2004/004798 A3 | 1/2004 |
| WO | WO 2004/016750 A3 | 2/2004 |
| WO | WO 2004/022717 A2 | 3/2004 |
| WO | WO 2004/022717 A3 | 3/2004 |
| WO | WO 2004/024871 A2 | 3/2004 |
| WO | WO 2004/024889 A2 | 3/2004 |
| WO | WO 2004/035752 A2 | 4/2004 |
| WO | WO 2004/056312 A2 | 7/2004 |
| WO | WO 2004/063351 A2 | 7/2004 |
| WO | WO 2004/063351 A3 | 7/2004 |
| WO | WO 2004/065416 A | 8/2004 |
| WO | WO 2004/074455 A2 | 9/2004 |
| WO | WO 2004/074455 A3 | 9/2004 |
| WO | WO 2004/092219 A2 | 10/2004 |
| WO | WO 2004/099249 A | 11/2004 |
| WO | WO 2004/103404 A1 | 12/2004 |
| WO | WO 2004/110472 A2 | 12/2004 |
| WO | WO 2005/000899 A2 | 1/2005 |
| WO | WO 2005/001025 A2 | 1/2005 |
| WO | WO 2005/007809 A2 | 1/2005 |
| WO | WO 2005/011376 A2 | 2/2005 |
| WO | WO 2005/012877 A2 | 2/2005 |
| WO | WO 2005/013090 A2 | 2/2005 |
| WO | WO 2005/018572 A2 | 3/2005 |
| WO | WO 2005/023866 A2 | 3/2005 |
| WO | WO 2005/027966 A2 | 3/2005 |
| WO | WO 2005/037867 A1 | 4/2005 |
| WO | WO 2005/040217 A2 | 5/2005 |
| WO | WO 2005/047327 A2 | 5/2005 |

| | | | |
|---|---|---|---|
| WO | WO 2005/060642 A2 | 7/2005 | |
| WO | WO 2005/063815 A2 | 7/2005 | |
| WO | WO 2005/070963 A1 | 8/2005 | |
| WO | WO 2005/116078 A1 | 12/2005 | |
| WO | WO 2005/123780 A2 | 12/2005 | |
| WO | WO 2006/012500 A2 | 2/2006 | |

OTHER PUBLICATIONS

Liu et al. The Journal of Immunology 1987 139;10:3521-3526.*
Morrison et al. The Journal of Immunology 1998 160:2802-2808.*
Chan et al. Molecular Immunology 2004 21:527-538.*
Algre, et al., "A non-activating "humanized" anti-CD3 monoclonal antibody retains immunosuppressive properties in vivo," *Transplantation*, 57:1537-1543 (1994).
Armour, et al., "Recombinant human IgG molecules lacking Fcgamma receptor I binding and monocyte triggering activities," *Eur J Immunol*, 29:2613-2624 (1999).
Ashkenazi, et al., "Immunoadhesins as research tools and therapeutic agents," *Curr Opin Immunol*, 9:195-200 (1997).
Chamow, et al., "Immunoadhesins: principles and applications," *Trends Biotechnol*, 14:52-60 (1996).
Davies, et al. "Expression of GnTIII in a recombinant anti-CD20 CHO production cell line: Expression of antibodies with altered glycoforms leads to an increase in ADCC through higher affinity for FC gamma RIII," *Biotechnol Bioeng*, 74:288-294 (2001).
Hutchins, et al., "Improved biodistribution, tumor targeting, and reduced immunogenicity in mice with a gamma 4 variant of Campath-1H," *PNAS USA*, 92:11980-11984 (1995).
Jefferies, et al., *Immunol Lett*, 54:101-104 (1996).
Krapp, et al., "Structural analysis of human IgG-Fc glycoforms reveals a correlation between glycosylation and structural integrity," *J Mol Biol*, 325:979-989 (2003).
Lehrnbecher, et al., "Variant Genotypes of the Low-Affinity Fcγ Receptors in Two Control Populations and a Review of Low-Affinity Fcγ Receptor Polymorphisms in Control and Disease Populations," *Blood*, 94:4220-4232 (1999).
Lund, et al., "Human Fc gamma RI and Fc gamma RII interact with distinct but overlapping sites on human IgG," *J Immunol*, 147:2657-2662 (1991).
Lund, et al., "Multiple binding sites on the CH2 domain of IgG for mouse Fc gamma R11," *Mol Immunol*, 29:53-59 (1992).
Lund, et al., "Multiple interactions of IgG with its core oligosaccharide can modulate recognition by complement and human Fc gamma receptor I and influence the synthesis of its oligosaccharide chains," *J Immunol*, 154:4963-4969 (1996).
Lund, et al., "Oligosaccharide-protein interactions in IgG can modulate recognition by Fc gamma receptors," *Faseb J*, 9:115-119 (1995).
White, et al., "Antibody-targeted immunotherapy for treatment of malignancy," *Annu Rev Med*, 52:125-145 (2001).
Aase, A. et al. "The extended hinge region of IgG3 is not required for high phogocytic capacity mediated by Fc gamma receptors, but the heavy chains must be disulfide bonded," *Eur J Immunol.*, 23(7):1546-1551 (Jul. 1993).
Abadeh, S., et al., "Remodelling the oligosaccharide of human IgG antibodies: effects on biological activities," *Biochem Soc Trans.*, 25(4):S661 (Nov. 1997).
Akewanlop, C., et al., "Phagocytosis of Breast Cancer Cells Mediated by Anti-*MUC-1* Monoclonal antibody, DF3, and Its Bispecific Antibody" *Cancer Research*, 61:4061-4065 (May 15, 2001).
Alegre, M., et al., "Effect of a Single Amino Acid Mutation on the Activating and Immunosuppressive Properties of a "Humanised" OKT3 Monoclonal Antibody," *J. Immunology*, 148:3461-3468 (Jun. 1992).
Amigorena, S., et al., "Fc receptors for IgG and antigen presentation on MHC class I and class II molecules" *Immunology*, 11:385-390 (1999).
Armour, K. L., et al., "Differential binding to human FcγRIIa and FcγRIIb receptors by human IgG wildtype and mutant antibodies," *Molecular Immunology*, 40:585-593 (2003).

Ashkenazi, A., et al., "Mapping the CD4 binding site for human immunodeficiency virus by alanine-scanning mutagenesis," *PNAS, USA*, 87:7150-7154 (Sep. 1990).
Bolland, S. "A Newly Discovered Fc Receptor tha Explains IgG-Isotype Disparities in Effector Responses," *J. Immunity*, 23:2-4 (Jul. 2005).
Boruchov, A. M., et al., "Activating and inhibitory IgG Fc receptors on human DCs mediate opposing functions" *J. Clin. Invest.* doi:10.1172/JCI24772 (Sep. 16, 2005).
Bowles, J.A., et al., "CD16 polymorphins and NK activation induced by monoclonal antibody-coated target cells," *Journal of Immunological Methods*, pp. 1-12 (2005).
Brekke, O. H., et al., "Human IgG isotype-specific amino acid residues affecting complement-mediated cell lysis and phogocytosis," *Eur J. Immunl.*, 24(10:2542-5247 (Oct. 1994).
Brekke, O. H., et al., "Human IgG3 can adopt the disulfide bond pattern characteristic for IgG1 without resembling it in complement mediated cell lysis," *Mol. Immunol.* 30(16):1419-1425 (Nov. 1993).
Bruggeman, M., et al., "Comparison of the Effector Functions of Human Immunoglobulins Using A Matched Set of Chimeric Antibodies," *J. Exp. Med.*, 166:1351-1361 (Nov. 1987).
Bruggemann, M., et al., "A matched set of rat/mouse chimeric antibodies. Identification and biological properties of rat H chain constant regions mu, gamma 1, gamma 2a, gamma 2b, gamma 2c, epsilon, and alpha," *J. Immunol.*, 142(9):3145-3150 (May 1989).
Burmeister, W. P., et al., "Crystal structure of the complex of rat neonatal Fc receptor with Fc" *Nature*, 372:379-383 (Nov. 24, 1994).
Canfield, S. M., et al., "The Binding Affinity of Human IgG for its High Affinity Fc Receptor is Determined by Multiple Amino Acids in the $C_H2$ Domain and Is Modulated by the Hinge Region," *J. Exp. Med.*, 173:1483-1491 (Jun. 1991).
Caron, P. C., et al., "Engineered Humanized Dimeric Forms of IgG Are More Effective Antibodies," *J. Exp. Med.*, 176:1191-1195 (Oct. 1992).
Caron, P. C., et al., "Murine and humanized constructs of monoclonal antibody M19 (anti-CD33) for the therapy of acute myelogenous leukemia," *Cancer*, 73(3 Supp):1049-1056 (Feb. 1994).
Carpenter, P.A., et al., "Non-Fc Receptor-Binding Humanized Anti-CD3 Antibodies Induce Apoptosis of Activated Human T Cells," *Journal of Immunology*, 165:6205-6213 (2000).
Carter, P., et al., "Humanization of an anti-p185$^{HER2}$ antibody for human cancer therapy" *PNAS*, 89:4285-4289 (May 1992).
Cartron, G., et al., "Therapeutic activity of humanized anit-Cd20 monoclonal antibody and polymorphism in IgG Fc receptor FcγRIIIa gene," *Blood*, 99(3):754-758 (Feb. 1, 2002).
Chapman, P. B., "T-Cell Chauvinists Versus Antibody Advocates-Can't We All Just Get Along?" *J. Clin. Oncology*, 22(22):4446-4448 (Nov. 15, 2004).
Chappel, M. S., et al., "Identification of a Secondary Fcγ RI Binding Site within a Genetically Engineered Human IgG Actibody," *J. Biol. Chem.*, 268(33):25124-25131 (Nov. 1993).
Chappel, M. S., et al., "Identification of the Fcγ receptor class I binding site in human IgG through the use of recombinant IgG1/IgG2 hybrid and point-mutated antibodies," *PNAS, USA*, 88:9036-9040 (Oct. 1991).
Chintalacharuvu, K. R., et al., "Hybrid IgA2/IgG1 Antibodies with Tailor-Made Effector Functions," *Clinical Immunology*, 101(1):21-31- (Oct. 2001).
Clynes, R. A., et al., "Inhibitory Fc receptors modulate in vivo cytoxicity against tumor targets," *Nature Medicine*, 6(4):443-446 (Apr. 2000).
Clynes, R. et al., "Modulation of Immune complex-induced inflammation In Vivo by the Coordinate Expression of Activation and Inhibitory Fc Receptors," *J. Exp. Med.*, 189(1):179-185 (Jan. 4, 1999).
Clynes, R., "Immune complexes as therapy for autoimmunity" *J. Clin. Invest.*, 115:25-27 (2005).
Clynes, R., et al., "Fc receptors are required in passive and active immunity to melanoma," *PNAS USA*, 95:652-656 (Jan. 1998).
Cohen-Sodal, J. FG., et al., "Review: Fcγ receptors" *Immunology Letts*, 92:199-205 (2004).

Cole, M. S., et al., "Human IgG2 variants of chimeric anti-CD3 are nonmitogenic to T cells," *J. Immunol.*, 159(7):3613-3621 (Oct. 1, 1997).

Coloma, M. J., et al., "The hinge as a spacer contributes to convalent assembly and is required for function of IgG," *J. Immunol.*, 158(2):733-740 (Jan. 15, 1997).

D'Uscio, C. H., et al., "Cellular cytotoxicity mediated by isotype-switch variants of a monoclonal antibody to human neuroblastoma," *Br. J. Cancer*, 64(3):445-450 (Sep. 1991).

Da Silveira, S. A., et al., "Complement Activation Selectively Potentiates the Pathogenicity of the IgG2 b and IgG3 Isotypes of a High Affinity Anti-Erythrocyte Autoantibody," *J. Exp. Med.*, 195(6):665-672 (Mar. 18, 2002).

Dall'Acqua, D. F., et al., "Increasing the Affinity of a Human IgG1 for the Neonatal Fc Receptor: Biological Consequences," *Journal of Immunology*, 169:5171-5180 (2002).

Davis, R. S., et al., "Fc receptor homologs: newest members of a remarkably diverse Fc receptor gene family," *Imm. Revs*, 190:123-136 (2002).

Davis, R. S., et al., "Identification of a family of Fc receptor homologs with preferential B cell expression," *PNAS, USA*, 98(17):9772-9777 (Aug. 2001).

Delano, W. L., et al., "Convergent Solutions to Binding at a Protein-Protein Interface" *Science*, 287:1279-1283 (Feb. 18, 2000).

Dhodapkar, K.M., et al., "Antitumor Monoclonal Antibodies Enhance Cross-Presentation of Cellular Antigens and the Generation of Myeloma-specific Killer T-Cells by Dendritic Cells" *J. Exp Med.*, 195(1):125-133 (Jan. 7, 2002).

Dhodapkar, K.M., et al., "Recruiting dendritic cells to improve antibody therapy of cancer" *PNAS*, 102(18):6243-6244 (May 3, 2005).

Dhodapkar, K.M., et al., "Selective blockade of inhibitory Fcγ receptor enables human dendritic cell maturation with IL-12p70 production and immunity to antibody-coated tumor cells" *PNAS*, 102(8):2910-2915 (Feb. 22, 2005).

Dhodapkar, M. V., et al., "T cells from the tumor microenvironment of patients with progressive myeloma can generate strong, tumor-specific cytolytic responses to autologous, tumor-loaded dendritic cells" *PNAS*, 99(20):13009-13013 (Oct. 1, 2002).

Duncan, A. R., et al., "Localization of the binding site for the human high-affinity Fc receptor on IgG," *Nature*, 332:563-564 (Apr. 7, 1988).

Duncan, A. R., et al., "The binding site for C1q on IgG," *Nature* 332:738-740 (Apr. 21, 1988).

Edelman, G. M., et al., "The Covalent Structure of an Entire γG Immunoglobulin Molecule," *PNAS*, 63:78-85 (1969).

Ehrhhardt, G. R. A., et al., "The inhibitory potential of Fc receptor homolog 4 on memory B cells," *PNAS, USA*, 100(23):13489-13494 (Nov. 2003).

Ellison, J. W., et al., "The nucleotide sequence of a human immunoglobulin C$\gamma_1$ gene" *Nucleic Acids Research*, 10(13):4071-4079(1982).

Ernst, L. K., et al., "Molecular characterization of six variant Fcγ receptor class I (CD64) transcripts," *Molecular Immunology*, 35:943-954 (1998).

Facchetti, F., et al., "An unusual Fc receptor-related protein expressed in human centroblasts," *PNAS, USA*, 99(6):3776-3781 (Mar. 19, 2002).

Gaboriaud, C., et al., "The Crystal Structure of the Globular Head of Complement Protein C1q Provides a Basis for Its Versatile Recognition Properties," *J. Biol. Chem.*, 278(47):46974-46982 (2003).

Garman, S. C., et al., "Structure of the Fc fragment of human IgG bound to its high-affinity receptor FcεRIα," *Nature*, 406:259-266 (2000).

Getahun, A., et al., "IgG2a-Mediated Enhancement of Antibody and T Cell Responses and Its Relation to Inhibitory and Activating Fcγ Receptors," *J. of Immunology*, 172:5269-5276 (2004).

Ghazizadeh, S., et al., "Physical and Functional Association of Src-related Protein Tyrosine Kinases with FcRII in Monocytic THP-1 Cells," *J. Biol. Chem.*, 269(12):8878-8884 (Mar. 25, 1994).

Ghetie, V., et al., "FcRn: the MHC class I-related receptor that is more than an IgG transporter" *Immunology Today*, 18(12):592-598 (Dec. 1997).

Ghetie, V., et al., "Increasing the serum persistence of an IgG fragment random mutagenesis," *Nat. Biotechol.*, 15(7):637-640 (Jul. 1997).

Ghetie, V., et al., "Multiple Roles for the Major Histocompatibility Complex Class I-Related Receptor FcRn," *Annu. Rev. Immunol.* 18:739-766 (2000).

Gonzales, N. R., et al., "SDR grafting of a murine antibody using multiple human germline templates to minimize its immunogenicity," *Molecular Immunology*, 41:863-872 (2004).

Greenwood, J. "Molecular Recognition in the Structure and Assembly of Filamentous Bacteriphages," Dissertation submitted to the University of Cambridge (Oct. 1989).

Greenwood, J., et al., "Structural motifs involved in human IgG antibody effector functions," *Eur. J. Immunol.*, 23(5):1098-1104 (May 1993).

Greenwood, J., et al., "Dual Importance of Positive Charge in the C-Terminal Region of Filamentous Bacteriophage Coat Protein for Membrane Insertion and DNA-Protein Interaction in Virus Assembly," *Virology*, 171:444-452 (1989).

Greenwood, J., et al., "Effector functions of matched sets of recombinant human IgG subclass antibodies," Dissertation submitted to Cambridge University, Cambridge, UK (Feb. 1993).

Greenwood, J., et al., "Engineering multiple-domain forms of the therapeutic antibody CAMPATH-1H: effects on complement lysis," *Ther. Immunol.*, 1(5):247-255 (Oct. 1994).

Groh, V., et al., "Efficient cross-priming of tumor antigen specific T cells by dendritic cells sensitized with diverse anti-MICA opsonized tumor cells" *PNAS*, 102(18):6461-6466 (May 3, 2005).

Harrison, P. T., et al., "Domain swap chimeras to study the binding of IgG by Fc gamm RI, the high affinity receptor for IgG," *Biochem Soc Trans.*, 24(1):144S (Feb. 1996).

Hazenbos, W.L., et al., "Murine IgG1 complexes Trigger Immune Effector Functions Predominately via Fcγ RIII (CD16)," *J. of Immunology*, 161:3026-3032 (1998).

Henry, A. J., et al., "Participation of the N-Terminal of Cε3 in the Binding of Human IgE to Its High-Affinity Receptor FcεRI," *Biochemistry*, 36:15568-15578 (1997).

Hezareh, M., et al., "Effector Function Activities of a Panel of Mutants of a Broadly Neutralizing Antibody against Human Immunodeficiency Virus Type I," *Journal of Virology*, 75(24):12161-12168 (2001).

Hinton, P. R., et al., "Engineered human IgG Antibodies with Longer Serum Half-Lives in Primates," *J. Biol. Chem.*, 279(8):6213-6216 (Feb. 20, 2004).

Idusogie, E. E., et al., "Engineered Antibodies with increased Activity to Recruit Complement," *J. of Immunology*, 166:2571-2575 (2001).

Idusogie, E.E., et al., "Mapping of the C1q Binding Site of Rituxan, a Chimeric Antibody with a Human IgG1 Fc," *J. of Immunology*, 164:4178-4184 (2000).

Isaacs, J. D., "Improving Serotherapy with Monoclonal Antibodies" dissertation submitted to the University of Cambridge (Mar. 1991).

Isaacs, J. D., et al., "From bench to bedside: discovering rules for antibody design, and improving serotherapy with monoclonal antibodies," *Rheumatology*, 40:724-738 (2001).

Issacs, J. D., et al., "Therapy with Monoclonal Antibodies, II. The contribution of Fcγ Receptor binding and the Influenece of $C_H1$ and $C_H3$ Domains on In Vivo Effector Function," *J. of Immunology*, 161:3862-3869 (1998).

Isaacs, J. D., et al., "Therapy with Monoclonal Antibodies: an in vivo model for the assessment of therapeutic potential," *J. Immunol.*, 148(10):3062-3071 (May 15, 1992).

Jefferis, R. et al., "Recognition sites on human IgG for Fc gamma receptors: the role of glycosylatin," *Immunol Letters*, 44(2-3):111-117 (Jan. 1995).

Jefferis, R., et al., "Interaction sites of human IgG-Fc for FcγR: current models," *Immunology Letts.*, 82:57-65 (2002).

Jefferis, R., et al., "Modulation of FcγR and human complement activation by IgG3-core oligosaccharide interactions," *Immunology Letters*, 54:101-104 (1996) and errata at *Immunology Letters*, 58:67 (1997).

Jefferis, R., et al., "Molecular definition of interaction sites on human IgG for Fc receptors (huFc gamma R)," *Mol Immunol.*, 27(12):1237-1240 (Dec. 1990).

Jendeberg, L., et al., "Engineering of $Fc_1$ and $Fc_3$ from human immunoglobulin G to analyse subclass specificity for staphylococcal protein A," *Journal of Immunological Methods*, 201:25-34 (1997).

Junghans, R. P., et al., "The protection receptor IgG catabolism is the $\beta_2$-microglobulin-containing neonatal intestinal transport receptor," *PNAS*, 93:5512-5516 (May 1996).

Kalergis, A.M., et al., "Inducing Tumor Immunity through the Selective Engagement of Activating Fcγ Receptors on Dendritic Cells" *J. Exp. Med.* 195(12):1653-1659 (Jun. 17, 2002).

Kan, K. S., et al., "Thioether-Bonded Constructs of Fabγ and Fcγ Modules Utilizing Differential Reduction of Interchain Disulfide Bonds," *Journal of Immunology*, 166:1320-1326 (2001).

Karassa, F. B., et al., "The role of FcγRIIA and IIIA polymorphisms in autoimmune diseases" *Biomedicine & Pharmacotherapy*, 58:286-291 (2004).

Kim, J. et al., "Mapping the site on human IgG for binding of the MHC class I-related receptor, FcRn" *Eur. J. Immunol.*, 29:2819-2825 (1999).

Kim, J. K., et al., "Localization of the site of the murine IgG1 molecule that is involved in binding to the murine intestinal Fc receptor," *Eur J Immunol.*, 24(10:2429-2439 (Oct. 1994).

Kim, J.K., et al., "Identifying amino acid residues that influence plasma clearance of murine IgG1 fragments by site-directed mutagenesis," *Eur J. Immunol.*, 24(3):542-548 (Mar. 1994).

Kim, T. D., et al., "Analysis of FcγRIII and IgG Fc Polymorphism Reveals Functional and Evolutionary Implications of Protein-Protein Interaction," *J. Mol. Evol.*, 53:1-9 (2001).

Kurucz, I., et al., "Bacterially expressed human FcγRIIb is soluble and functionally active after in vitro refolding" *Immunology Letts.*, 75:33-40 (2000).

Lund, J., et al., "A protein structural change in aglycosylated IgG3 correlates with loss of huFc gamma R1 and huFc gamma R111 binding and/or activation," *Mol. Immunol.*, 27(11):1145-1153 (Nov. 1990).

Lund, J., et al., "Control of IgG/Fc glycosylation: a comparison of oligosaccharides from chimeric human/mouse and mouse subclass immunoglobulin Gs," *Mol Immunol.*, 30(8):741-748 (Jun. 1993).

Maenaka, K., et al., "The Human Low Affinity Fcγ Receptors IIa, IIb and III Bind IgG with Fast Kinetics and Distinct Thermodynamic Properties" *J. Biol. Chem.* 276(48):44898-44904 (2001).

Martin, W. L., et al., "Characterization of the 2:1 Complex between the Class I MHC-Related Fc Receptor and Its Fc Ligand in Solution," *Biochemistry*, 38:12639-12647 (1999).

Martin, W. L., et al., "Crystal Structures at 2.8 Å of an FcRn/Heterodimeric Fc Complex: Mechanism of pH-Dependent Binding" *Molecular Cell*, 7:867-877 (Apr. 2000).

Masztalerz, A., et al., "Mechanisms of macrophage cytotoxicity in IL-2 and IL-12 mediated tumor regression," *Cancer Immunol Immunother*, 52:235-242 (2003).

Maxwell, K.F., et al., "Crystal structure of the human leukocyte Fc receptor, FcRIIa." *Nature Structural Biology*, 6(5):437-442 (May 1999).

Mayfield, S. P., et al., "Expression and assembly of a fully active antibody algae," *PNAS*, 100(2):438-442 (Jan. 21, 2003).

Mechetina, L. V., et al., "Identification of CD16-2, a novel mouse receptor homologous to CD16/FcγRIII," *Immunogenetics*, 4:463-468 (2002).

Merchant, A. M. et al., "An efficient route to human bispecific IgG," *Nat Biotechnol.*, 16(7):677-681 (1998).

Metes, D., et al., "Expression of Functional CD32 Molecules on Human NK Cells Is Determined by and Allelic Polymorphism of the Fcγ RIIC Gene," *Blood*, 91(7):2369-2380 (Apr. 1, 1998).

Michaelson, T. E., et al., "Antibody Dependent Cell-Mediated Cytotoxicity Induced by Chimeric Mouse-Human IgG Subclass and IgG3 Antibodies with Altered Hinge Region," *Molecular Immunology*, 29(3):319-326 (1992).

Michaelson, T. E., et al., "One disulfide bond in front of the second heavy chain constant region is necessary and sufficient for effector functions of human IgG3 without a genetic hinge," *PNAS*, 91:9243-9247 (Sep. 1994).

Michaelson, T. E., et al., "Primary Structure of the 'Hinge' Region of Human IgG3," *J Biol Chem.*, 252(3):883-889 (Feb. 1977).

Miller, I., et al., "ITRAs: a new family of immunoglobulinlike receptors differentially expressed in B cells," *Blood*, 99(8):2662-2669 (Apr. 15, 2002).

Mimura, Y., et al., "Role of Oligosaccharide Residues of IgG1-Fc in Fcγ RIIb Binding," *J. Biol. Chem.*, 276(49):45539-45547 (Dec. 7, 2001).

Morgan, A., et al., "The N-terminal end of the CH2 domain of chimeric human IgG1 anti-HLA-DR is necessary for C1q, Fc gamma R1 and Fc gamma RIII binding," *Immunology*, 86(2):319-324 (Oct. 1995).

Nakamura, K., et al., "Dissection and optimization of immune effector functions of humanized anti-ganglioside GM2 monoclonal antibody," *Molecular Immunology*, 37:1035-1046 (2000).

Neidhardt-Berard, E., et al., "Dendritic cells loaded with killed breast cells induce differentiation of tumor-specific cytoxic T lymphocytes" *Breast Cancer Res.*, 6R322-R328 (Apr. 30, 2004).

Nimmerjahn, F., et al., "Divergent Immunoglobulin-G Subclass Activity Through Selective Fc Receptor Binding" *Science*, 310:1510 (2005).

Nimmerjahn, F., et al., "Fcγ RIV: A Novel FcR with Distinct IgG Subclass Specificity," *Immunity*, 23:41-51 (Jul. 2005).

Nimmerjahn, F., et al., "Supporting Online Material for: Divergent Immunoglobulin G Subclass Activity Through Selective Fc Receptor Binding" *Science*, 310:1510 (2005).

Niwa, R., et al., "Defucosylated Chimeric Anti-CC Chemokine Receptor 4 IgG1 with Enhanced Antibody-Dependnent Cellular cytotoxicity Shows Potent Therapeutic Activity to T-Cell Leukemia and Lymphoma," *Cancer Research*, 64:2127-2133 (Mar. 15, 2004).

Norderhaug, L., et al., "Chimeric mouse human IgG3 antibodies with an IgG4-like hinge region induce complement-mediated lysis more efficiently than IgG3 with normal hinge," *Eur J immunol.*, 21(10):2379-2384 (Oct. 1991).

O'Connor, S. J., et al., "Humanization of an antibody against human protein C and calcium-dependence involving framework residues," *Protein Engineering*, 11(4):321-328 (1998).

Ober, R. J. , et al., "Differences in promiscuity for antibody-FcRn interactions across species: implications for therapeutic antibodies," *International Immunology*, 13(12):1551-1559 (2001).

Ober, R. J., et al., "Exocytosis of IgG as mediated by the receptor, FcRn: An analysis at the single-molecule level" *PNAS*, 101(30):11076-11081 (Jul. 27, 2004).

Okazaki, A., et al., "Fucose Depletion from Human IgG1 Oligosaccharide Enhances Binding Enthalpy and Association Rate Between IgG1 and Fcγ RIIIa," *J. Mol. Biol.*, 336:1239-1249 (2004).

Parren, P. W., et al., "Characterization of IgG FcR-mediated proliferation of human T-cells induced by mouse and human anti-CD3 monoclonal antibodies. Identification of a functional polymorphism to human IgG2 anti-CD3," *J. Immunol.*, 148(3):695-701 (Feb. 1992).

Parren, P. W., et al., "On the interaction of IgG subclasses with the low affinity Fc gamma RIIa (CD32) on human monocytes, neutrophils, and platelets. Analysis of a functional polymorphism to human IgG2," *J Clin Invest.*, 90(4):1537-1546 (Oct. 1992).

Pearce, K. H., et al., "Mutational Analysis of Thrombopoietin for Identification of Receptor and Neutralizing Antibody Sites," *J. Biol. Chem.*, 272(33):20595-20602 (1997).

Preithner, S., et al., "High concentrations of therapeutic Igg1 antibodies are needed to compensate for inhibition of antibody-dependent cellular cytotoxicity by excess endogenous immunoglobulin G," *Molecular Immunology*, (2005).

Presta, L.G., et al., "Engineering therapeutic antibodies for improved function," *Biochemical Society Transactions*, 30(part 4):487-490 (2002).

Radaev, S., et al., "Recognition of IgG by Fcγ Receptor," *J. Biol. Chem.*, 276(19):16478-16483 (May 11, 2001).

Radaev, S., et al., "Review: Recognition of immunoglobulins by Fcγ recptors," *Molecular Immunology*, 38:1073-1083 (2001).

Radaev, S., et al., "The Structure of Human Type III Fcγ Receptor in Complex with Fc," *J. Biol. Chem.*, 276(19):16469-16477 (May 11, 2001).

Rafiq, K., et al., "Immune complex-mediated antigen presentation induces tumor immunity" *J. Clin. Invest.*, 110:71-79 (2002).

Raghavan, M., et al., "Fc Receptors and their Interactions with Immunoglobulins" *Annu. Rev. Cell Div. Biol.*, 12:181-220 (1996).

Ravetch, J. V., et al., "IgG Fc Receptors" *Annu. Rev. Immunol.*, 19:275-290 (2001).

Ravetch, J. V., et al., "Immune Inhibitory Receptors," *Science*, 290:84-89 (Oct. 6, 2000).

Ravetch, J.V., et al., "Fc Receptors," *Annu. Rev. Immunol.*, 9:457-492 (1991).

Reddy, P. R., et al., "Elimination of Fc Receptor-Dependent Effector Functions of a Modified IgG4 Monoclonal Antibody to Human CD4" *J. Immunol.*, 164:1925-1933 (2000).

Redpath, S., et al., "The Influence of the Hinge Region Length in Binding of Human IgGto Human Fcγ Receptors," *Human Immunology*, 59:720-727 (1998).

Rozsnyay, Z., et al., "Distinctive role of IgG1 and IgG3 isotypes in FcR-mediated functions," *Immunology*, 66(4):491-498 (Apr. 1989).

Sandlie, A.A., "The extended hinge region of IgG3 is not required for high phogocytic capacity mediated by Fc gamma receptors, but the heavy chains must be disulfide bonded," *Eur J. Immunol.*, 23(7):1546-1551 (Jul. 1993).

Sarmay, G., et al., "Mapping and Comparison of the Interaction Sites on The Fc Region of IgG Responsible for Triggering Antibody Dependent Cellular Cytotoxicity (ADCC) Through Different Types of Human FCγ Receptor," *Molecular Immunology*, 29(5):633-639 (1992).

Sautes-Fridman, C., et al., "Fc Gamma Receptors: A Magic Link with the Outside World," *ASHI Quarterly*, 148-151, (Fourth Quarter 2003).

Sensel, M. G., et al., "Amino Acid Differences in the N-Terminus of $C_H2$ Influence The Relative abilities of IgG2 and IgG3 to Activate Complement" *Mol. Immunol.*, 34(14):1019-1029 (1997).

Shields, R. L., et al., "High Resolution Mapping of the Binding Site on Human IgG1 for Fcγ RI, Fcγ RII, Fcγ RIII, and FcRn and Design of IgG1 Varients with Improved Binding to the Fcγ R" *J. Biol. Chem.*, 276(9):6591-6604 (2001).

Shields, R. L., et al., "Lack of Fucose on human IgG1 N-Linked Oligodaccharide Improves Binding to Human Fcγ RIII and Antibody-dependent Cellular Toxicity" *J. Biol. Chem.*, 277(30)26733-26740 (2002).

Shinkawa, T., et al., "The Absense of Fucose but Not the Presence of Galactose or Bisecting *N*-Acetylglucosamine of Human IgG1 complex-type Oligosaccharides Shows the Critical Role of Enhancing Antibody-dependent Cellular Cytotoxicity" *J. Biol. Chem.*, 278(5):3466-3473 (2003).

Shopes, B., "A genetically engineered human IgG mutant with enhanced cytolytic activity," *J Immunol.*, 148(9):2918-2922 (May 1992).

Shopes, B., et al., "Recombinant human IgG1-murine IgE chimeric Ig. Construction, expression, and binding to human Fc gamma receptors," *J. Immunol.*, 145(11):3842-3848 (Dec. 1, 1990).

Simmons, L. C., et al., "Expression of full-length immunoglobulins in *Escherichia coli*; rapid and efficient production of a glycosylated antibodies" *J. Immunol. Methods*, 263:133-147 (2002).

Smith, I. F. R., et al., "Addition of a μ-Tailpiece to IgG Results in Polymeric Antibodies with Enhanced Effector Functions Including Complement-Mediated Cytolysis by IgG4," *J. Immunology*, pp. 2226-2236 (1995).

Smith, K.G., et al., "T cell activation by anti-T3 antibodies: comparison of IgG1 and IgG2b switch variants and direct evidence for accessory function of macrophage Fc receptors," *Eur J Immunol.*, 16(5):478-486 (May 1986).

Sonderman, P. et al., "Crystal structure of the soluble form of the human FCγ-receptor IIb: a new member of the immunoglobulin superfamily at 1.7Å resolution" *EMBO Journal*, 18(5):1095-1103 (1999).

Sonderman, P., et al., "Human Fcγ Receptor IIb Expressed in *Escherichia coli* Reveals IgG Binding Capability" *Biol. Chem.* 380:717-721 (Jun. 1999).

Sonderman, P., et al., "Molecular Basis for Immune Complex Recognition: A comparison of Fc-Receptor Structures" *J. Mol. Biol.*, 309:737-749 (2001).

Sonderman, P., et al., "The 3.2—Å crystal structure of the human IgG1 Fc fragment -FcγRIII complex" *Nature*, 406:267-273 (Jul. 20, 2000).

Sorenson, V., et al., "Effect of the IgM and IgA secretory tailpieces on polymerization and secretion of IgM and IgG," *J Immunol.*, 156(8):2858-2865 (Apr. 1996).

Steplewski, Z., et al., "Biological activity of human-mouse IgG1, IgG2, IgG3, and IgG4 chimeric monoclonal antibodies with antitumor specificity," *PNAS USA*, 85:4852-4856 (Jul. 1988).

Stevenson, G. T., et al., "Preparation of Fcγ for addition to sulfhydryl-expressing ligands with minimal disturbance of the hinge," *J. of Immunological Methods*, 231:169-175 (1999).

Tao, M., et al., "Structural Features of Human immunoglobulin G that Determine Isotype-specific Differences in Complement Activation," *J. Exp. Med.* 178:661-667 (Aug. 1993).

Tao, M., et al., "The Differential Ability of Human IgG1 and IgG4 to Activate Complement Is Determined by the COOH-terminal Sequence of the $C_H2$ domain" *J. Exp. Med*, 173:1025-1028 (Apr. 1991).

Thommesen, J. E., et al., "Lysine 322 in the human IgG3 $C_H2$ domain is crucial for antibody dependent complement activation" *Molecular Immunology*, 37:995-1014 (2000).

Tuijnman W. B., et al., "A flow cytometric rosetting assay for the analysis of IgG-Fc receptor interactions," *J Immunol Methods*, 127(2):207-214 (Mar. 1990).

Uchide, J. et al., "The innate Mononuclear Phagocyte Network Depletes B Lymphocytes through Fc Receptor-dependent mechanisms during Anti-CD20 Antibody Immunotherapy" *J. Exp. Med.* 199(12):1659-1669 (Jun. 21, 2004).

Umana, P., et al., "Engineered glycoforms of an antineuroblastoma IgG1 with optimized antibody-dependent cellular cytotoxic activity," *Nature Biotechnology*, 17:176-180 (1999).

Van Royen-Kerkhof, A, et al., "Flow cytometric determination of Fcγ RIIa (CD32) polymorphism," *J. Immunol. Methods*, 294:135-144 (2004).

Van Schie, R.C.A.A., et al., "Evaluation of Human Fcγ RIIA (CD32) and Fcγ RIIIB (CD16) Polymorphisms in Caucasians and African-Americans Using Salivary DNA," *Clinical and Diagnostic Laboratory Immunology*, 7(4):676-681 (Jul. 2000).

Van Sorge, N. M., et al., "Fcγ R polymorphisms: Implications for function, disease and susceptibility and immunotherapy" *Tissue Antigens*, 63:189-202 (2003).

Vidarte, L., et al., "Serine 132 Is the C3 Covalent Attachment Point of the CH1 domain of Human IgG1" *J. Biol. Chem.*, 276(41):38217-38223 (2001).

Ward, E. S., et al., "Evidence to support the cellular mechanism involved in serum IgG homeostatis in humans" *International Immunology*, 15(2):187-195 (2003).

Warmerdam, P. A., et al., "Interaction of a human Fc gamma RIIb1 (CD32) isoform with murine and human IgG subclasses," *Int Immunol.*, 5(3):239-247 (Mar. 1993).

Wawryznczak, E. J., et al., "Recombinant mouse monoclonal antibodies with single amino acid substitutions affecting Clq and high affinity Fc receptor binding have identical serum half-lives in the BALB/c mouse," *Mol. Immunol.*, 29(2):221-227 (Feb. 1992).

Weiner, L. M., et al., "Tunable antibodies," *Nature Biotechnology*, 23(5):556-557 (May 2005).

Weng, W., et al., "Clinical Outcome of Lymphoma Patients After Idiotype Vaccination Is Correlated With Humoral Immune Response and Immunoglobulin G Fc Receptor Genotype," *J. Clin Oncol.*, 22(23):1-8 (2004).

Weng, W., et al., "Two Immunoglobulin G Fragment C Receptor Polymorphisms Independently Predict Response to Rituximab in Patients With Follicular Lymphoma," *Journal of Clinical Oncology*, 21(21):3940-3947 (Nov. 1, 2003).

West, A. P., et al., "Crystal Structure and immunoglobulin G Binding Properties of the Human Major Histocompatibility Complex-Related Fc Receptor" *Biochemistry*, 39:9698-9708 (2000).

Wing, M. G., et al., "Mechanism of First-Dose Cytokine-Release Syndrome of CAMPATH 1-H:Involvement of CD16 (FcγRIII) and CD11a/CD18 (LFA-1)on NK Cells," *J. Clin. Invest.*, 98(12):2819-2826 (Dec. 1996).

Wolff, E.A., et al., "Monoclonal antibody homodimers: enhanced antitumor activity in nude mice," *Cancer Res.*, 53(11):2560-2565 (Jun. 1, 1993).

Wright, A., et al., "Effect of C2-Associated carbohydrate Structure on Ig Effector Function: Studies with Chimeric Mouse-Human IgG1 Antibodies in Glycosylation Mutants of Chinese Hamster Ovary Cells" *J. of Immunology*, 160:3393-3402 (1998).

Wright, A., et al., "In vivo trafficking and catabolism of IgG1 antibodies with Fc associated carbohydrates of differing structures," *Glycobiology*, 10(12):1347-1355 (2000).

Xu, D., et al., "In Vitro Characterization of Five Humanized OKT3 Effector Function Varient Antibodies," *Cellular Immunology*, 200:16-26 (2000).

Xu, M., et al., "Molecular Cloning and Characterization of SPAP1, an Inhibitory Receptor," *Biochemical and Biophysical Research Communications*, 280:768-775 (2001).

Xu, Y., et al., "Residue at Position 331 in the IgG1 and IgG4 $C_H 2$ Domains Contributes to Their Differential Ability to Bind and Activate Complement" *J. Biol. Chem.* 269(5):3469-3474 (1994).

Zelaschi, D., et al., "Human immunoglobulin allotypes: previously unrecognized determinants and alleles defined with monoclonal antibodies," *PNAS, USA*, 80:3762-3766 (Jun. 1983).

Zhou, H., et al., "DNA-based vaccines activate innate and adaptive antitumor immunity by engaging the NKG2D receptor" *PNAS*, 102(31):10846-10851 (Aug. 2, 2005).

Zhou, J., et al., "Generation of Mutated Variants of the Human Form of the MHC Class I-related Receptor, FcRn, with Increased Affinity for Mouse Immunoglobulin G," *J. Mol. Biol.*, 332(4):901-13 (Sep. 2003).

Zhu, D., et al., "A novel human immunoglobulin Fc gamma Fc epsilon bifunctional fusion protein inhibits Fc epsilon RI-mediated degranulation," *Nat Med.*, 8(5):518-521 (May 2002).

Andreakos, E., et al., "Monoclonal antibodies in immune and inflammatory diseases," *Curr. Opin. Biotech.*, 13:615-620 (2002).

Carter, P., "Improving The Efficacy of Antibody-Based Cancer Therapies," *Nature Reviews*, 1:118-129 (2001).

Chadd, H., et al., "Therapeutic antibody expression technolog," *Curr. Opin. Biotech.*, 12:188-194 (2001).

Clark, M. "Antibody humanization: a case of the 'Emperor's new clothes?'" *Immunol. Today*, 21(8):397-402 (2000).

Cragg, M., et al., "Signaling antibodies in cancer therapy," *Curr. Opin. Immunol.*, 11:541-547 (1999).

Dall'Acqua, W., et al., "Antibody Engineering," *Curr. Opin Structural Biol.*, 8:443-450 (1998).

Glennie, M., et al., "Clinical trials of antibody therapy," *Immun. Today*, 21(8):403-410 (2000).

Glennie, M., et al., "Renaissance of cancer therapeutic antibodies," *Drug Discovery Today*, 8(11):503-510 (2003).

Hayhurst, A., et al., "High-throughput antibody isolation," *Curr. Opin. Chem. Biol.*, 5:683-689 (2001).

Hogarth, P., "Fc receptors are major mediators of antibody based inflammation in autoimmunity," *Curr. Opin. Immun.*, 14:7998-802 (2002).

Holliger, P., et al., "Antibodies come back from the brink," *Nature Biotechnology*, 16:1015-1016 (1998).

Hudson, P., "Recombinant antibody constructs in cancer therapy," *Curr. Opin. Immunology*, 11:548-557 (1999).

Hudson, P., "Recombinant antibody fragments," *Curr. Opin in Biotechnology*, 9:395-402 (1998).

Johnson, G., et al., "Kabat Database and its applications: 30 years after the first variability plot," *Nucleic Acids Research*, 28(1):214-218 (2000).

Johnson, G., et al., "Kabat Database and its applications: future directions," *Nucleic Acids Research*, 29(1):205-206 (2001).

Maynard, J., et al., "Antibody Engineering," *Annu. Rev. Biomed. Eng.*, 2:339-376 (2000).

Morea, V., et al., "Antibody Modeling: Implications for Engineering and Design," *Methods*, 20:267-279 (2000).

Penichet, M., et al., "Antibody-cytokine fusion proteins for the therapy of cancer," *Journal of Immunological Methods*, 248:91-1010 (2001).

Reichert, J., "Monoclonal antibodies in the clinic," *Nature Biotechnology*, 19:819-822 (2001).

Thrush, G., et al., "Immunotoxins: An Update," *Ann. Rev. Immunol.*, 14:49-71 (1996).

Torphy, T., et al., "Pharmaceutical biotechnology Monoclonal antibodies: boundless potential, daunting challenges—Editorial Overview," *Curr. Opin. Biotechnol.*, 13:589-591 (2002).

Trail, P., et al., "Monoclonal antibody drug conjugates in the treatment of cancer" *Curr. Opin. Immunol.*, 11:584-588 (1999).

Trikha, M., "Monoclonal antibodies as therapeutics in oncology," *Curr. Opin. Biotech.*, 13:609-614 (2002).

Van Dijk, M., et al., "Human antibodies as next generation therapeutics," *Curr Opin. Chem. Biol.*, 5:368-374 (2001).

Van Sorge, N., et al., "Fcγ R polymorphisms: Implications for function, disease susceptibility and immunotherapy," *Tissue Antigens*, 61:189-202 (2003).

Vasserot, A., et al., "Optimization of protein therapeutics by directed evolution," *Drug Discovery Today*, 8(3):118-126 (2003).

Waldmann, T., et al., "Emerging Therapies: Spectrum of Application of Monoclonal Antibody Therapy," *Hemotology*, 394-408 (2000).

Kabat E.A. et al. "Sequences of proteins of immunological interest" (1991) *U.S. Dept. of Health and Human Services, Public Health Service* pp. 664,665,103,113,118,128,317,324.

Bruggeman et al. "Regulation of the flavin redox potential by flavin-binding antibodies" *European Journal of Biochemistry*, vol. 249, No. 2, 1997, pp. 393-400.

\* cited by examiner

Figure 3a. Vk

| | F | R | 1 | | | | | | | | | | | | | | | | | |
|---|---|---|---|---|---|---|---|---|---|---|---|---|---|---|---|---|---|---|---|---|
| Kabat | 1 | 2 | 3 | 4 | 5 | 6 | 7 | 8 | 9 | 10 | 11 | 12 | 13 | 14 | 15 | 16 | 17 | 18 | 19 | 20 |
| Chothia | 1 | 2 | 3 | 4 | 5 | 6 | 7 | 8 | 9 | 10 | 11 | 12 | 13 | 14 | 15 | 16 | 17 | 18 | 19 | 20 |
| Herceptin | D | I | Q | M | T | Q | S | P | S | S | L | S | A | S | V | G | D | R | V | T |
| Campath-1G | D | I | K | M | T | Q | S | P | S | F | L | S | A | S | V | G | D | R | V | T |
| Rituxan | Q | I | V | L | S | Q | S | P | A | I | L | S | A | S | P | G | E | K | V | T |
| Erbitux | D | I | L | L | T | Q | S | P | V | I | L | S | V | S | P | G | E | R | V | S |

| | | | C | D | R | 1 | | | | | | | | | | | | | | |
|---|---|---|---|---|---|---|---|---|---|---|---|---|---|---|---|---|---|---|---|---|
| Kabat | 21 | 22 | 23 | 24 | 25 | 26 | 27 | 27a | 27b | 27c | 27d | 27e | 27f | 28 | 29 | 30 | 31 | 32 | 33 | 34 |
| Chothia | 21 | 22 | 23 | 24 | 25 | 26 | 27 | 28 | 29 | 30 | 30a | 30b | 30c | 30d | 30e | 30f | 31 | 32 | 33 | 34 |
| Herceptin | I | T | C | R | A | S | Q | | | | | | | D | V | N | T | A | V | A |
| Campath-1G | L | N | C | K | A | S | Q | | | | | | | N | I | D | K | Y | L | N |
| Rituxan | M | T | C | R | A | S | S | | | | | | | S | V | S | | Y | I | H |
| Erbitux | F | S | C | R | A | S | Q | | | | | | | S | I | G | T | N | I | H |

| | F | R | 2 | | | | | | | | | | | | | | C | D | R | 2 |
|---|---|---|---|---|---|---|---|---|---|---|---|---|---|---|---|---|---|---|---|---|
| Kabat | 35 | 36 | 37 | 38 | 39 | 40 | 41 | 42 | 43 | 44 | 45 | 46 | 47 | 48 | 49 | 50 | 51 | 52 | 53 | 54 |
| Chothia | 35 | 36 | 37 | 38 | 39 | 40 | 41 | 42 | 43 | 44 | 45 | 46 | 47 | 48 | 49 | 50 | 51 | 52 | 53 | 54 |
| Herceptin | W | Y | Q | Q | K | P | G | K | A | P | K | L | L | I | Y | S | A | S | F | L |
| Campath-1G | W | Y | Q | Q | K | L | G | E | S | P | K | L | L | I | Y | N | T | N | N | L |
| Rituxan | W | F | Q | Q | K | P | G | S | S | P | K | P | W | I | Y | A | T | S | N | L |
| Erbitux | W | Y | Q | Q | R | T | N | G | S | P | R | L | L | I | K | Y | A | S | E | S |

| | | F | R | 3 | | | | | | | | | | | | | | | | |
|---|---|---|---|---|---|---|---|---|---|---|---|---|---|---|---|---|---|---|---|---|
| Kabat | 55 | 56 | 57 | 58 | 59 | 60 | 61 | 62 | 63 | 64 | 65 | 66 | 67 | 68 | 69 | 70 | 71 | 72 | 73 | 74 |
| Chothia | 55 | 56 | 57 | 58 | 59 | 60 | 61 | 62 | 63 | 64 | 65 | 66 | 67 | 68 | 69 | 70 | 71 | 72 | 73 | 74 |
| Herceptin | Y | S | G | V | P | S | R | F | S | G | S | R | S | G | T | D | F | T | L | T |
| Campath-1G | Q | T | G | I | P | S | R | F | S | G | S | G | S | G | T | D | F | T | L | T |
| Rituxan | A | S | G | V | P | V | R | F | S | G | S | G | S | G | T | S | Y | S | L | T |
| Erbitux | I | S | G | I | P | S | R | F | S | G | S | G | S | G | T | D | F | T | L | S |

| | | | | | | | | | | | | | | C | D | R | 3 | | | |
|---|---|---|---|---|---|---|---|---|---|---|---|---|---|---|---|---|---|---|---|---|
| Kabat | 75 | 76 | 77 | 78 | 79 | 80 | 81 | 82 | 83 | 84 | 85 | 86 | 87 | 88 | 89 | 90 | 91 | 92 | 93 | 94 |
| Chothia | 75 | 76 | 77 | 78 | 79 | 80 | 81 | 82 | 83 | 84 | 85 | 86 | 87 | 88 | 89 | 90 | 91 | 92 | 93 | 94 |
| Herceptin | I | S | S | L | Q | P | E | D | F | A | T | Y | Y | C | Q | Q | H | Y | T | T |
| Campath-1G | I | S | S | L | Q | P | E | D | V | A | T | Y | F | C | L | Q | H | I | S | R |
| Rituxan | I | S | R | V | E | A | E | D | A | A | T | Y | Y | C | Q | Q | W | T | S | N |
| Erbitux | I | N | S | V | E | S | E | D | I | A | D | Y | Y | C | Q | Q | N | N | N | W |

| | | | F | R | 4 | | | | | | | |
|---|---|---|---|---|---|---|---|---|---|---|---|---|
| Kabat | 95 | 96 | 97 | 98 | 99 | 100 | 101 | 102 | 103 | 104 | 105 | 106 | 107 |
| Chothia | 95 | 96 | 97 | 98 | 99 | 100 | 101 | 102 | 103 | 104 | 105 | 106 | 107 |
| Herceptin | P | P | T | F | G | Q | G | T | K | V | E | I | K |
| Campath-1G | P | R | T | F | G | T | G | T | K | L | E | L | K |
| Rituxan | P | P | T | F | G | G | G | T | K | L | E | I | K |
| Erbitux | P | T | T | F | G | A | G | T | K | L | E | L | K |

| Jκ Germline | | | | | | | | | | | | | |
|---|---|---|---|---|---|---|---|---|---|---|---|---|---|
| J1 | | W | T | F | G | Q | G | T | K | V | E | I | K |
| J2 | | Y | T | F | G | Q | G | T | K | L | E | I | K |
| J3 | | F | T | F | G | P | G | T | K | V | D | I | K |
| J4 | | L | T | F | G | G | G | T | K | V | E | I | K |
| J5 | | I | T | F | G | Q | G | T | R | L | E | I | K |

Figure 3b. VH

|  | FR 1 | | | | | | | | | | | | | | | | | | | | | | |
|---|---|---|---|---|---|---|---|---|---|---|---|---|---|---|---|---|---|---|---|---|---|---|---|
| Kabat | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| Chothia | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 |
| Herceptin | E | V | Q | L | V | E | S | G | G | G | L | V | Q | P | G | G | S | L | R | L | S | C | A |
| Campath-1G | E | V | K | L | L | E | S | G | G | G | L | V | Q | P | G | G | S | M | R | L | S | C | A |
| Rituxan | Q | V | Q | L | Q | Q | P | G | A | E | L | V | K | P | G | A | S | V | K | M | S | C | K |
| Erbitux | Q | V | Q | L | K | Q | S | G | P | G | L | V | Q | P | S | Q | S | L | S | I | T | C | T |

|  | CDR 1 | | | | | | | | | | | FR 2 | | | | | | | | | | | |
|---|---|---|---|---|---|---|---|---|---|---|---|---|---|---|---|---|---|---|---|---|---|---|---|
| Kabat | 24 | 25 | 26 | 27 | 28 | 29 | 30 | 31 | 32 | 33 | 34 | 35 | 35a | 35b | 36 | 37 | 38 | 39 | 40 | 41 | 42 | 43 | 44 |
| Chothia | 24 | 25 | 26 | 27 | 28 | 29 | 30 | 31 | 31a | 31b | 32 | 33 | 34 | 35 | 36 | 37 | 38 | 39 | 40 | 41 | 42 | 43 | 44 |
| Herceptin | A | S | G | F | N | I | K | D | T | Y | I | H |  |  | W | V | R | Q | A | P | G | K | G |
| Campath-1G | G | S | G | F | T | F | T | D | F | Y | M | N |  |  | W | I | R | Q | P | A | G | K | A |
| Rituxan | A | S | G | Y | T | F | T | S | Y | N | M | H |  |  | W | V | K | Q | T | P | G | R | G |
| Erbitux | V | S | G | F | S | L | T | N | Y | G | V | H |  |  | W | V | R | Q | S | P | G | K | G |

|  | CDR 2 | | | | | | | | | | | | FR 3 | | | | | | | | | | |
|---|---|---|---|---|---|---|---|---|---|---|---|---|---|---|---|---|---|---|---|---|---|---|---|
| Kabat | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 |
| Chothia | 45 | 46 | 47 | 48 | 49 | 50 | 51 | 52 | 52a | 52b | 52c | 53 | 54 | 55 | 56 | 57 | 58 | 59 | 60 | 61 | 62 | 63 | 64 |
| Herceptin | L | E | W | V | A | R | I | Y | P |  |  | T | N | G | Y | T | R | Y | A | D | S | V | K |
| Campath-1G | P | E | W | L | G | F | I | R | D | K | A | K | G | Y | T | T | E | Y | N | P | S | V | K |
| Rituxan | L | E | W | I | G | A | I | Y | P |  |  | G | N | G | D | T | S | Y | N | Q | K | F | K |
| Erbitux | L | E | W | L | G | V | I | W |  |  |  | S | G | G | N | T | D | Y | N | T | P | F | T |

|  | | | | | | | | | | | | | | | | | | | | | | | |
|---|---|---|---|---|---|---|---|---|---|---|---|---|---|---|---|---|---|---|---|---|---|---|---|
| Kabat | 65 | 66 | 67 | 68 | 69 | 70 | 71 | 72 | 73 | 74 | 75 | 76 | 77 | 78 | 79 | 80 | 81 | 82 | 82a | 82b | 82c | 83 | 84 |
| Chothia | 65 | 66 | 67 | 68 | 69 | 70 | 71 | 72 | 73 | 74 | 75 | 76 | 77 | 78 | 79 | 80 | 81 | 82 | 82a | 82b | 82c | 83 | 84 |
| Herceptin | G | R | F | T | I | S | A | D | T | S | K | N | T | A | Y | L | Q | M | N | S | L | R | A |
| Campath-1G | G | R | F | T | I | S | R | D | N | T | Q | N | M | L | Y | L | Q | M | N | T | L | R | A |
| Rituxan | G | K | A | T | L | T | A | D | K | S | S | S | T | A | Y | M | Q | L | S | S | L | T | S |
| Erbitux | S | R | L | S | I | N | K | D | N | S | K | S | Q | V | F | F | K | M | N | S | L | Q | S |

|  | | | | | | | | | | |
|---|---|---|---|---|---|---|---|---|---|---|
| Kabat | 85 | 86 | 87 | 88 | 89 | 90 | 91 | 92 | 93 | 94 |
| Chothia | 85 | 86 | 87 | 88 | 89 | 90 | 91 | 92 | 93 | 94 |
| Herceptin | E | D | T | A | V | Y | Y | C | S | R |
| Campath-1G | E | D | T | A | T | Y | Y | C | A | R |
| Rituxan | E | D | S | A | V | Y | Y | C | A | R |
| Erbitux | N | D | T | A | I | Y | Y | C | A | R |

|  | CDR 3 | | | | | | | | | | FR 4 | | | | | | | | | | | | |
|---|---|---|---|---|---|---|---|---|---|---|---|---|---|---|---|---|---|---|---|---|---|---|---|
| Kabat | 95 | 96 | 97 | 98 | 99 | 100 | 100a | 100b | 100c | 100d | 101 | 102 | 103 | 104 | 105 | 106 | 107 | 108 | 109 | 110 | 111 | 112 | 113 |
| Chothia | 95 | 96 | 97 | 98 | 99 | 100 | 100a | 100b | 100c | 100d | 101 | 102 | 103 | 104 | 105 | 106 | 107 | 108 | 109 | 110 | 111 | 112 | 113 |
| Herceptin | W | G | G | D | G | F | Y | A |  | M | D | Y | W | G | Q | G | T | L | V | T | V | S | S |
| Campath-1G | E | G | H | T | A | A | P |  |  | F | D | Y | W | G | Q | G | V | M | V | T | V | S | S |
| Rituxan | S | T | Y | Y | G | G | D | W | Y | F | N | V | W | G | A | G | T | T | V | T | V | S | A |
| Erbitux | A | L | T | Y | Y | D | Y | E |  | F | A | Y | W | G | Q | G | T | L | V | T | V | S | A |

| JH Germline | | | | | | | | | | | | | | | | | | | | | | | |
|---|---|---|---|---|---|---|---|---|---|---|---|---|---|---|---|---|---|---|---|---|---|---|---|
| J1 |  |  |  |  |  | A | E | Y | F | Q | H | W | G | Q | G | T | L | V | T | V | S | S |  |
| J2 |  |  |  |  |  | Y | W | Y | F | D | L | W | G | R | G | T | L | V | T | V | S | S |  |
| J3 |  |  |  |  |  |  | A | F | D | V | W | G | Q | G | T | M | V | T | V | S | S |  |  |
| J4 |  |  |  |  |  |  | Y | F | D | Y | W | G | Q | G | T | L | V | T | V | S | S |  |  |
| J5 |  |  |  |  |  | N | W | F | D | S | W | G | Q | G | T | L | V | T | V | S | S |  |  |
| J6 |  |  | Y | Y | Y | Y | Y | G | M | D | V | W | G | Q | G | T | T | V | T | V | S | S |  |

Figure 3c. CL

| CL | | | | | | | | | | | | | | | | | | |
|---|---|---|---|---|---|---|---|---|---|---|---|---|---|---|---|---|---|---|
| EU | 108 | 109 | 110 | 111 | 112 | 113 | 114 | 115 | 116 | 117 | 118 | 119 | 120 | 121 | 122 | 123 | 124 | 125 |
| Cκ | R | T | V | A | A | P | S | V | F | I | F | P | P | S | D | E | Q | L |
| Cλ | Q | P | K | A | A | P | S | V | T | L | F | P | P | S | S | E | E | L |
| | | | | | | | | | | | | | | | | | | |
| EU | 126 | 127 | 128 | 129 | 130 | 131 | 132 | 133 | 134 | 135 | 136 | 137 | 138 | 139 | 140 | 141 | 142 | 143 |
| Cκ | K | S | G | T | A | S | V | V | C | L | L | N | N | F | Y | P | R | E |
| Cλ | Q | A | N | K | A | T | L | V | C | L | I | S | D | F | Y | P | G | A |
| | | | | | | | | | | | | | | | | | | |
| EU | 144 | 145 | 146 | 147 | 148 | 149 | 150 | 151 | 152 | 153 | | 154 | 155 | 156 | 157 | 158 | 159 | 160 |
| Cκ | A | K | V | Q | W | K | V | D | N | A | | L | Q | S | G | N | S | Q |
| Cλ | V | T | V | A | W | K | A | D | S | S | P | V | K | A | G | | | V |
| | | | | | | | | | | | | | | | | | | |
| EU | 161 | 162 | 163 | 164 | 165 | 166 | 167 | 168 | 169 | 170 | 171 | 172 | 173 | 174 | 175 | 176 | 177 | 178 |
| Cκ | E | S | V | T | E | Q | D | S | K | D | S | T | Y | S | L | S | S | T |
| Cλ | E | T | T | T | P | S | K | Q | S | N | N | K | Y | A | A | S | S | Y |
| | | | | | | | | | | | | | | | | | | |
| EU | 179 | 180 | 181 | 182 | 183 | 184 | 185 | 186 | 187 | 188 | 189 | 190 | 191 | 192 | 193 | 194 | 195 | 196 |
| Cκ | L | T | L | S | K | A | D | Y | E | K | H | K | V | Y | A | C | E | V |
| Cλ | L | S | L | T | P | E | Q | W | K | S | H | R | S | Y | S | C | Q | V |
| | | | | | | | | | | | | | | | | | | |
| EU | 197 | 198 | 199 | 200 | 201 | 202 | 203 | 204 | 205 | 206 | 207 | 208 | 209 | 210 | 211 | 212 | 213 | 214 |
| Cκ | T | H | Q | G | L | S | S | P | V | T | K | S | F | N | R | G | E | C |
| Cλ | T | H | E | G | | S | T | V | E | K | T | V | A | P | T | E | C | |

Figure 3d. IgG CH1

| CH1 | | | | | | | | | | | | | | | | | | | | |
|---|---|---|---|---|---|---|---|---|---|---|---|---|---|---|---|---|---|---|---|---|
| EU | 118 | 119 | 120 | 121 | 122 | 123 | 124 | 125 | 126 | 127 | 128 | 129 | 130 | 131 | 132 | 133 | 134 | 135 | 136 | 137 | 138 |
| IgG1 | A | S | T | K | G | P | S | V | F | P | L | A | P | S | S | K | S | T | S | G | G |
| IgG2 | A | S | T | K | G | P | S | V | F | P | L | A | P | C | S | R | S | T | S | E | S |
| IgG3 | A | S | T | K | G | P | S | V | F | P | L | A | P | C | S | R | S | T | S | G | G |
| IgG4 | A | S | T | K | G | P | S | V | F | P | L | A | P | C | S | R | S | T | S | E | S |
| | | | | | | | | | | | | | | | | | | | | | |
| EU | 139 | 140 | 141 | 142 | 143 | 144 | 145 | 146 | 147 | 148 | 149 | 150 | 151 | 152 | 153 | 154 | 155 | 156 | 157 | 158 | 159 |
| IgG1 | T | A | A | L | G | C | L | V | K | D | Y | F | P | E | P | V | T | V | S | W | N |
| IgG2 | T | A | A | L | G | C | L | V | K | D | Y | F | P | E | P | V | T | V | S | W | N |
| IgG3 | T | A | A | L | G | C | L | V | K | D | Y | F | P | E | P | V | T | V | S | W | N |
| IgG4 | T | A | A | L | G | C | L | V | K | D | Y | F | P | E | P | V | T | V | S | W | N |
| | | | | | | | | | | | | | | | | | | | | | |
| EU | 160 | 161 | 162 | 163 | 164 | 165 | 166 | 167 | 168 | 169 | 170 | 171 | 172 | 173 | 174 | 175 | 176 | 177 | 178 | 179 | 180 |
| IgG1 | S | G | A | L | T | S | G | V | H | T | F | P | A | V | L | Q | S | S | G | L | Y |
| IgG2 | S | G | A | L | T | S | G | V | H | T | F | P | A | V | L | Q | S | S | G | L | Y |
| IgG3 | S | G | A | L | T | S | G | V | H | T | F | P | A | V | L | Q | S | S | G | L | Y |
| IgG4 | S | G | A | L | T | S | G | V | H | T | F | P | A | V | L | Q | S | S | G | L | Y |
| | | | | | | | | | | | | | | | | | | | | | |
| EU | 181 | 182 | 183 | 184 | 185 | 186 | 187 | 188 | 189 | 190 | 191 | 192 | 193 | 194 | 195 | 196 | 197 | 198 | 199 | 200 | 201 |
| IgG1 | S | L | S | S | V | V | T | V | P | S | S | S | L | G | T | Q | T | Y | I | C | N |
| IgG2 | S | L | S | S | V | V | T | V | P | S | S | N | F | G | T | Q | T | Y | T | C | N |
| IgG3 | S | L | S | S | V | V | T | V | P | S | S | S | L | G | T | Q | T | Y | T | C | N |
| IgG4 | S | L | S | S | V | V | T | V | P | S | S | S | L | G | T | K | T | Y | T | C | N |
| | | | | | | | | | | | | | | | | | | | | | |
| EU | 202 | 203 | 204 | 205 | 206 | 207 | 208 | 209 | 210 | 211 | 212 | 213 | 214 | 215 | 216 | 217 | 218 | 219 | 220 | | |
| IgG1 | V | N | H | K | P | S | N | T | K | V | D | K | K | V | E | P | K | S | C | | |
| IgG2 | V | D | H | K | P | S | N | T | K | V | D | K | T | V | E | R | K | C | C | | |
| IgG3 | V | N | H | K | P | S | N | T | K | V | D | K | R | V | E | L | K | T | P | | |
| IgG4 | V | D | H | K | P | S | N | T | K | V | D | K | R | V | E | S | K | Y | G | | |

Figure 3e. IgG Hinge

| Hinge | | | | | | | | | | | | | | | | | | | | | |
|---|---|---|---|---|---|---|---|---|---|---|---|---|---|---|---|---|---|---|---|---|---|
| EU | 221 | | | 222 | 223 | 224 | 225 | 226 | 227 | 228 | | | | | | | | | | | |
| IgG1 | D | | | K | T | H | T | C | P | P | | | | | | | | | | | |
| IgG2 | | | | V | | E | | C | P | P | | | | | | | | | | | |
| IgG3 | L | G | D | T | T | H | T | C | P | R | C | P | E | P | K | S | C | D | T | P | P |
| IgG4 | | | | | | P | P | C | P | S | | | | | | | | | | | |

| | | | | | | | | | | | | | | | | | | | | | |
|---|---|---|---|---|---|---|---|---|---|---|---|---|---|---|---|---|---|---|---|---|---|
| EU | | | | | | | | | | | | | | | | | | | | | |
| IgG1 | | | | | | | | | | | | | | | | | | | | | |
| IgG2 | | | | | | | | | | | | | | | | | | | | | |
| IgG3 | P | C | P | R | C | P | E | P | K | S | C | D | T | P | P | P | C | P | R | C | P |
| IgG4 | | | | | | | | | | | | | | | | | | | | | |

| | | | | | | | | | | | | | | | | | | | | | |
|---|---|---|---|---|---|---|---|---|---|---|---|---|---|---|---|---|---|---|---|---|---|
| EU | | | | | | | | | | | | 229 | 230 | 231 | 232 | 233 | 234 | 235 | 236 | | |
| IgG1 | | | | | | | | | | | | C | P | A | P | E | L | L | G | | |
| IgG2 | | | | | | | | | | | | C | P | A | P | P | V | A | | | |
| IgG3 | E | P | K | S | C | D | T | P | P | P | C | P | R | C | P | A | P | E | L | L | G |
| IgG4 | | | | | | | | | | | | C | P | A | P | E | F | L | G | | |

Figure 3f. IgG CH2 and CH3

| CH2 | | | | | | | | | | | | | | | | | | | | |
|---|---|---|---|---|---|---|---|---|---|---|---|---|---|---|---|---|---|---|---|---|
| EU | 237 | 238 | 239 | 240 | 241 | 242 | 243 | 244 | 245 | 246 | 247 | 248 | 249 | 250 | 251 | 252 | 253 | 254 | 255 | 256 | 257 |
| IgG1 | G | P | S | V | F | L | F | P | P | K | P | K | D | T | L | M | I | S | R | T | P |
| IgG2 | G | P | S | V | F | L | F | P | P | K | P | K | D | T | L | M | I | S | R | T | P |
| IgG3 | G | P | S | V | F | L | F | P | P | K | P | K | D | T | L | M | I | S | R | T | P |
| IgG4 | G | P | S | V | F | L | F | P | P | K | P | K | D | T | L | M | I | S | R | T | P |

| EU | 258 | 259 | 260 | 261 | 262 | 263 | 264 | 265 | 266 | 267 | 268 | 269 | 270 | 271 | 272 | 273 | 274 | 275 | 276 | 277 | 278 |
|---|---|---|---|---|---|---|---|---|---|---|---|---|---|---|---|---|---|---|---|---|---|
| IgG1 | E | V | T | C | V | V | V | D | V | S | H | E | D | P | E | V | K | F | N | W | Y |
| IgG2 | E | V | T | C | V | V | V | D | V | S | H | E | D | P | E | V | Q | F | N | W | Y |
| IgG3 | E | V | T | C | V | V | V | D | V | S | H | E | D | P | E | V | Q | F | K | W | Y |
| IgG4 | E | V | T | C | V | V | V | D | V | S | Q | E | D | P | E | V | Q | F | N | W | Y |

| EU | 279 | 280 | 281 | 282 | 283 | 284 | 285 | 286 | 287 | 288 | 289 | 290 | 291 | 292 | 293 | 294 | 295 | 296 | 297 | 298 | 299 |
|---|---|---|---|---|---|---|---|---|---|---|---|---|---|---|---|---|---|---|---|---|---|
| IgG1 | V | D | G | V | E | V | H | N | A | K | T | K | P | R | E | E | Q | Y | N | S | T |
| IgG2 | V | D | G | V | E | V | H | N | A | K | T | K | P | R | E | E | Q | F | N | S | T |
| IgG3 | V | D | G | V | E | V | H | N | A | K | T | K | P | R | E | E | Q | Y | N | S | T |
| IgG4 | V | D | G | V | E | V | H | N | A | K | T | K | P | R | E | E | Q | F | N | S | T |

| EU | 300 | 301 | 302 | 303 | 304 | 305 | 306 | 307 | 308 | 309 | 310 | 311 | 312 | 313 | 314 | 315 | 316 | 317 | 318 | 319 | 320 |
|---|---|---|---|---|---|---|---|---|---|---|---|---|---|---|---|---|---|---|---|---|---|
| IgG1 | Y | R | V | V | S | V | L | T | V | L | H | Q | D | W | L | N | G | K | E | Y | K |
| IgG2 | F | R | V | V | S | V | L | T | V | V | H | Q | D | W | L | N | G | K | E | Y | K |
| IgG3 | F | R | V | V | S | V | L | T | V | L | H | Q | D | W | L | N | G | K | E | Y | K |
| IgG4 | Y | R | V | V | S | V | L | T | V | L | H | Q | D | W | L | N | G | K | E | Y | K |

| EU | 321 | 322 | 323 | 324 | 325 | 326 | 327 | 328 | 329 | 330 | 331 | 332 | 333 | 334 | 335 | 336 | 337 | 338 | 339 | 340 | |
|---|---|---|---|---|---|---|---|---|---|---|---|---|---|---|---|---|---|---|---|---|---|
| IgG1 | C | K | V | S | N | K | A | L | P | A | P | I | E | K | T | I | S | K | A | K | |
| IgG2 | C | K | V | S | N | K | G | L | P | A | P | I | E | K | T | I | S | K | T | K | |
| IgG3 | C | K | V | S | N | K | A | L | P | A | P | I | E | K | T | I | S | K | T | K | |
| IgG4 | C | K | V | S | N | K | G | L | P | S | S | I | E | K | T | I | S | K | A | K | |

| CH3 | | | | | | | | | | | | | | | | | | | | | |
|---|---|---|---|---|---|---|---|---|---|---|---|---|---|---|---|---|---|---|---|---|---|
| EU | 341 | 342 | 343 | 344 | 345 | 346 | 347 | 348 | 349 | 350 | 351 | 352 | 353 | 354 | 355 | 356 | 357 | 358 | 359 | 360 | 361 |
| IgG1 | G | Q | P | R | E | P | Q | V | Y | T | L | P | P | S | R | D | E | L | T | K | N |
| IgG2 | G | Q | P | R | E | P | Q | V | Y | T | L | P | P | S | R | E | E | M | T | K | N |
| IgG3 | G | Q | P | R | E | P | Q | V | Y | T | L | P | P | S | R | E | E | M | T | K | N |
| IgG4 | G | Q | P | R | E | P | Q | V | Y | T | L | P | P | S | Q | E | E | M | T | K | N |

| EU | 362 | 363 | 364 | 365 | 366 | 367 | 368 | 369 | 370 | 371 | 372 | 373 | 374 | 375 | 376 | 377 | 378 | 379 | 380 | 381 | 382 |
|---|---|---|---|---|---|---|---|---|---|---|---|---|---|---|---|---|---|---|---|---|---|
| IgG1 | Q | V | S | L | T | C | L | V | K | G | F | Y | P | S | D | I | A | V | E | W | E |
| IgG2 | Q | V | S | L | T | C | L | V | K | G | F | Y | P | S | D | I | A | V | E | W | E |
| IgG3 | Q | V | S | L | T | C | L | V | K | G | F | Y | P | S | D | I | A | V | E | W | E |
| IgG4 | Q | V | S | L | T | C | L | V | K | G | F | Y | P | S | D | I | A | V | E | W | E |

| EU | 383 | 384 | 385 | 386 | 387 | 388 | 389 | 390 | 391 | 392 | 393 | 394 | 395 | 396 | 397 | 398 | 399 | 400 | 401 | 402 | 403 |
|---|---|---|---|---|---|---|---|---|---|---|---|---|---|---|---|---|---|---|---|---|---|
| IgG1 | S | N | G | Q | P | E | N | N | Y | K | T | T | P | P | V | L | D | S | D | G | S |
| IgG2 | S | N | G | Q | P | E | N | N | Y | K | T | T | P | P | M | L | D | S | D | G | S |
| IgG3 | S | S | G | Q | P | E | N | N | Y | N | T | T | P | P | M | L | D | S | D | G | S |
| IgG4 | S | N | G | Q | P | E | N | N | Y | K | T | T | P | P | V | L | D | S | D | G | S |

| EU | 404 | 405 | 406 | 407 | 408 | 409 | 410 | 411 | 412 | 413 | 414 | 415 | 416 | 417 | 418 | 419 | 420 | 421 | 422 | 423 | 424 |
|---|---|---|---|---|---|---|---|---|---|---|---|---|---|---|---|---|---|---|---|---|---|
| IgG1 | F | F | L | Y | S | K | L | T | V | D | K | S | R | W | Q | Q | G | N | V | F | S |
| IgG2 | F | F | L | Y | S | K | L | T | V | D | K | S | R | W | Q | Q | G | N | V | F | S |
| IgG3 | F | F | L | Y | S | K | L | T | V | D | K | S | R | W | Q | Q | G | N | I | F | S |
| IgG4 | F | F | L | Y | S | R | L | T | V | D | K | S | R | W | Q | E | G | N | V | F | S |

| EU | 425 | 426 | 427 | 428 | 429 | 430 | 431 | 432 | 433 | 434 | 435 | 436 | 437 | 438 | 439 | 440 | 441 | 442 | 443 | 444 | 445 |
|---|---|---|---|---|---|---|---|---|---|---|---|---|---|---|---|---|---|---|---|---|---|
| IgG1 | C | S | V | M | H | E | A | L | H | N | H | Y | T | Q | K | S | L | S | L | S | P |
| IgG2 | C | S | V | M | H | E | A | L | H | N | H | Y | T | Q | K | S | L | S | L | S | P |
| IgG3 | C | S | V | M | H | E | A | L | H | N | R | F | T | Q | K | S | L | S | L | S | P |
| IgG4 | C | S | V | M | H | E | A | L | H | N | H | Y | T | Q | K | S | L | S | L | S | L |

| EU | 446 | 447 |
|---|---|---|
| IgG1 | G | K |
| IgG2 | G | K |
| IgG3 | G | K |
| IgG4 | G | K |

Figure 14a

| JL Kabat | WT | A | R | N | D | C | Q | E | G | HID | HIE | HSP | I | L | K | M | F | P | S | T | W | Y | V |
|---|---|---|---|---|---|---|---|---|---|---|---|---|---|---|---|---|---|---|---|---|---|---|---|
| 100 | O | 0.69 | 1.02 | 1.21 | 0.84 | 7.37 | 1.55 | 0.67 | 0.00 | 2.35 | 2.84 | 3.79 | 0.68 | 0.47 | 0.36 | 1.40 | 3.23 | 4.56 | 1.11 | 0.76 | 3.35 | 2.84 | 1.44 |
| 101 | G | nd | nd | nd | 124.10 | nd | nd | nd | 0.00 | nd | nd | nd | nd | nd | nd | nd | nd | nd | 129.56 | nd | nd | 153.86 | nd |
| 102 | T | 1.19 | nd | 5.74 | 2.61 | 7.02 | 12.45 | 14.57 | 2.31 | nd | 16.28 | nd | 27.09 | nd | 8.83 | 8.75 | nd | nd | 1.92 | 0.00 | nd | nd | 22.99 |
| 103 | K | 1.91 | 1.11 | 2.32 | 3.09 | 8.63 | 2.81 | 4.18 | 1.65 | 3.68 | 4.09 | 2.62 | 2.32 | 2.02 | 0.00 | 3.12 | 4.63 | 21.80 | 2.43 | 2.29 | 3.62 | 4.36 | 2.64 |
| 104 | V | 2.30 | 24.38 | 3.13 | 3.99 | 8.63 | 9.16 | 8.24 | 2.70 | 14.18 | 30.44 | 14.98 | 1.80 | 0.44 | 3.91 | 2.06 | nd | nd | 3.35 | 1.95 | nd | nd | 0.00 |
| 105 | E | 0.74 | 3.40 | 1.94 | 0.53 | 8.06 | 2.56 | 0.29 | 1.01 | 5.31 | 5.13 | 7.65 | 0.30 | 2.71 | 2.08 | 1.48 | 4.10 | 22.04 | 1.66 | 0.65 | 5.89 | 3.44 | 0.00 |
| 106 | I | 2.20 | 10.30 | 5.30 | 5.97 | 9.27 | 8.10 | 7.58 | 2.84 | 10.90 | 22.80 | 12.37 | 0.00 | 7.26 | 4.40 | 2.31 | 30.51 | 32.05 | 4.02 | 2.67 | nd | nd | 2.26 |
| 107 | K | 0.48 | 0.00 | 1.19 | 1.86 | 7.27 | 1.45 | 1.58 | 1.10 | 1.79 | 2.74 | 2.67 | 15.96 | 1.01 | 0.16 | 2.21 | 2.66 | nd | 1.23 | 1.47 | 2.51 | 2.25 | 6.02 |
| CL EU |  |  |  |  |  |  |  |  |  |  |  |  |  |  |  |  |  |  |  |  |  |  |  |
| 108 | R | 2.28 | 0.00 | 3.05 | 3.24 | 7.93 | 3.78 | 3.82 | 2.48 | 3.31 | 4.54 | 4.56 | 1.95 | 3.85 | 1.27 | 3.21 | 4.45 | 24.27 | 3.12 | 1.59 | 4.25 | 3.47 | 2.97 |
| 109 | T | 0.81 | 1.56 | 0.87 | 0.00 | 7.78 | 1.09 | 0.01 | 0.65 | 0.83 | 1.96 | 2.74 | 2.26 | 2.20 | 2.26 | 3.23 | 3.21 | 7.35 | 0.98 | 1.05 | 2.96 | 2.33 | 2.20 |
| 110 | V | 0.78 | 1.08 | 0.90 | 0.49 | 6.14 | 1.12 | 0.46 | 0.59 | 1.42 | 1.93 | 3.07 | 0.04 | 0.74 | 0.92 | 1.56 | 1.83 | 5.39 | 1.24 | 0.00 | 1.81 | 1.41 | 0.10 |
| 111 | A | 0.17 | 0.81 | 0.76 | 1.49 | 6.97 | 0.98 | 0.64 | 0.65 | 2.13 | 3.05 | 3.20 | 5.09 | 0.33 | 10.00 | 1.32 | 2.71 | nd | 1.26 | 2.88 | 7.99 | 2.14 | 5.59 |
| 112 | A | 0.00 | 0.13 | 0.33 | 0.47 | 7.05 | 0.16 | 0.42 | 0.69 | 0.36 | 1.53 | 1.68 | nd | 0.41 | 0.22 | 1.40 | 1.90 | 5.16 | 0.53 | 4.44 | 2.47 | 1.26 | nd |
| 113 | P | 0.00 | 12.71 | 0.81 | 1.73 | 5.14 | 9.69 | 9.88 | 0.73 | 22.47 | 62.83 | 21.54 | nd | 3.38 | 6.55 | 3.39 | nd | 3.49 | 1.17 | 0.64 | nd | nd | nd |
| 114 | S | 0.45 | 1.13 | 1.24 | 0.00 | 6.90 | 1.49 | 0.50 | 0.64 | 2.07 | 2.69 | 3.38 | 0.32 | 1.05 | 0.95 | 1.93 | 3.11 | 23.20 | 0.90 | 0.54 | 2.86 | 2.48 | 0.47 |
| 115 | V | 2.38 | 8.96 | 2.63 | 2.36 | 8.12 | 3.20 | 4.60 | 2.45 | 11.59 | 9.73 | 11.82 | 0.21 | 10.77 | 5.09 | 2.10 | 11.66 | 13.63 | 3.18 | 0.66 | 25.39 | 10.83 | 0.00 |
| 116 | F | 1.27 | 7.36 | 2.96 | 2.23 | 7.36 | 2.70 | 2.19 | 1.96 | 3.42 | 3.58 | 5.35 | 15.79 | 47.07 | 1.27 | 0.80 | 0.14 | nd | 2.74 | 11.49 | nd | 0.00 | 39.43 |
| 117 | I | 3.37 | nd | 4.67 | 3.95 | 8.86 | 4.37 | 4.65 | 3.40 | 43.17 | nd | 83.06 | 0.00 | 1.60 | 6.71 | 1.07 | nd | nd | 4.58 | 3.20 | nd | nd | 1.49 |
| 118 | F | 2.08 | 9.21 | 3.48 | 3.81 | 8.47 | 5.32 | 4.59 | 2.85 | 2.79 | 4.09 | 4.51 | 3.55 | 5.21 | 1.16 | 1.51 | 10.00 | nd | 3.40 | 8.08 | 13.79 | 3.40 | 8.78 |
| 119 | P | 0.49 | 6.37 | 1.97 | 0.00 | 6.64 | 2.93 | 1.72 | 1.73 | 2.05 | 3.09 | 4.02 | 7.37 | 2.91 | 0.68 | 0.31 | 0.70 | 5.28 | 1.49 | 4.63 | 5.20 | 1.75 | 9.31 |
| 120 | P | 0.00 | 5.97 | 9.69 | 7.54 | 6.19 | nd | 43.56 | 1.14 | nd | nd | nd | nd | nd | 18.43 | 4.16 | nd | 5.52 | 0.74 | 0.37 | nd | nd | 30.93 |
| 121 | S | 0.00 | 5.78 | 3.39 | 1.95 | 6.19 | 6.38 | 2.16 | 1.13 | 12.05 | 7.66 | 15.97 | 19.49 | 48.55 | 4.48 | 4.52 | 10.39 | 15.63 | 0.52 | 5.03 | nd | 13.73 | 11.23 |
| 122 | D | 3.02 | 2.93 | 1.96 | 0.00 | 9.47 | 2.38 | 0.00 | 2.21 | 2.60 | 3.41 | 5.30 | 2.91 | 3.06 | 3.82 | 3.68 | 4.16 | 6.45 | 2.79 | 2.03 | 3.44 | 2.41 | 3.30 |
| 123 | E | 1.67 | 4.55 | 2.82 | 0.00 | 9.29 | 3.32 | 0.63 | 1.62 | 2.16 | 4.25 | 5.63 | 2.38 | 2.50 | 4.51 | 4.25 | 4.67 | 10.04 | 1.82 | 1.56 | 4.76 | 2.77 | 2.65 |
| 124 | Q | 0.37 | 11.66 | 3.81 | 1.27 | 8.46 | 4.66 | 1.77 | 1.58 | 6.67 | 9.95 | 8.64 | 6.43 | 11.42 | 3.64 | 0.84 | 4.89 | nd | 0.00 | 1.99 | nd | 11.85 | 2.83 |
| 125 | L | 0.89 | 2.03 | 2.99 | 1.32 | 9.22 | 2.58 | 1.02 | 0.96 | 4.01 | 6.16 | 8.52 | 0.16 | 0.00 | 1.76 | 1.93 | 10.23 | nd | 1.85 | 2.21 | 8.20 | 8.16 | 1.23 |
| 126 | K | 0.39 | 0.38 | 0.27 | 0.06 | 7.70 | 0.70 | 0.03 | 0.00 | 1.27 | 1.61 | 2.27 | 1.68 | 1.84 | 0.53 | 2.57 | 2.75 | nd | 0.68 | 0.68 | 2.85 | 2.14 | 1.58 |
| 127 | S | 1.66 | 1.38 | 0.93 | 0.87 | 8.78 | 1.52 | 1.22 | 0.00 | 2.48 | 2.83 | 4.07 | 5.48 | 1.99 | 1.25 | 3.04 | 4.12 | nd | 1.59 | 0.71 | 3.92 | 2.96 | 5.47 |
| 128 | G | 26.35 | 9.14 | 8.08 | 7.33 | 19.34 | 9.03 | 8.40 | 0.00 | 9.86 | 10.35 | 12.46 | 22.03 | 9.86 | 9.54 | 12.39 | 14.09 | nd | 17.10 | 12.40 | 12.88 | 12.54 | 21.60 |
| 129 | T | 0.50 | 1.46 | 1.21 | 0.78 | 8.45 | 1.36 | 0.56 | 0.79 | 1.81 | 2.25 | 3.37 | 0.00 | 0.19 | 0.40 | 1.20 | 3.27 | 11.09 | 1.48 | 1.24 | 2.72 | 2.08 | 0.88 |
| 130 | A | 0.00 | nd | 10.91 | 8.61 | 10.23 | 9.16 | 12.02 | 1.50 | nd | nd | nd | nd | nd | 20.98 | 16.35 | nd | nd | 2.22 | 9.65 | nd | nd | nd |
| 131 | S | 0.30 | 27.97 | 3.74 | 5.44 | 8.87 | 13.48 | 11.42 | 0.84 | 16.50 | 12.02 | 14.19 | 11.04 | 26.35 | 17.28 | 9.81 | 32.51 | 12.95 | 0.00 | 2.93 | nd | 27.96 | 10.15 |
| 132 | V | 3.48 | 20.53 | 4.45 | 4.15 | 8.79 | 4.80 | 3.78 | 4.13 | 28.91 | 16.36 | 28.25 | 0.00 | 6.65 | 1.55 | 1.29 | 31.55 | 49.40 | 4.90 | 3.11 | nd | nd | 1.23 |
| 133 | V | 2.64 | 8.42 | 3.33 | 2.40 | 8.06 | 3.98 | 3.18 | 2.56 | 6.90 | 8.09 | 8.13 | 0.00 | 0.26 | 2.24 | 1.13 | 7.39 | 34.57 | 3.88 | 2.24 | 18.78 | 13.07 | 0.96 |
| 134 | C | 0.17 | nd | nd | 40.73 | 24.74 | nd | nd | 0.00 | 308.22 | nd | nd | nd | nd | nd | nd | 32.70 | nd | 5.13 | 33.65 | nd | nd | nd |
| 135 | L | 2.54 | 11.00 | 4.98 | 5.07 | 8.90 | 5.62 | 4.54 | 3.11 | 8.36 | 9.04 | 8.99 | 0.12 | 0.00 | 3.13 | 1.44 | 9.26 | nd | 4.62 | 3.11 | 13.53 | 15.18 | 1.30 |
| 136 | L | 3.88 | 32.92 | 5.67 | 6.59 | 10.48 | 7.95 | 8.87 | 4.32 | 18.86 | 17.39 | 17.06 | 32.61 | 0.00 | 4.21 | 2.82 | 24.92 | nd | 5.42 | 13.56 | nd | nd | 21.47 |
| 137 | N | 0.96 | 3.77 | 2.13 | 2.13 | 8.00 | 4.00 | 2.96 | 1.67 | 6.63 | 9.50 | 7.77 | 13.45 | 1.25 | 0.00 | 0.52 | 4.88 | nd | 1.87 | 1.73 | 7.69 | 3.28 | 10.03 |
| 138 | N | 0.00 | 1.46 | 2.66 | 1.83 | 7.81 | 2.44 | 2.45 | 0.00 | 3.12 | 5.63 | 3.78 | 1.95 | 1.17 | 0.61 | 3.59 | 4.22 | nd | 0.85 | 0.60 | 4.98 | 4.35 | 1.20 |
| 139 | F | 2.52 | 10.43 | 5.67 | 5.85 | 9.69 | 5.24 | 5.37 | 3.14 | 4.59 | 5.73 | 3.94 | nd | 2.29 | 1.07 | 0.54 | 0.00 | 50.09 | 4.74 | 3.83 | nd | 2.05 | nd |
| 140 | Y | 0.10 | 13.49 | 1.52 | 1.86 | 8.75 | 3.22 | 0.31 | 1.26 | 0.77 | 1.65 | 3.33 | 5.07 | 13.03 | 0.87 | 0.76 | 1.12 | nd | 1.47 | 6.32 | 3.74 | 0.00 | 6.85 |
| 141 | P | 1.34 | 1.47 | 1.84 | 1.00 | 7.30 | 1.98 | 0.83 | 1.11 | 2.42 | 3.34 | 4.27 | 1.39 | 0.00 | 0.03 | 1.21 | 2.71 | 7.18 | 1.94 | 1.43 | 3.31 | 2.73 | 1.22 |
| 142 | R | 2.17 | 0.49 | 2.43 | 3.24 | 8.73 | 2.14 | 3.26 | 2.52 | 3.41 | 3.40 | 3.12 | 1.86 | 1.35 | 0.00 | 2.21 | 4.27 | 6.97 | 2.77 | 2.53 | 2.97 | 3.28 | 1.98 |
| 143 | E | 1.05 | 1.43 | 0.88 | 0.00 | 7.78 | 1.39 | 0.01 | 1.00 | 1.66 | 2.20 | 3.83 | 1.66 | 1.27 | 1.62 | 2.33 | 3.76 | 8.95 | 1.23 | 1.03 | 2.39 | 2.57 | 1.77 |
| 144 | A | 0.00 | 25.14 | 11.49 | 5.94 | 8.36 | 15.50 | nd | 1.32 | nd | nd | nd | 28.17 | 37.71 | 6.84 | 4.25 | nd | nd | 1.24 | 0.77 | nd | nd | 5.33 |
| 145 | K | 1.28 | 0.00 | 1.13 | 1.93 | 8.16 | 1.49 | 2.09 | 0.64 | 2.20 | 2.49 | 2.22 | 2.00 | 1.90 | 0.07 | 2.47 | 3.14 | 31.03 | 1.65 | 1.31 | 1.59 | 2.24 | 2.39 |
| 146 | V | 3.69 | 3.79 | 4.30 | 4.01 | 8.80 | 5.67 | 4.27 | 3.65 | 5.84 | 5.46 | 6.76 | 0.00 | 3.19 | 3.02 | 2.41 | 6.24 | 8.29 | 2.25 | 1.99 | nd | 13.00 | 1.30 |
| 147 | Q | 1.32 | 1.66 | 0.98 | 0.26 | 8.47 | 1.18 | 0.00 | 1.75 | 4.08 | 4.27 | 5.80 | 1.97 | 0.37 | 1.20 | 1.51 | 4.08 | 40.75 | 1.99 | 1.13 | 4.40 | 2.36 | 2.57 |
| 148 | W | 3.46 | 8.72 | 5.79 | 5.38 | 12.16 | 6.46 | 5.86 | 4.21 | 6.62 | 6.84 | 8.05 | 10.93 | 2.08 | 2.58 | 3.19 | 2.94 | 15.86 | 5.11 | 11.52 | 0.00 | 27.51 | 12.93 |
| 149 | K | 2.67 | 1.28 | 2.75 | 2.74 | 8.37 | 2.58 | 3.41 | 3.21 | 3.01 | 2.85 | 3.59 | 2.78 | 3.18 | 0.00 | 1.79 | 1.85 | nd | 3.13 | 2.41 | 33.60 | 1.13 | 2.54 |
| 150 | V | 2.28 | 3.65 | 4.00 | 4.03 | 8.15 | 4.40 | 4.50 | 3.27 | 7.88 | 7.81 | 10.33 | 1.60 | 2.10 | 1.49 | 2.75 | 6.28 | 14.15 | 3.40 | 1.79 | 6.31 | 5.68 | 0.00 |
| 151 | D | 3.53 | 4.03 | 1.62 | 0.01 | 8.51 | 3.52 | 0.00 | 3.38 | 4.41 | 4.68 | 6.70 | 3.15 | 4.42 | 3.46 | 4.23 | 5.61 | nd | 3.59 | 3.94 | 5.05 | 4.90 | 3.86 |
| 152 | N | 1.42 | 1.30 | 0.73 | 0.30 | 7.93 | 1.42 | 0.37 | 0.00 | 1.26 | 2.09 | 3.28 | 2.66 | 2.22 | 2.02 | 3.12 | 3.20 | nd | 1.46 | 1.25 | 2.70 | 2.34 | 2.31 |
| 153 | A | 0.37 | 0.58 | 0.52 | 0.41 | 6.93 | 0.74 | 0.54 | 0.00 | 0.58 | 1.65 | 1.62 | 1.14 | 1.21 | 0.45 | 2.09 | 2.70 | nd | 0.69 | 0.51 | 2.91 | 1.68 | 1.23 |
| 154 | L | 1.19 | 1.43 | 0.97 | 0.30 | 7.78 | 1.46 | 0.00 | 1.08 | 2.29 | 2.61 | 3.61 | 1.58 | 1.31 | 1.63 | 2.32 | 3.10 | 6.47 | 1.87 | 1.24 | 3.35 | 2.80 | 1.12 |
| 155 | Q | 1.66 | 0.84 | 2.25 | 1.40 | 7.62 | 1.52 | 1.36 | 1.87 | 38.82 | nd | nd | 1.07 | 1.84 | 0.00 | 0.72 | nd | nd | 2.44 | 3.18 | nd | nd | 2.25 |
| 156 | S | 0.42 | 0.14 | 0.06 | 0.04 | 7.53 | 0.63 | 0.47 | 0.00 | 0.90 | 1.29 | 2.05 | 1.69 | 1.46 | 0.85 | 2.55 | 1.43 | 19.16 | 0.58 | 0.47 | 1.38 | 1.03 | 1.59 |

Figure 14a (continued)

| CL EU | WT | A | R | N | D | C | Q | E | G | HID | HIE | HSP | I | L | K | M | F | P | S | T | W | Y | V |
|---|---|---|---|---|---|---|---|---|---|---|---|---|---|---|---|---|---|---|---|---|---|---|---|
| 157 | G | 6.27 | 2.57 | 2.02 | 2.46 | 11.00 | 3.43 | 2.56 | 0.00 | 3.93 | 4.38 | 4.81 | 6.67 | 4.37 | 2.67 | 6.17 | 6.64 | nd | 5.16 | 3.71 | 6.23 | 5.61 | 7.28 |
| 158 | H | 0.23 | 0.00 | 0.34 | 0.82 | 6.94 | 0.38 | 1.03 | 0.34 | 0.63 | 1.81 | 2.01 | 2.14 | 0.86 | 0.00 | 1.93 | 2.83 | 43.87 | 0.86 | 0.64 | 3.03 | 2.14 | 0.13 |
| 159 | S | 0.53 | 1.79 | 1.92 | 1.51 | 7.52 | 1.42 | 0.38 | 1.32 | 2.54 | 3.33 | 3.67 | 8.91 | 0.11 | 0.00 | 0.53 | 2.23 | 10.90 | 1.19 | 0.55 | 2.91 | 1.82 | 5.75 |
| 160 | Q | 1.40 | 0.39 | 2.50 | 2.59 | 9.00 | 2.24 | 2.29 | 1.13 | 3.73 | 4.68 | 5.56 | 2.17 | 1.36 | 0.00 | 2.83 | 5.44 | 32.60 | 1.99 | 1.55 | 3.98 | 3.87 | 2.56 |
| 161 | E | 0.00 | 1.12 | 0.55 | 0.21 | 7.42 | 1.35 | 0.34 | 0.36 | 1.17 | 1.81 | 3.26 | 5.55 | 0.26 | 0.89 | 1.31 | 1.83 | 7.78 | 0.52 | 1.52 | 1.73 | 1.35 | 4.32 |
| 162 | S | 0.96 | 1.18 | 5.28 | 5.05 | 9.01 | 4.21 | 5.17 | 1.75 | nd | nd | nd | 12.36 | 23.85 | nd | 0.00 | 2.87 | nd | 53.39 | 1.17 | 2.33 | nd | nd | 3.08 |
| 163 | V | 2.10 | 1.50 | 3.04 | 2.99 | 8.84 | 2.34 | 2.68 | 2.14 | 3.36 | 5.05 | 4.20 | 1.50 | 1.71 | 0.00 | 2.61 | 4.29 | 10.87 | 3.03 | 1.57 | 4.88 | 4.17 | 1.18 |
| 164 | T | 4.04 | 2.98 | 5.57 | 8.55 | 10.00 | 6.10 | 7.65 | 4.64 | 9.29 | 8.10 | 6.22 | 2.49 | 4.58 | 0.00 | 3.57 | 8.53 | nd | 4.63 | 3.51 | 9.87 | 6.18 | 3.11 |
| 165 | E | 0.01 | 0.93 | 0.00 | 0.00 | 6.30 | 0.72 | 0.16 | 0.05 | 0.39 | 0.74 | 2.03 | 14.43 | 0.26 | 0.05 | 0.69 | 0.88 | 4.30 | 0.42 | 7.76 | 0.71 | 0.44 | 17.21 |
| 166 | Q | 2.91 | 11.79 | 4.66 | 5.79 | 8.36 | 1.56 | 3.45 | 3.87 | nd | nd | nd | nd | 24.05 | 0.10 | 0.00 | nd | nd | 4.38 | 15.54 | nd | nd | nd |
| 167 | D | 0.40 | 1.49 | 0.71 | 0.86 | 6.46 | 0.58 | 0.00 | 1.05 | 1.70 | 3.94 | 3.08 | 1.53 | 0.63 | 0.16 | 1.90 | 3.07 | nd | 0.24 | 0.04 | 3.62 | 2.62 | 0.83 |
| 168 | S | 1.23 | 1.41 | 1.30 | 0.71 | 8.03 | 1.78 | 0.00 | 0.91 | 1.63 | 2.25 | 3.15 | 1.66 | 0.64 | 0.52 | 2.01 | 2.20 | 6.12 | 1.67 | 1.12 | 1.89 | 1.20 | 1.59 |
| 169 | K | 1.07 | 0.98 | 1.28 | 2.38 | 8.03 | 1.99 | 2.40 | 0.56 | 1.37 | 2.81 | 1.87 | 2.59 | 2.58 | 0.94 | 3.80 | 3.81 | 9.57 | 0.17 | 0.00 | 3.68 | 3.00 | 2.03 |
| 170 | D | 1.70 | 2.98 | 2.33 | 0.00 | 8.81 | 2.69 | 1.32 | 1.43 | 2.11 | 3.62 | 4.36 | 2.13 | 2.72 | 2.89 | 4.18 | 4.53 | 13.15 | 1.39 | 0.99 | 4.05 | 3.28 | 2.22 |
| 171 | S | 0.00 | 24.34 | 2.18 | 2.30 | 6.48 | 18.27 | 17.11 | 0.91 | nd | nd | nd | 62.33 | nd | 18.39 | 11.98 | nd | nd | 1.55 | 14.05 | nd | nd | 24.71 |
| 172 | T | 1.49 | 2.14 | 2.32 | 3.59 | 8.22 | 4.25 | 2.68 | 1.96 | 5.84 | 6.06 | 5.04 | 0.23 | 0.99 | 0.62 | 2.37 | 6.43 | 22.93 | 2.64 | 0.65 | nd | 6.90 | 0.00 |
| 173 | Y | 2.98 | 6.87 | 3.97 | 6.64 | 11.10 | 4.72 | 4.65 | 3.84 | 3.65 | 5.94 | 4.94 | 1.74 | 0.95 | 0.98 | 0.29 | 0.00 | nd | 3.59 | 1.64 | 57.37 | 0.55 | 3.49 |
| 174 | S | 0.00 | 32.53 | 10.20 | 6.07 | 5.96 | 9.04 | 7.75 | 0.92 | nd | nd | nd | 15.01 | nd | 28.59 | 7.72 | nd | 22.68 | 0.68 | 2.21 | nd | nd | 10.75 |
| 175 | L | 3.04 | 3.61 | 4.11 | 5.83 | 10.05 | 3.60 | 5.18 | 5.21 | nd | 36.13 | nd | 25.49 | 1.23 | 0.00 | 2.31 | nd | nd | 3.54 | 4.03 | nd | nd | 8.54 |
| 176 | S | 0.63 | 5.49 | 3.93 | 3.62 | 8.07 | 3.93 | 4.33 | 1.71 | 132.33 | nd | nd | 1.22 | 12.61 | 0.00 | 1.31 | nd | nd | 1.73 | 1.71 | nd | nd | 1.05 |
| 177 | S | 0.00 | 9.96 | 2.54 | 3.76 | 6.70 | 12.52 | 11.91 | 0.98 | 20.54 | 10.35 | 17.01 | nd | 5.57 | 12.38 | nd | nd | 0.85 | 4.55 | nd | nd | nd | nd |
| 178 | T | 1.68 | 4.92 | 3.45 | 2.92 | 8.34 | 4.06 | 2.95 | 1.03 | 11.20 | 12.05 | 12.90 | 0.00 | 1.61 | 1.31 | 2.09 | nd | 19.79 | 3.21 | 1.75 | nd | nd | 0.94 |
| 179 | L | 2.87 | 10.31 | 4.32 | 4.79 | 10.39 | 3.66 | 3.33 | 6.03 | 4.70 | 4.66 | 7.20 | nd | 0.00 | 2.52 | 2.48 | 6.09 | nd | 5.19 | 8.83 | nd | 30.23 | nd |
| 180 | T | 1.32 | 3.31 | 2.18 | 1.75 | 10.07 | 3.13 | 1.73 | 1.37 | 4.99 | 5.32 | 6.90 | 0.94 | 0.99 | 1.06 | 2.27 | 3.85 | 15.65 | 0.67 | 0.00 | 5.24 | 4.46 | 0.90 |
| 181 | L | 2.00 | 2.28 | 2.52 | 3.67 | 8.27 | 2.78 | 2.65 | 1.84 | 2.65 | 3.54 | 4.50 | 2.84 | 0.34 | 0.00 | 1.11 | 7.15 | 27.78 | 2.70 | 2.22 | 12.89 | 21.65 | 4.20 |
| 182 | S | 2.08 | 1.35 | 1.94 | 1.62 | 8.56 | 1.72 | 1.31 | 1.75 | 2.80 | 3.16 | 4.28 | 2.29 | 2.88 | 1.61 | 3.51 | 4.46 | 6.49 | 0.00 | 0.17 | 4.37 | 3.66 | 1.72 |
| 183 | K | 1.15 | 0.78 | 1.43 | 1.19 | 8.01 | 2.26 | 2.00 | 1.47 | 2.58 | 2.49 | 3.36 | 1.75 | 1.48 | 0.00 | 3.06 | 2.71 | nd | 1.94 | 1.96 | 2.53 | 1.75 | 1.78 |
| 184 | A | 0.85 | 0.30 | 0.93 | 0.00 | 8.39 | 1.29 | 0.50 | 0.64 | 1.87 | 2.08 | 3.04 | 2.29 | 2.38 | 0.80 | 3.23 | 4.06 | 7.45 | 1.26 | 1.30 | 2.52 | 2.45 | 2.44 |
| 185 | D | 1.66 | 3.20 | 2.30 | 0.23 | 8.91 | 2.73 | 0.80 | 2.67 | 2.52 | 3.98 | 5.16 | 2.69 | 3.92 | 3.58 | 4.53 | 4.94 | 15.56 | 0.77 | 0.00 | 4.73 | 3.56 | 2.87 |
| 186 | Y | 2.30 | 8.05 | 3.84 | 4.01 | 9.08 | 5.20 | 3.72 | 3.95 | 2.84 | 4.78 | 5.80 | 50.13 | 2.92 | 2.17 | 0.76 | 0.00 | nd | 4.65 | 5.28 | 8.58 | 0.98 | 30.81 |
| 187 | E | 3.10 | 3.87 | 2.35 | 0.12 | 9.17 | 2.59 | 0.00 | 3.45 | 4.05 | 3.77 | 7.05 | 2.61 | 2.53 | 4.25 | 3.28 | 3.41 | nd | 1.96 | 2.12 | 5.16 | 4.98 | 3.73 |
| 188 | K | 0.98 | 0.06 | 0.83 | 2.08 | 8.87 | 1.40 | 2.08 | 1.00 | 2.10 | 2.44 | 2.39 | 2.29 | 2.58 | 0.06 | 3.85 | 3.94 | nd | 0.04 | 0.00 | 3.90 | 2.25 | 3.16 |
| 189 | H | 0.45 | 0.40 | 1.42 | 2.39 | 7.44 | 1.60 | 2.71 | 0.60 | 0.45 | 2.04 | 1.95 | nd | 9.04 | 0.00 | 3.08 | 0.97 | 49.83 | 1.11 | 14.16 | 3.31 | 0.53 | 21.53 |
| 190 | K | 0.43 | 0.97 | 1.59 | 1.16 | 7.98 | 1.77 | 0.00 | 0.52 | 1.91 | 3.96 | 3.70 | 1.58 | 0.86 | 1.23 | 2.70 | 4.14 | 9.10 | 1.20 | 1.08 | 3.63 | 3.14 | 1.98 |
| 191 | V | 0.00 | 1.93 | 1.60 | 1.44 | 8.36 | 2.26 | 0.57 | 0.07 | 1.27 | 3.05 | 3.19 | 1.03 | 0.79 | 2.08 | 1.21 | 3.47 | 20.48 | 0.54 | 0.18 | 2.05 | 2.47 | 1.47 |
| 192 | Y | 3.19 | 16.19 | 5.01 | 5.10 | 9.88 | 4.62 | 4.01 | 3.88 | 4.90 | 5.71 | 6.19 | 3.56 | 0.21 | 1.57 | 1.21 | 0.00 | 27.49 | 3.92 | 5.63 | 20.32 | 2.40 | 6.78 |
| 193 | A | 10.89 | 6.83 | 12.40 | 8.11 | 11.83 | 5.27 | 3.43 | 0.00 | nd | nd | nd | 31.40 | 7.70 | 4.42 | 3.85 | nd | nd | 4.56 | 7.00 | nd | nd | 18.86 |
| 194 | C | 0.14 | nd | 6.21 | 4.73 | 8.42 | 18.23 | 13.98 | 0.00 | nd | nd | nd | nd | 11.68 | nd | 65.75 | nd | 21.32 | 2.85 | 7.44 | nd | nd | nd |
| 195 | E | 3.00 | 4.65 | 2.73 | 1.15 | 8.10 | 2.98 | 0.00 | 3.36 | 5.90 | 7.74 | 9.19 | 1.94 | 3.05 | 4.35 | 3.08 | 8.50 | nd | 1.72 | 0.96 | 9.81 | 8.11 | 1.83 |
| 196 | V | 2.06 | nd | 5.35 | 4.92 | 8.76 | 10.81 | 9.66 | 3.35 | 29.32 | 30.37 | 33.72 | 2.33 | 22.03 | 10.42 | 8.17 | nd | nd | 3.23 | 1.57 | nd | nd | 0.00 |
| 197 | T | 0.67 | 1.26 | 1.13 | 0.88 | 8.81 | 1.60 | 0.43 | 0.61 | 2.84 | 3.40 | 4.18 | 2.24 | 1.52 | 0.00 | 1.37 | 3.43 | 33.72 | 1.50 | 1.50 | 2.65 | 3.19 | 2.03 |
| 198 | H | 0.39 | nd | 0.47 | 1.16 | 6.91 | 0.93 | 0.00 | 1.25 | 0.85 | 1.48 | 0.93 | nd | 8.49 | 5.39 | 6.10 | 16.33 | nd | 1.70 | 1.69 | nd | nd | 5.80 |
| 199 | Q | 1.32 | 0.08 | 1.13 | 1.20 | 7.72 | 1.18 | 0.99 | 1.51 | 1.72 | 2.06 | 2.14 | 1.59 | 1.63 | 0.00 | 2.11 | 2.39 | 5.93 | 1.80 | 1.59 | 1.92 | 1.73 | 1.42 |
| 200 | G | nd | nd | nd | 198.84 | 191.34 | nd | nd | 0.00 | nd | nd | nd | nd | nd | 425.59 | nd | nd | nd | 30.10 | nd | nd | nd | nd |
| 201 | L | 2.28 | 2.37 | 2.89 | 3.46 | 8.04 | 2.99 | 2.73 | 2.75 | 6.00 | 6.46 | 6.90 | 22.93 | 0.00 | 1.56 | 0.95 | 19.74 | 46.55 | 3.31 | 2.56 | 16.95 | nd | 9.71 |
| 202 | S | 1.31 | 0.79 | 0.61 | 0.00 | 7.89 | 1.24 | 0.86 | 0.83 | 1.07 | 1.93 | 2.30 | 2.43 | 2.33 | 1.04 | 2.57 | 3.04 | 5.58 | 1.28 | 1.13 | 2.57 | 2.33 | 2.30 |
| 203 | S | 1.48 | 0.78 | 0.45 | 0.00 | 7.85 | 0.98 | 0.70 | 1.38 | 0.95 | 1.81 | 2.07 | 2.07 | 1.19 | 1.22 | 2.35 | 3.02 | 18.54 | 1.47 | 1.25 | 2.35 | 2.24 | 2.11 |
| 204 | P | 2.53 | 2.95 | 2.89 | 2.99 | 8.47 | 3.01 | 2.43 | 2.42 | 3.82 | 4.06 | 4.74 | 2.49 | 3.37 | 1.97 | 3.40 | 4.86 | 8.73 | 1.42 | 0.00 | 4.70 | 3.98 | 2.52 |
| 205 | V | 1.22 | 0.93 | 1.33 | 0.60 | 7.67 | 1.22 | 0.00 | 1.55 | 1.70 | 2.91 | 3.92 | 1.08 | 0.67 | 0.83 | 2.07 | 2.22 | nd | 1.91 | 1.11 | 3.01 | 2.09 | 0.66 |
| 206 | T | 0.49 | 0.59 | 0.73 | 0.35 | 6.76 | 0.76 | 0.40 | 0.56 | 1.51 | 2.08 | 3.02 | 0.49 | 1.09 | 0.41 | 1.30 | 3.01 | 5.48 | 0.99 | 0.00 | 2.50 | 2.19 | 0.74 |
| 207 | K | 1.01 | 2.37 | 1.58 | 2.50 | 7.72 | 2.25 | 1.82 | 1.84 | 16.91 | 4.79 | 17.62 | 20.72 | 0.00 | 0.83 | 1.84 | nd | 22.26 | 2.26 | 1.85 | 22.04 | nd | 6.76 |
| 208 | S | 14.69 | 5.32 | 4.24 | 4.33 | 11.24 | 4.33 | 2.64 | 0.00 | 4.55 | 4.82 | 6.67 | nd | 6.40 | 4.32 | 4.06 | 7.43 | nd | 5.23 | 7.90 | 6.00 | 4.36 | nd |
| 209 | F | 5.28 | 12.89 | 5.14 | 4.97 | 11.35 | 5.63 | 4.64 | 4.49 | 5.47 | 5.35 | 7.47 | 7.76 | 0.51 | 4.67 | 2.29 | 0.00 | 38.61 | 5.80 | 8.36 | nd | 2.43 | 8.56 |
| 210 | H | 2.02 | 2.01 | 1.83 | 0.69 | 8.23 | 1.65 | 0.00 | 1.89 | 2.18 | 4.32 | 4.32 | 1.44 | 1.91 | 1.56 | 3.02 | 3.48 | 11.27 | 2.49 | 2.10 | 3.64 | 2.62 | 2.20 |
| 211 | R | 1.35 | 1.94 | 2.50 | 3.83 | 9.09 | 3.27 | 2.87 | 3.22 | 3.34 | 4.73 | 5.09 | 5.97 | 0.39 | 0.00 | 3.20 | 2.46 | nd | 2.98 | 2.98 | 29.98 | 3.71 | 3.71 |
| 212 | G | 1.86 | 1.41 | 1.41 | 0.20 | 7.86 | 1.75 | 0.00 | 1.08 | 2.59 | 2.67 | 3.85 | 2.32 | 2.13 | 1.39 | 3.34 | 3.72 | 5.37 | 1.97 | 1.74 | 3.67 | 2.84 | 2.68 |
| 213 | E | 2.04 | 2.78 | 1.92 | 0.60 | 8.67 | 2.33 | 0.00 | 2.30 | 2.77 | 3.20 | 5.01 | 2.73 | 2.65 | 3.17 | 3.19 | 4.03 | 41.28 | 2.31 | 2.35 | 3.85 | 3.11 | 2.84 |
| 214 | C | 0.42 | 15.68 | 20.06 | 22.68 | 5.71 | 29.98 | 27.47 | 0.00 | nd | nd | nd | nd | 6.84 | 6.59 | nd | nd | 1.13 | 7.76 | nd | nd | 48.32 |

Figure 14b

| JH Kabat | WT | A | R | N | D | C | Q | E | G | HID | HIE | HSP | I | L | K | M | F | P | S | T | W | Y | V |
|---|---|---|---|---|---|---|---|---|---|---|---|---|---|---|---|---|---|---|---|---|---|---|---|
| 105 | Q | 1.05 | 0.90 | 1.36 | 1.15 | 7.88 | 1.57 | 0.00 | 0.56 | 2.02 | 3.02 | 2.59 | 1.70 | 1.76 | 0.34 | 1.80 | 2.64 | 5.49 | 1.51 | 1.22 | 3.27 | 2.63 | 1.86 |
| 106 | G | nd | nd | nd | nd | 52.91 | nd | nd | 0.00 | nd | nd | nd | nd | nd | nd | nd | nd | nd | 52.36 | nd | nd | nd | nd |
| 107 | T | 1.11 | 12.40 | 3.87 | 2.47 | 6.43 | 7.81 | 9.74 | 1.94 | nd | nd | nd | 3.59 | 8.26 | 6.59 | 7.99 | nd | nd | 1.89 | 0.00 | nd | nd | 8.39 |
| 108 | L | 0.88 | 1.70 | 1.82 | 1.24 | 7.44 | 1.88 | 1.23 | 0.63 | 2.88 | 3.29 | 4.11 | 0.56 | 0.00 | 0.36 | 0.82 | 1.00 | 5.63 | 1.69 | 1.17 | 3.01 | 1.09 | 1.27 |
| 109 | V | 1.98 | 3.92 | 3.65 | 3.25 | 7.67 | 3.03 | 2.74 | 2.57 | 8.03 | 11.83 | 8.38 | 2.58 | 0.00 | 1.06 | 1.08 | 23.48 | 725.17 | 3.27 | 2.04 | nd | 39.13 | 0.28 |
| 110 | T | 1.57 | 2.21 | 1.92 | 1.99 | 7.74 | 2.27 | 1.28 | 2.23 | 3.61 | 3.59 | 5.24 | 0.00 | 2.35 | 0.84 | 1.41 | 2.94 | 18.12 | 2.77 | 1.42 | 1.90 | 11.60 | 0.46 |
| 111 | V | 2.40 | nd | 4.61 | 5.87 | 8.59 | 14.66 | 10.90 | 3.40 | 23.69 | 23.91 | 24.82 | 0.93 | 7.42 | 28.95 | 7.87 | nd | 18.52 | 3.85 | 3.60 | nd | nd | 0.00 |
| 112 | S | 1.46 | 2.38 | 1.21 | 0.00 | 7.74 | 2.09 | 1.26 | 2.15 | 3.79 | 3.71 | 5.54 | 10.33 | 15.35 | 2.19 | 3.14 | 3.09 | 32.30 | 0.75 | 2.48 | 4.37 | 2.89 | 6.40 |
| 113 | S | 0.82 | 0.81 | 0.52 | 0.00 | 7.58 | 0.94 | 0.42 | 0.56 | 1.17 | 1.48 | 2.75 | 1.83 | 1.89 | 1.27 | 2.73 | 3.05 | 5.08 | 1.00 | 1.07 | 2.64 | 2.02 | 1.87 |
| CH1 EU | | | | | | | | | | | | | | | | | | | | | | | |
| 118 | A | 1.27 | 1.79 | 2.24 | 1.14 | 7.78 | 2.21 | 1.79 | 1.56 | 2.01 | 3.77 | 3.48 | 1.45 | 0.56 | 0.77 | 2.70 | 3.56 | 15.16 | 3.05 | 0.00 | 2.79 | 3.10 | 1.28 |
| 119 | S | 0.69 | 0.89 | 0.30 | 0.00 | 7.55 | 0.90 | 0.27 | 0.32 | 0.56 | 1.59 | 2.23 | 1.48 | 1.25 | 1.19 | 2.23 | 2.21 | 6.06 | 0.45 | 0.46 | 2.65 | 1.77 | 1.92 |
| 120 | T | 0.43 | 1.31 | 1.31 | 0.48 | 6.52 | 1.64 | 1.01 | 0.50 | 1.59 | 2.51 | 3.22 | 0.69 | 1.33 | 1.76 | 2.61 | 3.09 | 5.26 | 1.02 | 0.00 | 3.03 | 2.36 | 0.06 |
| 121 | K | 1.15 | 0.49 | 1.38 | 1.97 | 7.49 | 1.17 | 1.55 | 1.41 | 1.82 | 2.21 | 2.35 | 1.36 | 0.93 | 0.00 | 1.71 | 2.53 | nd | 1.51 | 1.12 | 3.19 | 1.90 | 1.11 |
| 122 | G | 0.35 | 0.88 | 0.82 | 0.43 | 7.44 | 0.84 | 0.00 | 0.40 | 0.61 | 2.12 | 3.24 | nd | 0.53 | 0.94 | 1.39 | 2.82 | 6.81 | 0.90 | 9.67 | 2.55 | 1.76 | nd |
| 123 | P | 3.27 | 14.55 | 4.71 | 4.99 | 8.51 | 19.71 | 17.91 | 0.00 | 26.14 | 18.65 | 26.88 | nd | 12.19 | 10.29 | 4.61 | nd | 9.48 | 2.84 | 5.42 | nd | nd | 40.21 |
| 124 | S | 0.34 | 1.11 | 1.00 | 0.99 | 7.13 | 1.15 | 0.62 | 0.00 | 1.90 | 2.34 | 3.00 | 8.33 | 0.79 | 0.24 | 1.05 | 2.46 | 19.73 | 1.08 | 0.97 | 1.96 | 1.86 | 3.60 |
| 125 | V | 3.10 | 8.57 | 5.47 | 3.49 | 8.09 | 6.53 | 5.05 | 3.16 | 9.15 | 10.03 | 10.55 | 0.00 | 2.01 | 7.81 | 3.67 | 11.71 | 13.17 | 3.68 | 1.86 | nd | 9.85 | 0.16 |
| 126 | F | 0.15 | 2.37 | 2.32 | 2.03 | 7.64 | 4.38 | 3.37 | 0.00 | 2.97 | 3.12 | 3.82 | 5.07 | 1.22 | 0.01 | 0.58 | 0.75 | 50.58 | 2.04 | 5.52 | nd | 1.14 | 7.46 |
| 127 | P | 1.73 | 4.02 | 2.86 | 1.02 | 8.56 | 2.60 | 0.00 | 2.90 | 8.25 | 8.15 | 12.50 | 1.64 | 1.40 | 2.47 | 2.41 | 9.25 | 6.79 | 2.58 | 2.41 | 8.22 | 4.50 | 2.22 |
| 128 | L | 2.99 | 4.19 | 3.89 | 4.31 | 8.38 | 3.98 | 3.33 | 3.76 | 25.29 | 29.68 | 30.77 | 43.17 | 0.00 | 1.81 | 0.70 | nd | nd | 4.45 | 20.50 | nd | nd | 28.39 |
| 129 | A | 1.88 | 3.80 | 3.02 | 1.92 | 8.40 | 3.37 | 2.60 | 1.58 | 5.30 | 6.02 | 6.73 | 0.44 | 0.00 | 1.30 | 1.38 | 2.60 | 5.45 | 2.76 | 1.87 | 7.25 | 2.37 | 1.28 |
| 130 | P | 3.67 | 26.95 | 9.49 | 2.64 | 9.48 | 7.91 | 6.07 | 0.00 | nd | nd | nd | 6.32 | 33.57 | 10.70 | 11.00 | nd | 7.34 | 3.51 | 1.24 | nd | nd | 4.41 |
| 131 | S | 0.00 | 17.88 | 22.62 | 5.56 | 8.68 | 6.33 | 6.98 | 0.66 | nd | nd | nd | 19.29 | nd | 4.73 | 6.11 | nd | 39.36 | 1.35 | 1.00 | nd | nd | 20.08 |
| 132 | S | 1.79 | 2.85 | 2.11 | 0.00 | 9.02 | 2.23 | 0.18 | 1.57 | 2.87 | 3.53 | 5.42 | 2.48 | 2.28 | 3.21 | 3.70 | 4.94 | 9.09 | 2.40 | 1.67 | 4.47 | 3.73 | 2.75 |
| 133 | K | 0.85 | 1.34 | 2.06 | 1.73 | 7.56 | 1.93 | 1.01 | 0.93 | 5.26 | 3.89 | 6.43 | 12.95 | 0.00 | 0.12 | 1.42 | 20.00 | 9.29 | 1.40 | 0.52 | 36.71 | 16.76 | 4.18 |
| 134 | S | 0.00 | nd | 15.77 | 9.88 | 18.45 | 24.31 | 29.15 | 1.46 | nd | nd | nd | nd | nd | nd | nd | nd | 17.31 | 0.30 | 8.54 | nd | nd | nd |
| 135 | T | 0.68 | 1.07 | 1.61 | 1.07 | 7.28 | 1.13 | 0.56 | 0.85 | 8.30 | 7.08 | 9.41 | 0.59 | 0.85 | 1.04 | 1.70 | 4.82 | nd | 0.12 | 0.00 | 5.64 | 3.21 | 2.91 |
| 136 | S | 1.28 | 2.50 | 1.75 | 0.31 | 7.62 | 1.70 | 0.00 | 1.24 | 2.42 | 2.87 | 3.99 | 1.09 | 1.60 | 1.60 | 2.64 | 3.79 | 31.95 | 1.71 | 1.07 | 4.12 | 2.88 | 0.96 |
| 137 | G | 5.38 | 6.12 | 4.41 | 3.72 | 11.86 | 6.13 | 4.76 | 0.00 | 4.75 | 5.88 | 6.30 | 8.48 | 6.75 | 6.83 | 8.00 | 7.25 | nd | 5.52 | 4.99 | 7.20 | 6.24 | 7.90 |
| 138 | G | 0.96 | 1.27 | 0.72 | 0.00 | 7.68 | 1.23 | 0.09 | 0.49 | 1.24 | 1.73 | 2.59 | 1.60 | 1.23 | 1.41 | 2.40 | 2.48 | 5.74 | 1.15 | 1.12 | 2.05 | 1.34 | 2.04 |
| 139 | T | 0.66 | 1.34 | 1.40 | 1.16 | 7.21 | 1.44 | 0.90 | 0.56 | 2.25 | 2.53 | 3.70 | 0.86 | 1.06 | 0.00 | 1.92 | 3.38 | 27.75 | 0.54 | 0.41 | 2.04 | 2.60 | 1.00 |
| 140 | A | 0.00 | nd | 14.80 | 14.00 | 6.65 | nd | nd | 1.48 | nd | nd | nd | nd | nd | nd | nd | nd | nd | 0.78 | 6.42 | nd | nd | 34.33 |
| 141 | A | 0.00 | nd | 8.10 | 7.27 | 7.94 | 12.99 | 13.75 | 1.46 | nd | nd | nd | 50.12 | 17.91 | 11.54 | 10.13 | nd | nd | 1.92 | 5.73 | nd | nd | 22.83 |
| 142 | L | 3.73 | 30.33 | 4.75 | 5.68 | 8.90 | 3.63 | 4.05 | 3.00 | 24.54 | 28.29 | 29.50 | nd | 0.00 | 1.39 | 1.41 | 21.70 | 48.81 | 4.63 | 6.03 | nd | 17.92 | nd |
| 143 | G | nd | nd | nd | nd | 665.20 | nd | nd | 0.00 | nd | nd | nd | nd | nd | nd | nd | nd | nd | nd | nd | nd | nd | nd |
| 144 | C | 0.65 | nd | 2.81 | 4.70 | 5.72 | 14.05 | 8.40 | 0.00 | nd | nd | 33.79 | 32.02 | 32.57 | 27.28 | nd | nd | 2.06 | 1.14 | nd | nd | 8.05 | |
| 145 | L | 1.35 | 5.73 | 3.67 | 3.16 | 8.78 | 3.88 | 2.68 | 1.84 | 5.54 | 5.98 | 7.45 | 31.62 | 0.00 | 1.25 | 1.50 | 1.23 | nd | 2.98 | 3.69 | 24.95 | 1.86 | 24.49 |
| 146 | V | 4.46 | 23.03 | 6.62 | 6.87 | 9.32 | 5.69 | 4.92 | 5.19 | 19.84 | 29.09 | 21.51 | 0.00 | 5.28 | 12.27 | 1.31 | nd | 34.24 | 5.47 | 3.51 | nd | nd | 1.38 |
| 147 | K | 1.93 | 3.19 | 4.04 | 5.75 | 9.62 | 3.99 | 5.23 | 1.82 | 12.86 | 11.19 | 15.04 | 2.74 | 2.03 | 0.00 | 2.53 | 10.35 | 45.47 | 3.13 | 1.81 | 17.86 | 12.70 | 2.96 |
| 148 | D | 3.42 | 5.90 | 3.01 | 0.00 | 9.83 | 4.78 | 0.72 | 3.09 | 5.48 | 5.07 | 8.92 | 9.89 | 6.62 | 6.00 | 5.60 | 5.03 | nd | 3.88 | 7.30 | 5.80 | 4.11 | 11.40 |
| 149 | Y | 6.81 | 11.72 | 5.88 | 6.93 | 11.10 | 5.32 | 3.43 | 1.17 | 4.82 | 6.11 | 7.27 | nd | 2.69 | 2.50 | 0.93 | 0.00 | 15.37 | 5.17 | 3.84 | nd | 1.44 | 23.55 |
| 150 | F | 1.51 | 3.99 | 2.51 | 2.74 | 8.29 | 3.27 | 1.69 | 2.15 | 1.64 | 2.55 | 3.37 | 2.80 | 1.14 | 1.74 | 0.24 | 0.00 | nd | 2.52 | 4.15 | 5.42 | 2.19 | 3.40 |
| 151 | P | 0.00 | 23.45 | 1.20 | 1.01 | 7.35 | 9.92 | 4.09 | 1.61 | 9.59 | 12.43 | 11.07 | 7.62 | 11.43 | 19.06 | 16.90 | 16.32 | 10.05 | 0.55 | 0.72 | nd | 15.15 | 3.50 |
| 152 | E | 1.69 | 2.26 | 1.67 | 1.11 | 7.41 | 2.02 | 0.22 | 2.24 | 4.02 | 3.97 | 5.57 | 1.55 | 0.00 | 1.38 | 0.54 | 5.19 | 7.92 | 2.63 | 2.34 | 3.50 | 4.86 | 2.13 |
| 153 | P | 1.04 | 2.04 | 0.96 | 0.00 | 7.87 | 1.06 | 0.43 | 1.02 | 1.92 | 2.90 | 4.38 | 1.60 | 1.19 | 1.80 | 1.91 | 2.90 | 12.58 | 1.16 | 1.19 | 3.46 | 2.34 | 1.76 |
| 154 | V | 2.03 | 10.11 | 5.36 | 4.54 | 8.79 | 10.16 | 13.11 | 3.55 | nd | nd | nd | 4.39 | 31.59 | 6.25 | 6.16 | nd | 6.59 | 3.45 | 2.03 | nd | nd | 0.00 |
| 155 | T | 1.75 | 3.17 | 1.15 | 0.00 | 9.50 | 1.72 | 0.19 | 1.54 | 2.88 | 2.62 | 4.97 | 2.42 | 2.26 | 2.92 | 3.01 | 3.69 | 27.60 | 2.23 | 2.02 | 1.58 | 2.41 | 3.31 |
| 156 | V | 2.85 | 11.94 | 4.37 | 4.10 | 9.33 | 6.24 | 5.35 | 4.44 | nd | nd | 47.98 | 0.00 | 14.00 | 8.28 | 3.66 | nd | 11.61 | 3.73 | 2.23 | nd | nd | 0.98 |
| 157 | S | 0.28 | 1.20 | 0.80 | 0.37 | 7.24 | 1.16 | 0.43 | 0.00 | 1.63 | 2.14 | 3.17 | 5.73 | 1.32 | 1.11 | 2.30 | 2.73 | 29.92 | 1.00 | 1.12 | 2.58 | 1.76 | 6.18 |
| 158 | W | 2.88 | 9.26 | 5.21 | 6.34 | 10.18 | 5.52 | 5.38 | 6.01 | 6.33 | 5.96 | 5.86 | 3.11 | 1.85 | 1.82 | 2.46 | 2.36 | nd | 4.77 | 4.79 | 0.00 | 6.12 | 4.50 |
| 159 | N | 2.11 | 1.76 | 1.88 | 1.88 | 8.02 | 2.73 | 2.22 | 2.49 | 3.82 | 4.34 | 5.12 | 1.77 | 0.00 | 0.95 | 1.94 | 4.96 | nd | 3.21 | 3.33 | 4.01 | 3.81 | 2.28 |
| 160 | S | 0.43 | 0.67 | 0.71 | 0.40 | 7.26 | 1.11 | 0.82 | 0.00 | 1.18 | 2.02 | 2.47 | 1.87 | 1.57 | 0.59 | 2.13 | 2.87 | nd | 0.94 | 1.09 | 2.12 | 1.61 | 1.62 |
| 161 | G | 13.15 | 4.89 | 3.92 | 4.36 | 13.99 | 5.08 | 4.17 | 0.00 | 6.03 | 6.43 | 7.33 | 14.01 | 6.13 | 5.06 | 8.22 | 9.16 | nd | 10.22 | 7.16 | 8.53 | 7.88 | 12.04 |
| 162 | A | 0.14 | 0.26 | 0.02 | 0.00 | 6.97 | 0.64 | 0.52 | 0.09 | 0.88 | 1.18 | 1.63 | 1.54 | 1.09 | 0.70 | 1.89 | 2.16 | nd | 0.58 | 0.64 | 1.54 | 1.28 | 1.46 |
| 163 | L | 1.50 | 1.69 | 2.45 | 2.92 | 7.96 | 2.60 | 2.48 | 1.91 | 2.77 | 4.21 | 3.96 | 0.54 | 0.00 | 0.31 | 1.79 | 3.11 | nd | 2.65 | 1.96 | 11.77 | 3.55 | 1.43 |

Figure 14b (continued)

| CH1 EU | WT | A | R | N | D | C | Q | E | G | HID | HIE | HSP | I | L | K | M | F | P | S | T | W | Y | V |
|---|---|---|---|---|---|---|---|---|---|---|---|---|---|---|---|---|---|---|---|---|---|---|---|
| 164 | T | 0.81 | 0.00 | 0.57 | 0.23 | 7.28 | 0.90 | 0.20 | 0.47 | 1.22 | 1.59 | 2.24 | 1.52 | 1.62 | 0.71 | 2.36 | 2.73 | 5.85 | 1.11 | 0.72 | 2.03 | 1.90 | 1.61 |
| 165 | S | 0.53 | 0.44 | 0.02 | 0.00 | 7.37 | 0.71 | 0.08 | 0.08 | 0.90 | 1.39 | 2.07 | 1.61 | 1.03 | 0.86 | 2.00 | 2.36 | 4.78 | 0.59 | 0.57 | 1.10 | 1.78 | 1.61 |
| 166 | G | 13.68 | 10.22 | 11.84 | 9.64 | 17.74 | 11.45 | 11.31 | 0.00 | 10.98 | 11.91 | 11.61 | nd | 31.43 | 9.33 | 11.32 | 12.91 | nd | 11.80 | 65.35 | 13.92 | 11.63 | nd |
| 167 | V | 1.66 | 3.04 | 2.73 | 3.70 | 7.40 | 3.11 | 3.74 | 1.78 | 4.71 | 4.71 | 5.10 | 3.70 | 4.86 | 2.34 | 2.54 | 4.63 | nd | 2.85 | 1.75 | 3.88 | 3.28 | 0.00 |
| 168 | H | 0.90 | 1.45 | 2.66 | 3.13 | 8.99 | 3.11 | 4.07 | 1.63 | 3.07 | 4.63 | 4.10 | 3.01 | 1.37 | 0.00 | 1.80 | 4.78 | nd | 2.34 | 4.72 | 5.90 | 5.26 | 4.25 |
| 169 | T | 2.65 | 2.77 | 3.05 | 2.81 | 8.67 | 2.54 | 2.20 | 2.13 | 4.22 | 4.69 | 5.57 | 2.34 | 0.99 | 1.59 | 2.23 | 5.51 | 7.89 | 1.00 | 0.00 | 4.92 | 4.68 | 2.73 |
| 170 | F | 3.68 | 14.99 | 4.85 | 5.07 | 10.22 | 5.08 | 4.33 | 4.36 | 4.47 | 5.20 | 4.63 | 9.86 | 0.00 | 1.65 | 1.61 | 0.61 | 15.48 | 1.44 | 0.50 | nd | 6.90 | 8.56 |
| 171 | P | 0.59 | 1.69 | 1.60 | 2.36 | 8.04 | 2.47 | 2.53 | 0.32 | 1.02 | 2.95 | 1.36 | 2.02 | 1.49 | 0.00 | 2.96 | 3.09 | 9.02 | 1.32 | 1.56 | 3.56 | 3.33 | 2.34 |
| 172 | A | 0.00 | 1.79 | 4.37 | 3.82 | 7.97 | 2.66 | 3.58 | 0.80 | 36.88 | 36.04 | 38.87 | nd | 1.66 | 0.84 | 2.00 | 36.39 | 6.27 | 2.52 | 6.07 | 34.99 | 35.28 | nd |
| 173 | V | 1.63 | 1.42 | 2.32 | 3.22 | 8.72 | 2.75 | 3.82 | 1.28 | 2.68 | 4.41 | 2.48 | 0.44 | 0.50 | 0.00 | 2.15 | 4.11 | 22.02 | 2.58 | 1.41 | 5.33 | 4.09 | 1.08 |
| 174 | L | 0.90 | 0.97 | 1.23 | 1.25 | 7.59 | 1.72 | 1.48 | 0.66 | 2.07 | 2.53 | 3.19 | 0.70 | 0.53 | 0.00 | 1.06 | 3.45 | 6.50 | 1.51 | 1.19 | 3.54 | 2.76 | 1.74 |
| 175 | Q | 1.86 | 4.33 | 0.99 | 0.00 | 8.61 | 2.80 | 0.75 | 2.00 | 4.03 | 5.05 | 5.93 | 3.29 | 1.43 | 1.86 | 1.62 | 3.69 | 21.33 | 1.52 | 1.12 | 4.34 | 4.22 | 2.23 |
| 176 | S | 0.72 | 0.43 | 0.14 | 0.04 | 7.64 | 0.56 | 0.24 | 0.00 | 1.02 | 1.44 | 2.18 | 1.99 | 1.95 | 1.21 | 2.78 | 2.84 | 6.08 | 0.62 | 0.54 | 2.09 | 2.14 | 1.97 |
| 177 | S | 0.39 | 0.52 | 0.24 | 0.05 | 6.26 | 0.48 | 0.00 | 0.36 | 0.83 | 1.32 | 2.12 | 0.95 | 1.63 | 1.02 | 2.07 | 2.54 | 8.03 | 0.68 | 0.29 | 2.18 | 1.48 | 0.57 |
| 178 | G | 24.43 | 12.11 | 10.70 | 10.08 | 18.70 | 11.46 | 11.30 | 0.00 | 10.78 | 11.21 | 11.98 | 22.85 | 10.69 | 10.03 | 12.45 | 19.74 | nd | 17.26 | 13.29 | 20.21 | 16.99 | 21.76 |
| 179 | L | 0.87 | 2.07 | 2.84 | 1.53 | 8.28 | 3.16 | 2.11 | 1.61 | 2.22 | 3.52 | 4.94 | 8.66 | 0.00 | 0.87 | 1.32 | 2.68 | 24.11 | 1.73 | 0.38 | 7.68 | 1.86 | 4.77 |
| 180 | Y | 2.66 | 1.94 | 3.52 | 3.94 | 9.76 | 3.48 | 3.59 | 5.00 | 3.14 | 3.77 | 4.23 | nd | 0.54 | 0.00 | 1.12 | 0.60 | 26.05 | 3.97 | 5.74 | 0.43 | 0.48 | nd |
| 181 | S | 0.52 | 4.85 | 3.14 | 2.32 | 7.35 | 4.19 | 1.41 | 1.58 | 7.94 | 8.31 | 9.64 | 3.12 | 4.22 | 0.17 | 0.00 | 5.62 | nd | 2.20 | 1.38 | 74.15 | nd | 0.90 |
| 182 | L | 2.50 | 8.91 | 4.07 | 5.68 | 9.62 | 3.76 | 3.67 | 2.14 | 9.43 | 10.71 | 10.24 | nd | 0.00 | 0.37 | 1.96 | 6.52 | 30.18 | 3.26 | 3.59 | nd | 17.07 | 55.42 |
| 183 | S | 1.72 | 11.72 | 3.63 | 2.27 | 7.79 | 4.51 | 4.17 | 2.29 | 56.21 | nd | nd | 1.71 | 7.62 | 3.77 | 1.67 | nd | 5.71 | 1.91 | 0.00 | nd | nd | 0.47 |
| 184 | S | 1.28 | nd | 6.21 | 5.03 | 7.19 | 10.05 | 9.93 | 2.47 | nd | nd | nd | 20.81 | nd | 23.74 | nd | nd | 26.46 | 0.00 | 2.20 | nd | nd | 10.57 |
| 185 | V | 2.70 | 8.88 | 4.41 | 4.34 | 8.71 | 4.07 | 3.76 | 3.22 | 14.04 | 15.18 | 16.00 | 0.00 | 13.52 | 2.66 | 1.88 | 16.89 | 17.78 | 4.15 | 2.59 | nd | 27.23 | 0.59 |
| 186 | V | 2.18 | 40.58 | 3.54 | 4.12 | 7.49 | 3.53 | 3.93 | 3.07 | 47.97 | nd | nd | 2.39 | 0.63 | 6.35 | 0.53 | nd | 27.89 | 3.45 | 1.45 | nd | nd | 0.00 |
| 187 | T | 1.51 | 2.22 | 2.49 | 2.49 | 7.76 | 2.84 | 2.63 | 1.65 | 4.14 | 5.18 | 5.29 | 0.67 | 0.72 | 1.09 | 0.00 | 7.32 | nd | 2.56 | 1.38 | 4.99 | 3.20 | 0.94 |
| 188 | V | 2.76 | 1.21 | 2.68 | 3.56 | 7.87 | 2.01 | 2.46 | 2.76 | 13.70 | 14.92 | 14.81 | 0.00 | 2.07 | 0.60 | 1.86 | nd | 20.48 | 3.72 | 2.11 | nd | nd | 0.40 |
| 189 | P | 3.32 | 2.85 | 0.83 | 0.00 | 9.27 | 3.24 | 1.69 | 2.08 | 3.77 | 4.51 | 5.04 | 3.00 | 3.02 | 3.40 | 4.79 | 5.86 | 8.21 | 2.69 | 2.81 | 5.63 | 4.92 | 3.30 |
| 190 | S | 1.09 | 1.44 | 1.25 | 1.26 | 7.41 | 1.57 | 1.01 | 1.49 | 1.84 | 2.59 | 3.44 | 1.11 | 1.39 | 1.36 | 2.33 | 2.73 | nd | 0.42 | 0.00 | 3.08 | 2.07 | 1.09 |
| 191 | S | 0.52 | 0.21 | 0.19 | 0.00 | 6.95 | 0.63 | 0.19 | 0.09 | 1.15 | 1.52 | 2.51 | 1.45 | 1.47 | 0.68 | 2.07 | 2.94 | 5.72 | 0.73 | 0.43 | 1.40 | 1.50 | 1.41 |
| 192 | S | 0.00 | 0.33 | 1.16 | 0.93 | 7.19 | 1.58 | 0.98 | 0.61 | 0.73 | 2.13 | 1.64 | 5.17 | 0.66 | 1.02 | 2.37 | 2.09 | nd | 0.80 | 3.57 | 1.76 | 1.26 | 6.63 |
| 193 | L | 0.87 | 2.41 | 2.37 | 2.60 | 7.53 | 2.32 | 2.00 | 0.36 | 6.34 | 6.79 | 7.50 | 0.71 | 0.00 | 0.60 | 1.26 | 6.67 | nd | 1.78 | 0.86 | 6.83 | 4.42 | 0.88 |
| 194 | G | 0.57 | 0.00 | 0.21 | 0.07 | 7.56 | 0.56 | 0.41 | 0.13 | 0.69 | 1.23 | 2.28 | 1.21 | 1.27 | 0.37 | 1.89 | 2.01 | 5.96 | 0.75 | 0.42 | 0.99 | 1.52 | 1.45 |
| 195 | T | 0.79 | 0.34 | 0.82 | 0.82 | 7.63 | 1.12 | 1.12 | 0.57 | 1.35 | 1.89 | 2.40 | 2.16 | 2.02 | 1.18 | 2.82 | 3.07 | 12.41 | 0.61 | 0.00 | 2.53 | 2.32 | 1.90 |
| 196 | D | 0.70 | 0.00 | 0.50 | 0.00 | 6.98 | 0.49 | 0.04 | 1.25 | 2.01 | 2.22 | 2.95 | 0.49 | 1.05 | 0.38 | 1.13 | 2.71 | nd | 1.15 | 0.05 | 2.87 | 1.94 | 0.22 |
| 197 | T | 0.34 | 0.75 | 0.72 | 0.03 | 7.49 | 1.01 | 0.00 | 0.32 | 1.33 | 1.99 | 2.81 | 1.19 | 0.90 | 1.11 | 2.23 | 2.26 | 6.43 | 0.97 | 0.42 | 1.73 | 1.40 | 1.15 |
| 198 | Y | 1.81 | 3.43 | 3.22 | 3.59 | 8.93 | 3.66 | 3.72 | 3.39 | 3.09 | 3.41 | 3.63 | 6.42 | 0.13 | 0.15 | 1.19 | 0.18 | 10.47 | 3.43 | 2.73 | 14.80 | 0.00 | 4.38 |
| 199 | I | 1.36 | 2.21 | 2.30 | 1.53 | 7.44 | 2.47 | 1.74 | 1.57 | 3.05 | 5.16 | 4.94 | 0.32 | 1.74 | 1.08 | 2.48 | 6.47 | 9.37 | 1.83 | 0.75 | 9.33 | 3.47 | 0.00 |
| 200 | C | 1.07 | nd | 6.63 | 7.18 | 9.74 | 8.20 | 5.93 | 0.00 | nd | nd | nd | nd | nd | 31.72 | 30.43 | nd | nd | 2.29 | 22.55 | nd | nd | nd |
| 201 | H | 1.43 | 1.65 | 1.97 | 1.65 | 7.98 | 2.63 | 1.08 | 1.44 | 2.28 | 2.90 | 4.18 | 0.59 | 0.00 | 0.59 | 0.34 | 2.04 | 19.85 | 1.59 | 1.34 | 3.23 | 2.11 | 1.43 |
| 202 | V | 2.26 | 26.70 | 4.75 | 4.27 | 8.48 | 3.92 | 3.13 | 3.70 | 18.57 | 17.69 | 17.40 | 3.52 | 6.88 | 25.35 | 1.27 | nd | 18.94 | 4.07 | 2.11 | nd | nd | 0.00 |
| 203 | H | 2.90 | 3.79 | 2.32 | 0.59 | 9.39 | 2.18 | 0.00 | 2.27 | 4.12 | 4.81 | 7.01 | 2.38 | 2.27 | 3.38 | 3.42 | 3.63 | nd | 3.09 | 2.40 | 4.86 | 3.21 | 3.86 |
| 204 | H | 0.53 | nd | 0.78 | 0.00 | 8.86 | 7.23 | 4.20 | 1.98 | 7.94 | 2.53 | 8.79 | 14.40 | 4.02 | 8.98 | 1.26 | 17.59 | nd | 2.48 | 1.80 | nd | nd | 18.71 |
| 205 | N | 0.38 | 1.20 | 0.61 | 0.22 | 8.15 | 1.32 | 0.74 | 0.00 | 1.77 | 1.98 | 3.93 | 1.89 | 1.45 | 0.94 | 2.42 | 3.30 | 7.69 | 1.02 | 0.98 | 2.69 | 2.41 | 2.31 |
| 206 | P | 0.00 | 1.93 | 1.03 | 0.50 | 6.42 | 1.14 | 0.11 | 0.37 | 1.92 | 2.66 | 3.56 | nd | 2.01 | 0.65 | 0.44 | 12.49 | 7.33 | 1.32 | 8.25 | nd | 13.32 | nd |
| 207 | S | 0.38 | 1.78 | 1.62 | 0.42 | 7.19 | 1.66 | 0.77 | 1.30 | 1.89 | 3.90 | 5.04 | 16.24 | 14.26 | 0.49 | 2.17 | 19.01 | 46.15 | 0.00 | 3.02 | 22.31 | 17.39 | 11.64 |
| 208 | H | 1.72 | 1.55 | 1.27 | 0.00 | 9.26 | 1.82 | 0.51 | 0.95 | 2.20 | 2.84 | 4.17 | 2.53 | 2.26 | 1.70 | 3.41 | 4.20 | nd | 1.54 | 1.69 | 4.09 | 3.25 | 2.86 |
| 209 | T | 1.11 | 1.23 | 1.33 | 1.12 | 8.13 | 1.41 | 0.94 | 1.39 | 3.06 | 2.81 | 4.48 | 1.48 | 0.82 | 0.72 | 1.95 | 3.88 | nd | 0.36 | 0.00 | 5.21 | 1.70 | 1.54 |
| 210 | K | 1.35 | 0.43 | 1.38 | 1.49 | 7.85 | 1.68 | 1.33 | 0.77 | 2.13 | 2.55 | 3.20 | 1.49 | 1.64 | 0.00 | 2.25 | 3.15 | 9.24 | 1.41 | 1.14 | 3.43 | 3.00 | 1.67 |
| 211 | V | 1.17 | 0.70 | 0.90 | 1.09 | 7.80 | 1.21 | 0.38 | 1.29 | 1.65 | 2.35 | 3.54 | 0.00 | 0.81 | 0.85 | 2.29 | 1.89 | 37.26 | 1.61 | 0.48 | 3.58 | 1.25 | 0.78 |
| 212 | D | 2.41 | 3.11 | 2.24 | 0.33 | 9.26 | 2.78 | 0.00 | 2.30 | 2.99 | 3.43 | 5.42 | 2.88 | 3.20 | 3.55 | 3.49 | 4.53 | 7.48 | 2.76 | 2.69 | 3.48 | 3.50 | 3.12 |
| 213 | K | 1.83 | 0.91 | 2.16 | 3.40 | 7.66 | 2.14 | 2.67 | 2.44 | 3.62 | 4.53 | 3.74 | 2.48 | 1.03 | 0.00 | 1.97 | nd | nd | 2.56 | 0.92 | 73.41 | nd | 4.42 |
| 214 | K | 2.67 | 0.55 | 2.56 | 3.22 | 8.87 | 2.26 | 2.56 | 2.72 | 2.39 | 3.69 | 3.33 | 2.77 | 2.08 | 0.00 | 2.37 | 3.05 | 7.47 | 3.02 | 2.28 | 3.38 | 3.17 | 2.88 |
| 215 | V | 2.98 | nd | 8.95 | 4.96 | 7.92 | 13.97 | 15.00 | 3.86 | nd | nd | 8.82 | 21.61 | 27.72 | 7.63 | nd | nd | 4.55 | 2.45 | nd | nd | 0.00 | |
| 216 | E | 2.13 | 2.95 | 1.44 | 0.11 | 8.67 | 1.99 | 0.00 | 2.13 | 2.24 | 3.43 | 4.60 | 2.71 | 1.79 | 3.08 | 2.83 | 3.64 | 7.60 | 2.18 | 1.79 | 3.22 | 3.25 | 2.68 |
| 217 | P | 1.02 | 1.28 | 1.17 | 0.68 | 7.51 | 1.44 | 0.58 | 0.70 | 1.64 | 2.23 | 3.18 | 0.16 | 1.14 | 0.00 | 0.51 | 1.77 | 7.52 | 1.33 | 0.39 | 1.12 | 1.79 | 0.59 |
| 218 | K | 0.44 | 0.29 | 1.13 | 1.62 | 6.30 | 1.38 | 1.23 | 0.49 | 2.38 | 1.49 | 0.49 | 0.43 | 1.49 | 0.03 | 0.51 | 2.97 | nd | 1.06 | 0.00 | 2.64 | 2.29 | 0.34 |
| 219 | S | 1.23 | 1.65 | 1.11 | 0.21 | 8.19 | 1.48 | 0.00 | 0.83 | 1.70 | 2.22 | 3.52 | 2.32 | 1.84 | 1.58 | 2.75 | 3.48 | 6.42 | 1.48 | 1.48 | 2.64 | 2.80 | 2.65 |
| 220 | C | 2.16 | 44.27 | 4.53 | 4.37 | 8.45 | 19.25 | 18.64 | 0.00 | nd | 17.04 | nd | nd | nd | 33.09 | 39.75 | nd | nd | 1.66 | 4.42 | nd | nd | 34.29 |

Figure 15a

| JH | | | | | | | | | | | Jκ | | | | | | | | | | Jλ | | | | | | |
|---|---|---|---|---|---|---|---|---|---|---|---|---|---|---|---|---|---|---|---|---|---|---|---|---|---|---|---|
| Kabat | Cam | J1 | J2 | J3 | J4 | J5 | J6 | antgn | core | CH1 iface | Substitutions | Kabat | Cam | J1 | J2 | J3 | J4 | J5 | antgn | core | Cκ iface | Substitutions | J1 | J2 | J3 | J4 | J5 | J6 | J7 |
| | | | | | | Y | | | | | | | | | | | | | | | | | | | | | | | |
| | | | | | | Y | | | | | | | | | | | | | | | | | | | | | | | |
| | | | | | | Y | | | | | | | | | | | | | | | | | | | | | | | |
| | A | Y | | | | Y | | | | | | | | | | | | | | | | | | | | | | | |
| | E | W | | | N | Y | | | | | | | | | | | | | | | | | | | | | | | |
| | Y | Y | A | Y | W | G | a | | | | | | | | | | | | | | | | | | | | | | |
| | F | F | F | F | F | M | a | | | | | | | | | | | | | | | | | | | | | | |
| | Q | D | D | D | D | D | a | | | | | 96 | | W | Y | F | L | I | a | | | | Y | V | V | F | W | N | A |
| 102 | Y | H | L | V | Y | S | V | | | | L | 97 | | T | T | T | T | T | a | | | | V | V | V | V | V | V | V |
| 103 | W | W | W | W | W | W | W | a | | | | 98 | | F | F | F | F | F | a | | | | F | F | F | F | F | F | F |
| 104 | G | G | G | G | G | G | G | | c | | | 99 | | G | G | G | G | G | | c | | | G | G | G | G | G | G | G |
| 105 | Q | Q | R | Q | Q | Q | Q | | | | REL | 100 | Q | Q | Q | P | G | Q | | | | PGK | T | G | G | G | E | S | G |
| 106 | G | G | G | G | G | G | G | | c | | | 101 | G | G | G | G | G | G | | c | | | G | G | G | G | G | G | G |
| 107 | S | T | T | T | T | T | T | | c | | T | 102 | T | T | T | T | T | T | | c | | | T | T | T | T | T | T | T |
| 108 | L | L | L | M | L | L | T | | | i | TEK | 103 | K | K | K | K | K | R | | | | RDL | K | K | K | Q | E | K | Q |
| 109 | V | V | V | V | V | V | V | | c | | | 104 | V | V | L | V | V | L | | c | | | V | L | L | L | L | V | L |
| 110 | T | T | T | T | T | T | T | | | i | KEI | 105 | E | E | E | D | E | E | | | i | DKI | T | T | T | I | T | T | T |
| 111 | V | V | V | V | V | V | V | | c | | | 106 | I | I | I | I | I | I | | | i | L | V | V | V | I | V | V | V |
| 112 | S | S | S | S | S | S | S | | | | DKY | 107 | K | K | K | K | K | K | | | | EL | L | L | L | L | L | L | L |
| 113 | S | S | S | S | S | S | S | | | | DRL | | | | | | | | | | | | | | | | | | |

Figure 15b

| EU | IgG1 CH1 | IgG2 CH1 | IgG3 CH1 | IgG4 CH1 | VH iface | CL iface | Core | Substitutions | EU | CL kappa | CL lambda | VL iface | CH1 iface | Core | Substitutions |
|---|---|---|---|---|---|---|---|---|---|---|---|---|---|---|---|
| 118 | A | A | A | A | i | | | KEY | 108 | R | Q | i | | | QDI |
| 119 | S | S | S | S | i | | | REY | 109 | T | P | | | | PRD |
| 120 | T | T | T | T | i | | | REI | 110 | V | K | | | | KEI |
| 121 | K | K | K | K | | | | EYH | 111 | A | A | | | | KEL |
| 122 | G | G | G | G | | | | ER | 112 | A | A | | | | REY |
| 123 | P | P | P | P | | | c | | 113 | P | P | | | c | |
| 124 | S | S | S | S | | | | KEY | 114 | S | S | | i | | DKI |
| 125 | V | V | V | V | | | c | | 115 | V | V | | | c | |
| 126 | F | F | F | F | i | | | KD | 116 | F | T | | i | | T |
| 127 | P | P | P | P | i | c | | | 117 | I | L | | | c | |
| 128 | L | L | L | L | i | | | | 118 | F | F | | i | | |
| 129 | A | A | A | A | i | | | LD | 119 | P | P | | i | c | |
| 130 | P | P | P | P | | | c | | 120 | P | P | | | c | |
| 131 | S | C | C | C | i | | | GT | 121 | S | S | | i | | D |
| 132 | S | S | S | S | | | | DRL | 122 | D | S | | | | SRY |
| 133 | K | R | R | R | | | | REL | 123 | E | E | | i | | RL |
| 134 | S | S | S | S | i | | | | 124 | Q | E | | i | | E |
| 135 | T | T | T | T | | | | IEK | 125 | L | L | | | c | EK |
| 136 | S | S | S | S | i | | | EKI | 126 | K | Q | | | | QDL |
| 137 | G | E | G | E | | | | E | 127 | S | A | | | | ADK |
| 138 | G | S | G | S | | | | SRD | 128 | G | N | | | | N |
| 139 | T | T | T | T | i | | | IEK | 129 | T | K | | i | | KEI |
| 140 | A | A | A | A | | | c | | 130 | A | A | | | c | |
| 141 | A | A | A | A | i | | | | 131 | S | T | | i | | T |
| 142 | L | L | L | L | | | c | | 132 | V | L | | | c | |
| 143 | G | G | G | G | | | | | 133 | V | V | | i | | |
| 144 | C | C | C | C | | | c | | 134 | C | C | | | c | |
| 145 | L | L | L | L | i | | | | 135 | L | L | | i | | |
| 146 | V | V | V | V | | | c | | 136 | L | I | | | c | |
| 147 | K | K | K | K | i | | | AE | 137 | N | S | | i | | SK |
| 148 | D | D | D | D | | | | YK | 138 | N | D | | i | | DKL |
| 149 | Y | Y | Y | Y | | | c | | 139 | F | F | | | c | |
| 150 | F | F | F | F | i | | | LKE | 140 | Y | Y | i | | | KEH |
| 151 | P | P | P | P | i | | | AD | 141 | P | P | i | | | KE |
| 152 | E | E | E | E | i | | | LK | 142 | R | G | i | | | GLD |
| 153 | P | P | P | P | i | | | LD | 143 | E | A | i | | | ARL |
| 154 | V | V | V | V | | | c | | 144 | A | V | | | | |
| 155 | T | T | T | T | | | | EKI | 145 | K | T | | | | TDY |
| 156 | V | V | V | V | | | c | | 146 | V | V | | | c | |
| 157 | S | S | S | S | | | | EKY | 147 | Q | A | | | | AEK |
| 158 | W | W | W | W | | | c | | 148 | W | W | | | c | |
| 159 | N | N | N | N | | | | KDL | 149 | K | K | | | | DY |
| | | | | | | | | | 150 | V | A | | | c | A |
| 160 | S | S | S | S | | | | KEY | 151 | D | D | | | | KI |
| 161 | G | G | G | G | | | | D | 152 | N | S | | | | SRL |
| 162 | A | A | A | A | | | | DKY | 153 | A | S | | | | SDH |
| | | | | | | | | | | | P | | | | |
| 163 | L | L | L | L | | c | | R | 154 | L | V | | | | VER |
| 164 | T | T | T | T | | | | REY | 155 | Q | K | | | | KEI |
| 165 | S | S | S | S | | | | DRY | 156 | S | A | | | | ADR |
| 166 | G | G | G | G | | | | D | 157 | G | G | | | | N |
| 167 | V | V | V | V | | c | | A | 158 | N | | | | | RDL |
| 168 | H | H | H | H | i | | | L | 159 | S | | | | | KEL |
| 169 | T | T | T | T | | c | | E | 160 | Q | V | | i | | VK |

Figure 15b (continued)

| EU | IgG1 CH1 | IgG2 CH1 | IgG3 CH1 | IgG4 CH1 | VH iface | CL iface | Core | Substitutions | EU | CL kappa | CL lambda | VL iface | CH1 iface | Core | Substitutions |
|---|---|---|---|---|---|---|---|---|---|---|---|---|---|---|---|
| 170 | F | F | F | F |   | i |   |   | 161 | E | E |   |   |   | KL |
| 171 | P | P | P | P |   | i |   | GH | 162 | S | T |   | i |   | T |
| 172 | A | A | A | A |   |   |   | KLE | 163 | V | T |   |   |   | TKE |
| 173 | V | V | V | V |   | i |   | TD | 164 | T | T |   | i |   | Q |
| 174 | L | L | L | L |   |   |   | EKY | 165 | E | P | i |   |   | PKY |
| 175 | Q | Q | Q | Q |   | i |   | DL | 166 | Q | S | i |   |   | SEM |
| 176 | S | S | S | S |   |   |   | DRL | 167 | D | K |   |   |   | KL |
| 177 | S | S | S | S |   |   |   | REY | 168 | S | Q | i |   |   | QKY |
|   |   |   |   |   |   |   |   |   | 169 | K | S | i |   |   | SHD |
|   |   |   |   |   |   |   |   |   | 170 | D | N |   |   |   | NRI |
|   |   |   |   |   |   |   |   |   | 171 | S | N | i |   |   | NAV |
| 178 | G | G | G | G |   |   |   | D | 172 | T | K |   |   |   | KIE |
| 179 | L | L | L | L |   |   |   | KYE | 173 | Y | Y | i |   |   | KQL |
| 180 | Y | Y | Y | Y | i |   |   | KLE | 174 | S | A |   | i |   | A |
| 181 | S | S | S | S | i |   |   |   | 175 | L | A |   |   | c |   |
| 182 | L | L | L | L |   |   | c |   | 176 | S | S |   | i |   | T |
| 183 | S | S | S | S |   | i |   | T | 177 | S | S |   |   | c |   |
| 184 | S | S | S | S |   |   | c |   | 178 | T | Y |   | i |   |   |
| 185 | V | V | V | V |   | i |   |   | 179 | L | L |   |   | c |   |
| 186 | V | V | V | V |   |   | c |   | 180 | T | S |   | i |   | SKE |
| 187 | T | T | T | T |   | i |   | IKE | 181 | L | L |   |   | c | K |
| 188 | V | V | V | V |   |   | c | I | 182 | S | T |   |   |   | TER |
| 189 | P | P | P | P |   |   |   | DG | 183 | K | P |   |   |   | PDL |
| 190 | S | S | S | S |   |   |   | IKE | 184 | A | E |   |   |   | EKY |
| 191 | S | S | S | S |   |   |   | DRY | 185 | D | Q |   |   |   | QRI |
| 192 | S | N | S | S |   |   |   | NRL | 186 | Y | W |   |   | c |   |
| 193 | L | F | L | L |   |   | c | FE | 187 | E | K |   |   |   | KY |
| 194 | G | G | G | G |   |   |   | RD | 188 | K | S |   |   |   | SEY |
| 195 | T | T | T | T |   |   |   | RDY | 189 | H | H |   |   |   | DKY |
| 196 | Q | Q | Q | K |   |   |   | KDL | 190 | K | R |   |   |   | REL |
| 197 | T | T | T | T |   |   |   | REY | 191 | V | S |   |   |   | SER |
| 198 | Y | Y | Y | Y |   |   | c | L | 192 | Y | Y |   |   | c |   |
| 199 | I | T | T | T |   |   |   | TDK | 193 | A | S |   |   |   | SEK |
| 200 | C | C | C | C |   |   | c |   | 194 | C | C |   |   | c |   |
| 201 | N | N | N | N |   |   |   | EKL | 195 | E | Q |   |   |   | QKI |
| 202 | V | V | V | V | i |   | c |   | 196 | V | V |   |   | c |   |
| 203 | N | D | N | D |   |   |   | DLK | 197 | T | T |   |   |   | EKL |
| 204 | H | H | H | H |   |   | c |   | 198 | H | H |   |   | c |   |
| 205 | K | K | K | K |   |   |   | DL(A) | 199 | Q | E |   |   |   | EKY |
| 206 | P | P | P | P |   |   |   | AE | 200 | G | G |   |   |   | S |
| 207 | S | S | S | S |   |   | c | KD | 201 | L |   |   |   | c |   |
| 208 | N | N | N | N |   |   |   | REY | 202 | S |   |   |   |   | DRY |
| 209 | T | T | T | T |   |   |   | EKY | 203 | S | S |   |   |   | DRL |
| 210 | K | K | K | K |   |   |   | LEY(A) | 204 | P | T |   |   |   | T |
| 211 | V | V | V | V |   |   |   | REY | 205 | V | V |   |   | c | EK |
| 212 | D | D | D | D |   |   |   | QKHLY | 206 | T | E |   |   |   | EKI |
| 213 | K | K | K | K |   | i |   | NEHLY(A) | 207 | K | K |   | i |   | EL(A) |
| 214 | K | T | R | R |   |   |   | NEHLY(A) | 208 | S | T |   |   |   | TEK |
| 215 | V | V | V | V |   |   | c |   | 209 | F | V |   | i | c |   |
| 216 | E | E | E | E |   |   |   | NKHLY | 210 | N | A |   |   |   | AEK |
| 217 | P | R | L | S |   |   |   | DHAVG | 211 | R | P |   |   | c | PE(A) |
| 218 | K | K | K | K |   | i |   | DEQTHLY(A) | 212 | G | T |   |   |   | TKE |
| 219 | S | C | T | Y |   |   |   | DEQKTHLIY | 213 | E | E |   |   |   | RL |
| 220 | C | C | P | G |   |   |   |   | 214 | C | C |   |   |   |   |

IMMUNOGLOBULIN VARIANTS OUTSIDE THE FC REGION

The present invention claims the benefit of priority under 35 U.S.C § 119(e) to the following U.S. Provisional Application Ser. Nos. U.S. Ser. No. 60/556,353, filed Mar. 24, 2004; U.S. Ser. No. 60/573,302, filed May 21, 2004; U.S. Ser. No. 60/585,328, filed Jul. 1, 2004; U.S. Ser. No. 60/586,837, filed Jul. 9, 2004; U.S. Ser. No. 60/599,741, filed Aug. 6, 2004; U.S. Ser. No. 60/607,398, filed Sep. 2, 2004; U.S. Ser. No. 60/614,944, filed Sep. 29, 2004; and U.S. Ser. No. 60/619,409, filed, Oct. 14, 2004, all hereby incorporated by reference in their entirety.

FIELD OF THE INVENTION

The present invention relates to novel optimized antibody variants wherein one or more amino acid modifications are made outside the Fc region that alter binding of the antibody to one or more effector ligands, and their application, particularly for therapeutic purposes.

BACKGROUND OF THE INVENTION

Antibodies are immunological proteins that bind a specific antigen. In most mammals, including humans and mice, antibodies are constructed from paired heavy and light polypeptide chains. Each chain is made up of individual immunoglobulin (Ig) domains, and thus the generic term immunoglobulin is used for such proteins. Each chain is made up of two distinct regions, referred to as the variable and constant regions. The light and heavy chain variable regions show significant sequence diversity between antibodies, and are responsible for binding the target antigen. The constant regions show less sequence diversity, and are responsible for binding a number of natural proteins to elicit important biochemical events. In humans there are five different isotypes or classes of antibodies including IgA (which includes subclasses IgA1 and IgA2), IgD, IgE, IgG (which includes subclasses IgG1, IgG2, IgG3, and IgG4), and IgM. The distinguishing features between these antibody isotypes are their constant regions, although subtler differences may exist in the V region. FIG. 1 shows an IgG1 antibody, used here as an example to describe the general structural features of immunoglobulins. IgG antibodies are tetrameric proteins composed of two heavy chains and two light chains. The IgG heavy chain is composed of four immunoglobulin domains linked from N- to C-terminus in the order VH-CH1-CH2-CH3, referring to the heavy chain variable domain, heavy chain constant domain 1, heavy chain constant domain 2, and heavy chain constant domain 3 respectively (also referred to as VH-Cγ1-Cγ2-Cγ3, referring to the heavy chain variable domain, constant gamma 1 domain, constant gamma 2 domain, and constant gamma 3 domain respectively for the IgG class). The IgG light chain is composed of two immunoglobulin domains linked from N- to C-terminus in the order VL-CL, referring to the light chain variable domain and the light chain constant domain respectively.

The variable region of an antibody contains the antigen binding determinants of the molecule, and thus determines the specificity of an antibody for its target antigen. The variable region is so named because it is the most distinct in sequence from other antibodies within the same isotype. The majority of sequence variability occurs in the complementarity determining regions (CDRs). There are 6 CDRs total, three each per heavy and light chain, designated VH CDR1, VH CDR2, VH CDR3, VL CDR1, VL CDR2, and VL CDR3. The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens. A number of high resolution structures are available for a variety of variable region fragments from different organisms, some unbound and some in complex with antigen. The sequence and structural features of antibody variable regions are well characterized (Morea et al., 1997, *Biophys Chem* 68:9-16; Morea et al., 2000, *Methods* 20:267-279), and the conserved features of antibodies have enabled the development of a wealth of antibody engineering techniques (Maynard et al., 2000, *Annu Rev Biomed Eng* 2:339-376). For example, it is possible to graft the CDRs from one antibody, for example a murine antibody, onto the framework region of another antibody, for example a human antibody. This process, referred to in the art as humanization, enables generation of less immunogenic antibody therapeutics from nonhuman antibodies. Fragments comprising the variable region can exist in the absence of other regions of the antibody, including for example the antigen binding fragment (Fab) comprising VH-CH1 and VL-CL, the variable fragment (Fv) comprising VH and VL, the single chain variable fragment (scFv) comprising VH and VL linked together in the same chain, as well as a variety of other variable region fragments (Little et al., 2000, *Immunol Today* 21:364-370).

The Fc region of an antibody interacts with a number of Fc receptors and ligands, imparting an array of important functional capabilities referred to as effector functions. For IgG the Fc region, as shown in FIG. 1, comprises Ig domains CH2 and CH3. An important family of Fc receptors for the IgG isotype are the Fc gamma receptors (FcγRs). These receptors mediate communication between antibodies and the cellular arm of the immune system (Raghavan et al., 1996, *Annu Rev Cell Dev Biol* 12:181-220; Ravetch et al., 2001, *Annu Rev Immunol* 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and γδ T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, *Annu Rev Cell Dev Biol* 12:181-220; Ghetie et al., 2000, *Annu Rev Immunol* 18:739-766; Ravetch et al., 2001, *Annu Rev Immunol* 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). A number of structures have been solved of the extracellular domains of human FcγRs, including FcγRIIa (pdb accession code 1H9V)(Sondermann et al., 2001, *J Mol Biol* 309:737-749) (pdb accession code 1FCG)(Maxwell et al., 1999, *Nat Struct Biol* 6:437-442), FcγRIIb (pdb accession code 2FCB) (Sondermann et al., 1999, *Embo J* 18:1095-1103); and FcγRIIIb (pdb accession code 1E4J)(Sondermann et al., 2000, *Nature* 406:267-273.). All FcγRs bind the same region on Fc, at the N-terminal end of the Cγ2 domain and the preceding hinge, shown in FIG. 2. This interaction is well characterized structurally (Sondermann et al., 2001, *J Mol Biol* 309:737-749), and several structures of the human Fc bound to the extracellular domain of human FcγRIIIb have been solved (pdb accession code 1 E4K) (Sondermann et al., 2000, *Nature* 406:267-273.) (pdb accession codes 1IIS and 1IIX)(Radaev et al., 2001, *J Biol Chem* 276:16469-16477), as well as has the structure of the human IgE Fc/FcεRIα complex (pdb accession code 1F6A)(Garman et al., 2000, *Nature* 406:259-266).

The different IgG subclasses have different affinities for the FcγRs, with IgG1 and IgG3 typically binding substantially better to the receptors than IgG2 and IgG4 (Jefferis et al., 2002, *Immunol Lett* 82:57-65). All FcγRs bind the same region on IgG Fc, yet with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical, however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of IDEC Pharmaceuticals Corporation). Patients with the V158 allotype respond favorably to Rituxan treatment; however, patients with the lower affinity F158 allotype respond poorly (Cartron et al., 2002, *Blood* 99:754-758). Approximately 10-20% of humans are V158/V158 homozygous, 45% are V158/F158 heterozygous, and 35-45% of humans are F158/F158 homozygous (Lehrnbecher et al., 1999, *Blood* 94:4220-4232; Cartron et al., 2002, *Blood* 99:754-758). Thus 80-90% of humans are poor responders, that is they have at least one allele of the F158 FcγRIIIa.

Although IgG is the principal antibody isoform used for therapeutic applications, other isoforms have therapeutic potential. For example, a growing body of evidence suggests that interaction of IgA Fc with its Fc receptor FcαRI (CD89) elicits a plethora of effector functions (Egmond et al., 2001, *Trends in Immunology*, 22: 205-210). IgA is the most prominent isotype of antibodies at mucosal surfaces, and the second most predominant isotype in human serum. A number of recent studies using bispecific antibody fragment constructs that simultaneously target a cancer antigen and FcαRI indicate that engagement of FcαRI can result in cell-mediated tumor cell killing (Stockmeyer et al., 2000, *J. Immunol.* 165: 5954-5961; Stockmeyer et al., 2001, *J. Immunol. Methods* 248: 103-111; Sundarapandiyan et al., 2001, *J. Immunol. Methods* 248: 113-123; dDechant et al., 2002, *Blood* 100: 4574-80; (van Egmond et al., 2001, *Cancer Research* 61: 4055-4060). The structure of the the extracellular domain of FcαRI has recently been solved (Ding et al., 2003, *J. Biol. Chem.* 278: 27966-27970), as has the receptor in complex with IgA Fc (Herr et al., 2003, *Nature* 423: 614-620), and the interface has been characterized with mutagenesis (Wines et al., 1999, *J. Immunol.*, 162: 2146-2153; Wines et al., 2001, *J. Immunol.* 166: 1781-1789). FcαRI binds to IgA Fc at a site between the CH2 and CH3 domains, and thus despite substantial structural homology between gamma and alpha Fc and FcγRs, the IgA/FcαRI interaction is structurally distinct on Fc from the IgG/FcγR interaction.

A site on Fc that is overlapping but separate from the FcγR binding site serves as the interface for the complement protein C1q (shown in FIG. 1). In the same way that Fc/FcγR binding mediates ADCC, Fc/C1q binding mediates complement dependent cytotoxicity (CDC). C1q forms a complex with the serine proteases C1r and C1s to form the C1 complex. C1q is capable of binding six antibodies, although binding to two IgGs is sufficient to activate the complement cascade. Similar to Fc interaction with FcγRs, different IgG subclasses have different affinity for C1q, with IgG1 and IgG3 typically binding substantially better to the FcγRs than IgG2 and IgG4 (Jefferis et al., 2002, *Immunol Lett* 82:57-65). The structure of human C1q has been solved (Gaboriaud et al., 2003, *J Biol Chem* 278:46974-46982). There is currently no structure available for the Fc/C1q complex; however, mutagenesis studies have mapped the binding site on human IgG for C1q to a region involving residues D270, K322, K326, P329, and P331, and E333 (Idusogie et al., 2000, *J Immunol* 164:4178-4184; Idusogie et al., 2001, *J Immunol* 166:2571-2575).

A site on Fc between the CH2 and CH3 domains, shown in FIG. 1, mediates interaction with the neonatal receptor FcRn, the binding of which recycles endocytosed antibody from the endosome back to the bloodstream (Raghavan et al., 1996, *Annu Rev Cell Dev Biol* 12:181-220; Ghetie et al., 2000, *Annu Rev Immunol* 18:739-766). This process, coupled with preclusion of kidney filtration due to the large size of the full length molecule, results in favorable antibody serum half-lives ranging from one to three weeks. Binding of Fc to FcRn also plays a key role in antibody transport. The binding site for FcRn on Fc is also the site at which the bacterial proteins A and G bind. The tight binding by these proteins is typically exploited as a means to purify antibodies by employing protein A or protein G affinity chromatography during protein purification. Thus the fidelity of this region on Fc is important for both the clinical properties of antibodies and their purification. Available structures of the rat Fc/FcRn complex (Martin et al., 2001, *Mol Cell* 7:867-877), and of the complexes of Fc with proteins A and G (Deisenhofer, 1981, *Biochemistry* 20:2361-2370; Sauer-Eriksson et al., 1995, *Structure* 3:265-278; Tashiro et al., 1995, *Curr Opin Struct Biol* 5:471-481) provide insight into the interaction of Fc with these proteins.

A key feature of the Fc region is the conserved N-linked glycosylation that occurs at N297, shown in FIG. 1. This carbohydrate, or oligosaccharide as it is sometimes referred, plays a critical structural and functional role for the antibody, and is one of the principle reasons that antibodies must be produced using mammalian expression systems. The structural purpose of this carbohydrate may be to stabilize or solubilize Fc, determine a specific angle or level of flexibility between the CH3 and CH2 domains, keep the two CH2 domains from aggregating with one another across the central axis, or a combination of these. Efficient Fc binding to FcγR and C1q require this modification, and alterations in the composition of the N297 carbohydrate or its elimination affect binding to these proteins (Umana et al., 1999, *Nat Biotechnol* 17:176-180; Davies et al., 2001, *Biotechnol Bioeng* 74:288-294; Mimura et al., 2001, *J Biol Chem* 276:45539-45547; Radaev et al., 2001, *J Biol Chem* 276: 16478-16483; Shields et al., 2001, *J Biol Chem* 276:6591-6604; Shields et al., 2002, *J Biol Chem* 277:26733-26740; Simmons et al., 2002, *J Immunol Methods* 263:133-147). Yet the carbohydrate makes little if any specific contact with FcγRs (Radaev et al., 2001, *J Biol Chem* 276:16469-16477), indicating that the functional role of the N297 carbohydrate in mediating Fc/Fc□R binding is via the structural role it plays in determining the Fc conformation. This is supported by a collection of crystal structures of four different Fc glycoforms, which show that the composition of the oligosaccharide impacts the conformation of CH2 and as a result the Fc/FcγR interface (Krapp et al., 2003, *J Mol Biol* 325:979-989).

The features of antibodies discussed above—specificity for target, ability to mediate immune effector mechanisms, and long half-life in serum—make antibodies powerful therapeutics. Monoclonal antibodies are used therapeutically for the treatment of a variety of conditions including cancer, inflammation, and cardiovascular disease. There are currently over ten antibody products on the market and hundreds in development. Despite such widespread application, antibodies are not optimized for clinical use. A significant deficiency of antibodies is their suboptimal anticancer potency. This and other shortcomings of antibodies are addressed by the present invention.

There are a number of possible mechanisms by which antibodies destroy tumor cells, including anti-proliferation via blockage of needed growth pathways, intracellular signaling leading to apoptosis, enhanced down regulation and/or turnover of receptors, CDC, ADCC, ADCP, and promotion of an adaptive immune response (Cragg et al., 1999, *Curr Opin Immunol* 11:541-547; Glennie et al., 2000, *Immunol Today* 21:403-410). Anti-tumor efficacy can be due to a combination of these mechanisms, and their relative importance in clinical therapy appears to be cancer dependent. Despite this arsenal of anti-tumor weapons, the potency of antibodies as anti-cancer agents is unsatisfactory, particularly given their high cost. Patient tumor response data show that monoclonal antibodies provide only a small improvement in therapeutic success over normal single-agent cytotoxic chemotherapeutics. For example, just half of all relapsed low-grade non-Hodgkin's lymphoma patients respond to the anti-CD20 antibody Rituxan (McLaughlin et al., 1998, *J Clin Oncol* 16:2825-2833). Of 166 clinical patients, 6% showed a complete response and 42% showed a partial response, with median response duration of approximately 12 months. Trastuzumab (Herceptin®, a registered trademark of Genentech), an anti-HER2/neu antibody for treatment of metastatic breast cancer, has less efficacy. The overall response rate using Herceptin for the 222 patients tested was only 15%, with 8 complete and 26 partial responses and a median response duration and survival of 9 to 13 months (Cobleigh et al., 1999, *J Clin Oncol* 17:2639-2648). Currently for anticancer therapy, any small improvement in mortality rate defines success. Thus there is a significant need to enhance the capacity of antibodies to destroy targeted cancer cells.

A promising means for enhancing the anti-tumor potency of antibodies is via enhancement of their ability to mediate cytotoxic effector functions such as ADCC, ADCP, and CDC. The importance of FcγR-mediated effector functions for the anti-cancer activity of antibodies has been demonstrated in mice (Clynes et al., 1998, *Proc Natl Acad Sci USA* 95:652-656; Clynes et al., 2000, *Nat Med* 6:443-446), and the affinity of interaction between Fc and certain FcγRs correlates with targeted cytotoxicity in cell-based assays (Shields et al., 2001, *J Biol Chem* 276:6591-6604; Presta et al., 2002, *Biochem Soc Trans* 30:487-490; Shields et al., 2002, *J Biol Chem* 277:26733-26740). Additionally, a correlation has been observed between clinical efficacy in humans and their allotype of high (V158) or low (F158) affinity polymorphic forms of FcγRIIIa (Cartron et al., 2002, *Blood* 99:754-758). Together these data suggest that an antibody that is optimized for binding to certain FcγRs may better mediate effector functions and thereby destroy cancer cells more effectively in patients. The balance between activating and inhibiting receptors is an important consideration, and optimal effector function may result from an antibody that has enhanced affinity for activation receptors, for example FcγRI, FcγRIIa/c, and FcγRIIIa, yet reduced affinity for the inhibitory receptor FcγRIIb. Furthermore, because FcγRs can mediate antigen uptake and processing by antigen presenting cells, enhanced FcγR affinity may also improve the capacity of antibody therapeutics to elicit an adaptive immune response. Fc variants have been successfully engineered with selectively enhanced binding to FcγRs, and furthermore these Fc variants provide enhanced potency and efficacy in cell-based effector function assays. See for example U.S. Ser. No. 10/672,280, U.S. Ser. No. 10/822,231, entitled "Optimized Fc Variants and Methods for their Generation", U.S. Ser. No. 60/627,774, entitled "Optimized Fc Variants", and U.S. Ser. No. 60/642,477, entitled "Improved Fc Variants", and references cited therein.

All research on engineering antibodies to enhance effector function has focused on the Fc region because it comprises the binding sites for FcγRs and C1q. The present invention describes the concept that determinants of effector ligand binding and effector function reside not only in the Fc region, but also in the Fab and hinge regions of an antibody. The present invention describes methods by which to generate Fab and hinge variants, and provides a series of novel engineered immunoglobulin variants in the VL, VH, JL, JH, CL, CH1, and hinge regions that provide altered and optimized effector ligand binding properties. Based on the documented relationship described above between affinity and specifity of antibodies for effector ligands, their behavior in cell based effector function assays, and their clinical behavior in vivo, engineered Fab and hinge variants that modulate binding to effector ligands may provide optimal clinical properties.

SUMMARY OF THE INVENTION

The present invention provides antibody variants outside the Fc region that are optimized for a number of therapeutically relevant properties.

It is an object of the present invention to provide an antibody variant, wherein said antibody variant comprises one or more amino acid modifications outside the Fc region of the parent antibody, wherein said modification alters the affinity of said antibody for one or more effector ligands.

In one embodiment, the antibody variant of the present invention comprises one or amino acid modifications at a position in the VL region. In one embodiment, the antibody variant comprises one or amino acid modifications at a position in the JL region. In an alternate embodiment, the antibody variant comprises one or more amino acids at a position in the VH region. In one embodiment, the antibody variant comprises one or more amino acids at a position in the JH region. In an alternate embodiment, the antibody variant comprises one or amino acid modifications at a position in the CL region. In an alternate embodiment, the antibody variant comprises one or more amino acids at a position in the CH1 region. In an alternate embodiment, the antibody variant comprises one or amino acid modifications at a position in the hinge region.

In one embodiment, the antibody variant of the present invention variant binds with greater affinity to one or more effector ligands relative to the parent antibody. The increase in affinity can range from about 1.5, 2 or 3-fold of wild-type (or parent), or greater. In an alternate embodiment, the antibody variant binds with reduced affinity to one or more effector ligands relative to the parent antibody.

In one embodiment, the antibody variant of the present invention binds with greater affinity to one or more FcγRs relative to the parent antibody. In a preferred embodiment, said FcγR is human FcγRIIIa. Additional FcγRs which may have modified (including increases and decreases) binding affinity are shown in the tables. In an alternate embodiment, the antibody variant binds with weaker affinity to one or more FcγRs relative to the parent antibody. In a preferred embodiment, said FcγR is human FcγRIIb. In an alternate embodiment, the antibody variant binds with greater affinity to one or more FcγRs but reduced affinity to one or more other FcγRs relative to the parent antibody.

In one embodiment, the antibody variant of the present invention mediates effector function in the presence of effector cells more effectively than the parent antibody. In one embodiment, the antibody variant mediates ADCC that is greater than that mediated by the parent antibody. In an alternate embodiment, the antibody variant mediates ADCP that is greater than that mediated by the parent antibody. In an alternate embodiment, the antibody variant mediates CDC that is greater than that mediated by the parent antibody.

It is an object of the present invention to provide an antibody variant, wherein said antibody variant comprises one or more substitutions outside the Fc region of the parent antibody, and further comprises one or more substitutions in the Fc region of the parent antibody, wherein said antibody variant has altered affinity for one or more effector ligands; the preferred ligands are outlined above It is an object of the present invention to provide one or more positions in the Fab region of an antibody, wherein mutation at said position alters binding of said antibody to one or more effector ligands. In one embodiment, said position is in the VL region. In one embodiment, said position is in the JL region. In an alternate embodiment, said position is in the VH region. In one embodiment, said position is in the JH region. In an alternate embodiment, said position is in the CL region. In an alternate embodiment, said position is in the CH1 region. It is an object of the present invention to provide one or more substitutions in the Fab region of an antibody, wherein said substitution alters binding of said antibody to one or more effector ligands. In one embodiment, said substitution is in the VL region. In one embodiment, said substitution is in the JL region. In an alternate embodiment, said substitution is in the VH region. In one embodiment, said substitution is in the JH region. In an alternate embodiment, said substitution is in the CL region. In an alternate embodiment, said substitution is in the CH1 region.

It is an additional object of the invention to provide specific positions and specific modifications of non-Fc regions as follows: (all numbering is according to the Kabat numbering scheme, and the parent sequence is human):

JL region modifications: positions 100, 103, 105 and 106, and modifications: Q100P, Q100G, Q100K, K103R, K103D, K103L, E105D, E105K, E105K, E105I, E105I, I106L, and K107E. JH region modifications: positions 110, 112 and 113; modifications: T110I, S112D, S113D, and S113R.

CL region modifications: positions 108, 109, 110, 111, 112, 114, 116, 121, 122, 123, 124, 125, 126, 127, 128, 129, 131, 137, 138, 140, 141, 142, 143, 145, 147, 149, 150, 151, 152, 153, 154, 155, 156, 157, 159, 160, 161, 162, 163, 164, 165, 166, 167, 168, 169, 170, 171, 172, 173, 174, 176, 180, 181, 182, 183, 184, 185, 187, 188, 189, 190, 191, 193, 195, 197, 199, 200, 202, 203, 204, 205, 206, 207, 208, 210, 211, 212, and 213, modifications: R108Q, R108D, R108I, T109P, T109R, T109D, V110K, V110E, V110I, A111K, A111E, A111L, A112R, A112E, A112Y, S114D, S114K, S114I, F116T, S121D, D122S, D122R, D122Y, E123R, E123L, Q124E, L125E, L125K, K126Q, K126D, K126L, S127A, S127D, S 127K, G128N, T129K, T129E, T129I, S131T, N137S, N137K, N138D, N138K, N138L, Y140K, Y140E, Y140H, P141K, P141E, R142G, R142L, R142D, E143A, E143R, E143L, K145T, K145D, K145Y, Q147A, Q 147E, Q147K, K149D, K149Y, V150A, D151K, D151I, N152S, N152R, N152L, A153S, A153D, A153H, L154V, L154E, L154R, Q155K, Q155E, Q155I, S156A, S156D, S156R, G157N, N158R, N158D, N158L, S159K, S159E, S159L, Q160V, Q160K, E161K, E161L, S162T, V163T, V163K, V163E, T164Q, E165P, E165K, E165Y, Q166S, Q166E, Q166M, D167K, D167L, S168Q, S168K, S168Y, K169S, K169H, K169D, D170N, D170R, D170I, S171N, S171A, S171V, T172K, T172I, T172E, Y173K, Y173Q, Y173L, S174A, S176T, T180S, T180K, T180E, L181K, S182T, S182E, S182R, K183P, K183D, K183L, A184E, A184K, A184Y, D185Q, D185R, D185I, E187K, E187Y, K188S, K188E, K188Y, H189D, H189K, H189Y, K190R, K190E, K190L, V191S, V191E, V191R, A193S, A193E, A193K, E195Q, E195K, E195I, T197E, T197K, T197L, Q199E, Q199K, Q199Y, G200S, S202D, S202R, S202Y, S203D, S203R, S203L, P204T, V205E, V205K, T206E, T206K, T206I, K207E, K207L, K207A, S208T, S208E, S208K, N210A, N210E, N210K, R211P, R211E, R211A, G212T, G212K, G212E, E213R, and E213L.

CH regions: positions 118, 119, 120, 121, 122, 124, 126, 129, 131, 132, 133, 135, 136, 137, 138, 139, 147, 148, 150, 151, 152, 153, 155, 157, 159, 160, 161, 162, 163, 164, 165, 166, 167, 168, 169, 171, 172, 173, 174, 175, 176, 177, 178, 179, 180, 183, 187, 188, 189, 190, 191, 192, 193, 194, 195, 196, 197, 198, 199, 201, 203, 205, 206, 207, 208, 209, 210, 211, 212, 213, 214, 216, 217, 218, 219, 221, 222, 223, 224, and 225; modifications: A118K, A118E, A118Y, S119R, S119E, S119Y, T120R, T120E, T120I, K121E, K121Y, K121H, G122E, G122R, S124K, S124E, S124Y, F126K, F126D, A129L, A129D, S131G, S131T, S132D, S132R, S132L, K133R, K133E, K133L, T135I, T135E, T135K, S136E, S136K, S136I, G137E, G138S, G138R, G138D, T139I, T139E, T139K, K147A, K147E, D148Y, D148K, F150L, F150K, F150E, P151A, P151D, E152L, E152K, P153L, P153D, T155E, T155K, T155I, S157E, S157K, S157Y, N159K, N159D, N159L, S160K, S160E, S160Y, G161D, A162D, A162K, A162Y, L163R, T164R, T164E, T164Y, S165D, S165R, S165Y, G166D, V167A, H168L, T169E, P171G, P171H, A172K, A172L, A172E, V173T, V173D, L174E, L174K, L174Y, Q175D, Q175L, S176D, S176R, S176L, S177R, S177E, S177Y, G178D, L179K, L179Y, L179E, Y180K, Y180L, Y180E, S183T, T187I, T187K, T187E, V188I, P189D, P189G, S190I, S190K, S190E, S191D, S191R, S191Y, S192N, S192R, S192L, L193F, L193E, G194R, G194D, T195R, T195D, T195Y, Q196K, Q196D, Q196L, T197R, T197E, T197Y, Y198L, I199T, I199D, I199K, N201E, N201K, N201L, N203D, N203L, N203K, K205D, K205L, K205AP206A, P 206E, S207K, S207D, N208R, N208E, N208Y, T209E, T209K, T209Y, K210L, K210E, K210Y, K210A, V211R, V211E, V211Y, D212Q, D212K, D212H, D212L, D212Y, K213N, K213E, K213H, K213L, K213Y, K213A, K214N, K214E, K214H, K214L, K214Y, K214A, E216N, E216K, E216H, E216L, E216Y, P217D, P217H, P217A, P217V, P217G, K218D, K218E, K218Q, K218T, K218H, K218L, K218Y, K218A, S219D, S219E, S219Q, S219K, S219T, S219H, S219L, S219I, S219Y, D221K, D221Y, D221E, D221N, D221Q, D221R, D221 S, D221T, D221H, D221A, D221V, D221L, D221I, D221F, D221M, D221W, D221P, D221G, K222E, K222Y, K222D, K222N, K222Q, K222R, K222S, K222T, K222H, K222V, K222L, K222I, K222F, K222M, K222W, K222P, K222G, K222A, T223D, T223N, T223Q, T223R, T223S, T223H, T223A, T223V, T223L, T223I, T223F, T223M, T223Y, T223W, T223P, T223G, T223E, T223K, H224D, H224N, H224Q, H224K, H224R, H224S, H224T, H224V, H224L, H224I, H224F, H224M, H224W, H224P, H224G, H224E, H224Y, H224A, T225D, T225N, T225Q, T225R, T225S, T225H, T225A, T225V, T225L, T225I, T225F, T225M, T225Y, T225P, T225G, T225E, T225K, and T225W.

CHI regions: positions: 118, 119, 120 121, 122, 201 and 206; modifications: A118K, A118E, A118Y, S119E, T120E, K121H, G122E, N201E, and P206E Hinge regions: positions 221, 223, 224, 225, 227, 234, 235 and 236; modifications D221K, D221Y, T223E, T223K, H224E, T225E, T225K, T225W, P227K, P227G, L234D, L234E, L234Q, L234V, L234A, L234M, L234G, L235D, L235T, L235Y, G S176D, S176R, S176L, S177R, S177E, S177Y, G178D, L179K, L179Y, L179E, Y180K, Y180L, Y180E, S183T, T187I, T187K, T187E, V188I, P189D, P189G, S190I, S190K, S190E, S191D, S191R, S191Y, S192N, S192R, S192L, L193F, L193E, G194R, G194D, T195R, T195D, T195Y, Q196K, Q196D, Q196L, T197R, T197E, T197Y, Y198L, I199T, I199D, I199K, N201E, N201K, N201L, N203D, N203N, N203K, K205D, K205L, K205AP206A, P206E, S207K, S207D, N208R, N208E, N208Y, T209E, T209K, T209Y, K210L, K210E, K210Y, K210A, V211, V211E, V 211Y, D212Q, D212K, D212H, D212L, D212Y, K213N, K213E, K213H, K213L, K213Y, K213A, K214N, K214E, K214H, K214L, K214Y, K214A, E216N, E216K, E216H, E216L, E216Y, P217D, P217H, P217A, P217V, P217G, K218D, K218E, K218Q, K218T, K218H, K218L, K218Y, K218A, S219D, S219E, S219Q, S219K, S219T, S219H, S219L, S219I, S219Y, D221K, D221Y, D221E, D221N, D221Q, D221R, D221S, D221T, D221H, D221A, D221V, D221L, D221I, D221F, D221M, D221W, D221P, D221G, K222E, K222Y, K222D, K222N, K222Q, K222R, K222S, K222T, K222H, K222V, K222L, K222I, K222F, K222M, K222W, K222P, K222G, K222A, T223D, T223N, T223Q, T223R, T223S, T223H, T223A, T223V, T223L, T223I, T223F, T223M, T223Y, T223W, T223P, T223G, T223E, T223K, H224D, H224N, H224Q, H224K, H224R, H224S, H224T, H224V, H224L, H224I, H224F, H224M, H224W, H224P, H224G, H224E, H224Y, H224A, T225D, T225N, T225Q, T225R, T225S, T225H, T225A, T225V, T225L, T225I, T225F, T225M, T225Y, T225P, T225G, T225E, T225K.

The present invention also provides methods for engineering optimized antibody variants.

The present invention provides isolated nucleic acids encoding the antibody variants described herein. The present invention provides vectors comprising said nucleic acids, optionally, operably linked to control sequences. The present invention provides host cells containing the vectors, and methods for producing and optionally recovering the antibody variants.

The present invention provides novel antibodies that comprise the antibody variants disclosed herein. Said novel antibodies may find use in a therapeutic product.

The present invention provides compositions comprising antibodies that comprise the antibody variants described herein, and a physiologically or pharmaceutically acceptable carrier or diluent.

The present invention contemplates therapeutic and diagnostic uses for antibodies that comprise the antibody variants disclosed herein.

BRIEF DESCRIPTION OF THE DRAWINGS

FIGS. 3a-3f. Aligned sequences for the kappa light chain variable region Vκ (FIG. 3a), heavy chain variable region VH (FIG. 3b), light chain constant region CL (FIG. 3c), IgG CH1 (FIG. 3d), IgG hinge (FIG. 3e), and IgG CH2 and CH3 regions (FIG. 3f). For the VL and VH sequences in FIGS. 3a and 3b, the sequences of antibodies Campath-1G, Herceptin, Rituxan, and Erbitux are provided, along with the sequences of the human germline Jκ and JH segments. For these sequences, position numbering according to the Kabat and Chothi numbering schemes are provided, and CDRs as defined according to the two schemes are bolded. Bolded residues in the Campath-1G and Herceptin sequences illustrate positions and residues that are different between the two antibodies, as described in Example 2. Herceptin residue M100d and Campath-1G residue F100d were aligned sequentially with the JH region and as a result are not numbered according to Kabat. FIG. 3c shows an alignment of the Cκ and Cλ light chain constant regions, with numbering of the Cκ sequence according to the EU numbering scheme. Differences between the two aligned sequences are shown in grey. FIGS. 3d-3f show the heavy chain IgG constant regions, with numbering of the IgG1 sequence according to the EU numbering scheme. Differences between IgG1 and IgG2, IgG3, and IgG4 are shown in grey. The boundaries of the VL, VH, JL, JH, and CL regions are defined genetically, whereas the boundaries of the CH1, hinge, CH2, and CH3 regions are defined structurally, as described in Example 4. Polymorphisms have been observed at a number of immunoglobulin positions (for example see Kim et al., 2001, *J Mol Evol* 53:1-9), and thus slight differences between the presented sequence and sequences in the prior art may exist.

FIG. 5a provides AlphaScreen data showing enhanced binding of Herceptin Fc variants E272Y and K274E to human FcγRIIIa. The data were normalized, and the curves represent the fits of the data to a one site competition model. PBS was used as a negative control. FIG. 5b shows the Fc/FcγRIIIb complex structure 1IIS showing the positions of E272 and K274. Fc is shown as a gray ribbon diagram, and FcγRIIIb is shown as a black ribbon. The N297 carbohydrate is shown as black sticks, and E272 and K274 are shown as black ball and sticks.

FIG. 6a shows the entire structure, with the heavy chain shown as a gray ribbon, the light chain is shown as a black ribbon, and the carbohydrate is shown as black sticks. FIG. 6b shows a closer view of the structure, illustrating interactions at the Fab/Fc interface. The heavy chain is shown as a gray ribbon, the light chain is shown as a black ribbon. Fab residues at the interface are shown as black sticks, and Fc residues at the interface are shown as grey sticks.

FIG. 9a illustrates an inhibition, repression, or competition model, whereby Fab/Fc and/or Fab/Fab interactions may compete for Fc/FcγR interactions. FIG. 9b illustrates an activation or enhancement model, whereby Fab/FcγR and/or Fab/Fc/FcγR interactions enhance affinity of the Fc/FcγR complex. Although the models are shown with an FcγR as the effector ligand, they are meant to generally apply for any Fc or effector ligands as defined herein.

FIGS. 14a and 14b. Computational structure-based calculations on the kappa JL and CL (FIG. 14a) and JH and IgG CH1 (FIG. 14b) domains of Fab structure 1L71 (Vajdos et al., 2002, J Mol Biol 320(2):415-28) as described in Example 3. Column 1 lists the positions, and column 2 lists the wild-type amino acid identity at each position. The J regions are numbered according to the Kabat numbering scheme, and the constant domains are numbered according to EU numbering scheme. The remaining columns provide the energy for each of the natural 20 amino acids, shown in the top row. HID, HIE, and HSP represent respectively histidine with hydrogen on the delta nitrogen, histidine with hydrogen on the epsilon nitrogen, and positively charged histidine with hydrogens on both nitrogens. All substitutions were normalized with respect to the lowest energy substitution, which was set to 0 energy and is shown in dark grey. Light grey indicates substitutions within 2 kcal/mol of the lowest energy substitution, and white indicates substitutions greater than 2 kcal/mol from the lowest energy substitution. Favorable substitutions may be considered to be the lowest energy substitution for each position, and substitutions that have small energy differences from the lowest energy substitution, for example substitutions within 1-2,1-3, 1-5, or 1-10 kcal/mol. nd indicates that the substitution is not determined, typically due to extremely high energy.

FIGS. 15a and 15b. Alignments, structural analysis, and library design for the Jκ and JH segments (FIG. 15a), and Cκ and IgG CH1 chains (FIG. 15b). The sequences for the human J (heavy, kappa light and lambda light) chains, four human IgG (IgG1, IgG2, IgG3, and IgG4) CH1, and two human light (kappa and lambda) first constant regions are aligned. The J regions are numbered according to the Kabat numbering scheme, and the constant domains are numbered according to EU numbering scheme of IgG1 for the heavy chain and Cκ for the light chain. For the J region, Cam indicates the sequence of Campath. Structural analysis, by visual inspection of the 1 L71 Fab pdb structure, was used to indicate residues that reside at a critical interface (iface) (as an example, some residues in CH interact with VH and CL), in the core (core), or which potentially impact binding to antigen (antgn). This information and the calculations described in FIG. 14 were used to design the variant library, shown in the Substitutions column. Substitutions in parentheses indicate that those mutations are part of a multiple variant; these include Cκ K207A/R211A, CH1 K205A/K210A, and CH1 K213A/K214A/K218A.

FIG. 20a shows binding to human V158 FcγRIIIa by select hinge region variants. FIG. 20b shows binding to human FcγRI, FcγRIIa, FcγRIIb, FcγRIIc, FcγRIIIa, C1q, and FcRn for the D221K hinge variant. The data were normalized to the maximum and minimum luminescence signal provided by the baselines at low and high concentrations of competitor antibody respectively. The curves represent the fits of the data to a one site competition model using nonlinear regression.

DETAILED DESCRIPTION OF THE INVENTION

Figure 1:
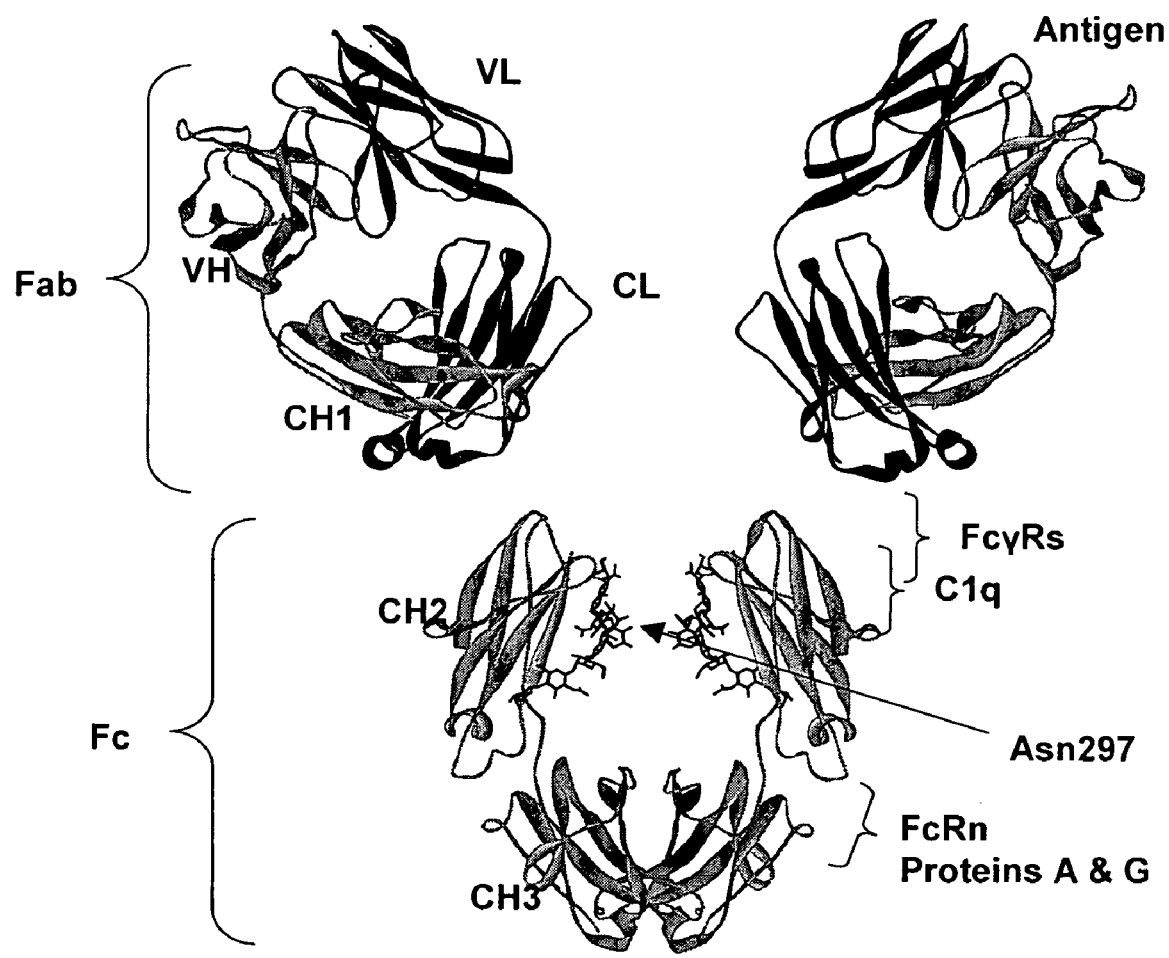
FIG. 1. Antibody structure and function. Shown is a model of a full length human IgG1 antibody, modeled using a humanized Fab structure from pdb accession code 1CE1 (James et al., 1999, *J Mol Biol* 289:293-301) and a human IgG1 Fc structure from pdb accession code 1DN2 (DeLano et al., 2000, *Science* 287:1279-1283). The flexible hinge that links the heavy chain CH1 and CH2 regions is not shown. IgG1 is a homodimer of heterodimers, made up of two light chains and two heavy chains. The 1 g domains that comprise the antibody are labeled, and include VL and CL for the light chain, and VH, CH1, CH2, and CH3 for the heavy chain. The Fab and Fc regions are labeled. Binding sites for relevant proteins are labeled, including the antigen binding site in the variable region, and the binding sites for FcγRs, FcRn, C1q, and proteins A and G in the Fc region.

In order that the invention may be more completely understood, several definitions are set forth below. Such definitions are meant to encompass grammatical equivalents.

By "amino acid" and "amino acid identity" as used herein is meant one of the 20 naturally occurring amino acids or any non-natural analogues that may be present at a specific, defined position. By "amino acid modification" herein is meant an amino acid substitution, insertion, and/or deletion in a polypeptide sequence. The preferred amino acid modification herein is a substitution. By "amino acid substitution" or "substitution" herein is meant the replacement of an amino acid at a particular position in a parent polypeptide sequence with another amino acid. For example, the substitution S119E refers to a variant polypeptide in which serine at position 119 is replaced with glutamic acid. By "amino acid insertion" or "insertion" as used herein is meant the addition of an amino acid at a particular position in a parent polypeptide sequence. For example, -52bK designates an insertion of lysine at position 52b. By "amino acid deletion" or "deletion" as used herein is meant the removal of an amino acid at a particular position in a parent polypeptide sequence. For example, A100b- designates the deletion of alanine at position 100b.

By "antibody" herein is meant a protein consisting of one or more proteins substantially encoded by all or part of the recognized immunoglobulin genes. The recognized immunoglobulin genes, for example in humans, include the kappa (κ), lambda (λ), and heavy chain genetic loci, which together comprise the myriad variable region genes, and the constant region genes mu (μ), delta (δ), gamma (γ), sigma (σ), and alpha (α) which encode the IgM, IgD, IgG, IgE, and IgA isotypes respectively. Antibody herein is meant to include full length antibodies and antibody fragments. By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains VL and CL, and each heavy chain comprising immunoglobulin domains VH, Cγ1, Cγ2, and Cγ3. In some mammals, for example in camels and llamas, IgG antibodies may consist of only two heavy chains, each heavy chain comprising a variable domain attached to the Fc region. Antibody fragments, as are known in the art, include proteins such as Fab, Fab', F(ab')$_2$, Fv, scFv, or other antigen-binding subsequences of antibodies, either produced by the modification of whole antibodies or those synthesized de novo using recombinant DNA technologies. Antibody may refer to a natural antibody from any organism, an engineered antibody, or an antibody generated recombinantly for experimental, therapeutic, or other purposes. The term antibody comprises monoclonal and polyclonal antibodies. Antibodies can be antagonists, agonists, neutralizing, inhibitory, or stimulatory.

By "antibody dependent cell-mediated cytotoxicity" or "ADCC" or as used herein is meant the cell-mediated reaction wherein nonspecific cytotoxic cells that express one or more effector ligands recognize bound antibody on a target cell and subsequently cause lysis of the target cell. By "antibody dependent cell-mediated phagocytosis" or "ADCP" or as used herein is meant the cell-mediated reaction wherein nonspecific cytotoxic cells that express one or more effector ligands recognize bound antibody on a target cell and subsequently cause phagocytosis of the target cell.

By "effector function" as used herein is meant a biochemical event that results from the interaction of an antibody with an effector ligand. Effector functions include but are not limited to antibody dependent cell-mediated cytotoxicity (ADCC), antibody dependent cell-mediated phagocytosis (ADCP), complement dependent cytotoxicity (CDC), complement dependent cellular cytotoxicity (CDCC), oxidative burst, and release of inflammatory mediators. By "effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and γδ T cells, and may be from any organism including but not limited to humans, mice, rats, rabbits, and monkeys. By "effector ligand" as used herein is meant a molecule, preferably a protein or polypeptide, from any organism that binds to an antibody to mediate one or more effector functions (Jefferis et al., 2002, *Immunol Lett* 82:57-65). Effector ligands include but are not limited to Fc receptors, FcγRs, FcαRs, FcεRs, FcRn, C1q, C3, mannan binding lectin, mannose receptor, staphylococcal protein A, streptococcal protein G, and viral FcγR. Effector ligands also include Fc receptor homologs (FcRH), which are a family of Fc receptors that are homologous to the FcγRs (Davis et al., 2002, *Immunological Reviews* 190:123-136). Effector ligands may include undiscovered effector molecules.

By "Fab" or "Fab region" as used herein is meant the polypeptides that comprises the VL, VH, CL, and CH1 immunoglobulin domains or regions. Because VL comprises the JL region and VH comprises the JH region, JL and JH also compose the Fab region. It is generally viewed in the art that the Fab region is demarcated N-terminally by the N-terminus and C-terminally by the disulfide bond that covalently links the heavy and light chains. Accordingly, for the purposes of the present invention, "Fab region" as used herein comprises from the N-terminus to residue 214 of the light chain and from the N-terminus to residue 220 of the heavy chain, wherein the numbering of the C-terminal residues is according to the EU numbering scheme. Fab may refer to this region in isolation, or this region in the context of a full length antibody or antibody fragment. Positional definitions of the regions within the Fab, including the VL, VH, JL, JH, CL, and CH1 regions, are illustrated in FIG. 3. The VL kappa and VH regions are well defined genetically and in the art, and accordingly "VL region" as used herein comprises residues 1-107, and "VH region" as used herein comprises residues 1-113, wherein numbering is according to the Kabat numbering scheme. The JL kappa region is made up of 5 germline sequences of equal length, and accordingly "JL region" as used herein comprises residues 96-107, wherein numbering is according to Kabat. There are 6 JH germline sequences of differing length, and the exact Kabat position at which this segment combines with the VH germline varies. For the purposes of the present invention, the JH region is defined to comprise the residues of these sequences that are clearly defined in a Kabat sequence alignment; based on this definition, "JH region" as used herein comprises residues 100-113, wherein numbering is according to the Kabat numbering scheme. The remaining C-terminal light and heavy chain sequences of the Fab are made up of the CL and CH1 regions respectively. Thus, "CL region" as used herein comprises residues 108-214, and "CH1 region" as used herein comprises residues 118-220, wherein numbering is according to the EU numbering scheme.

By "Fc" or "Fc region" as used herein is meant the polypeptides comprising the last two constant region immunoglobulin domains of IgA, IgD, and IgG, and the last three constant region immunoglobulin domains of IgE and IgM, and part of the flexible hinge N-terminal to these domains. For IgA and IgM Fc may include the J chain. For IgG, Fc comprises immunoglobulin domains CH2 and CH3, also referred to as Cgamma2 and Cgamma3 (Cγ2 and Cγ3). For IgA, Fc comprises immunoglobulin domains CH2 and CH3, also referred to as Calpha2 and Calpha3 (Cα2 and Cα3). Although the boundaries of the Fc region may vary, the human IgG heavy chain Fc region is usually defined to comprise residues C226 or P230 to its carboxyl-terminus, wherein the numbering is according to the EU numbering scheme. Fc may refer to this region in isolation, or this region in the context of a full length antibody or antibody fragment. Ergo, by "outside the Fc region" as used herein is meant the region of an antibody that does not comprise the Fc region of the antibody. In accordance with the aforementioned definition of Fc region, "outside the Fc region" for an IgG1 antibody is herein defined to be from the N-terminus up to and including residue T225 or C229, wherein the numbering is according to the EU numbering scheme. Thus the Fab region and part of the hinge region of an antibody are outside the Fc region.

By "Fc gamma receptor" or "FcγR" as used herein is meant any member of the family of proteins that bind the IgG antibody Fc region and are substantially encoded by the FcγR genes. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, *Immunol Lett* 82:57-65), as well as any undiscovered human FcγRs or FcγR isoforms or allotypes. An FcγR may be from any organism, including but not limited to humans, mice, rats, rabbits, and monkeys. Mouse FcγRs include but are not limited to FcγRI (CD64), FcγRII (CD32), FcγRIII (CD16), and FcγRIII-2 (CD16-2), as well as any undiscovered mouse FcγRs or FcγR isoforms or allotypes.

By "germline" as used herein is meant the set of sequences that compose the natural genetic repertoire of a protein, and its associated alleles.

By "hinge" or "hinge region" herein is meant the flexible polypeptide comprising the amino acids between the first and second constant domains of an antibody. The hinge is defined structurally for the purposes of the present invention, and "hinge region" as used herein for IgG comprises residues 221-236, wherein numbering is according to the EU numbering scheme.

By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full length antibodies, antibody fragments, and individual immunoglobulin domains. By "immunoglobulin (Ig) domain" herein is meant a region of an immunoglobulin that exists as a distinct structural entity as ascertained by one skilled in the art of protein structure. Ig domains typically have a characteristic β-sandwich folding topology. The known Ig domains in the IgG isotype of antibodies are VH, CH1, CH2, CH3, VL, and CL.

By "IgG" as used herein is meant a protein belonging to the class of antibodies that are substantially encoded by a recognized immunoglobulin gamma gene. In humans this class comprises IgG1, IgG2, IgG3, and IgG4.

By "parent" or "parent protein" as used herein is meant a protein that is subsequently modified to generate a variant. The parent protein may be a naturally occurring protein, or a variant or engineered version of a naturally occurring protein. Parent protein may refer to the protein itself, compositions that comprise the parent protein, or the amino acid sequence that encodes it. Accordingly, by "parent antibody" as used herein is meant an antibody that is subsequently modified to generate a variant antibody. Accordingly, by "parent sequence" as used herein is meant the sequence that encodes the parent protein or parent antibody.

By "Position" as used herein is meant a location in the sequence of a protein. Positions may be numbered sequentially, or according to an established format, for example the Kabat or EU numbering schemes. For example, position 297 is a position in the human antibody IgG1.

By "protein" herein is meant at least two covalently attached amino acids, which includes proteins, polypeptides, oligopeptides and peptides.

By "residue" as used herein is meant a position in a protein and its associated amino acid identity. For example, Asparagine 297 (also referred to as Asn297, also referred to as N297) is a residue in the human antibody IgG1.

By "target antigen" as used herein is meant the molecule that is bound specifically by the variable region of a given antibody. A target antigen may be a protein, carbohydrate, lipid, or other chemical compound. By "target cell" as used herein is meant a cell that expresses a target antigen.

By "variable region" as used herein is meant the region of an immunoglobulin that comprises one or more 1 g domains substantially encoded by any of the VL (including Vκ and Vλ), VH, JL (including Jκ and Jλ), and JH genes that make up the light chain (including κ and λ) and heavy chain immunoglobulin genetic loci respectively. A light or heavy chain variable region (VL and VH) consists of a "framework" or "FR" region interrupted by three hypervariable regions referred to as "complementarity determining regions" or "CDRs". The extent of the framework region and CDRs have been precisely defined, for example as in Kabat (see "Sequences of Proteins of Immunological Interest," E. Kabat et al., U.S. Department of Health and Human Services, (1983)), and as in Chothia (Chothia & Lesk, 1987, *J. Mol. Biol.* 196: 901-917; Chothia et al., 1989, *Nature* 342: 877-883; Al-Lazikani et al., 1997, *J. Mol. Biol.* 273: 927-948). The framework regions of an antibody, that is the combined framework regions of the constituent light and heavy chains, serves to position and align the CDRs, which are primarily responsible for binding to an antigen.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about ten amino acid modifications, and preferably from about one to about five amino acid modifications compared to the parent. The protein variant sequence herein will preferably possess at least about 80% homology with a parent protein sequence, and most preferably at least about 90% homology, more preferably at least about 95% homology. Accordingly, by "antibody variant" or "variant antibody" as used herein is meant an antibody that differs from a parent antibody by virtue of at least one amino acid modification.

By "wild type or WT" herein is meant an amino acid sequence or a nucleotide sequence that is found in nature, including allelic variations. A WT protein has an amino acid sequence or a nucleotide sequence that has not been intentionally modified.

Antibody variants of the present invention may be substantially encoded by genes from any organism, preferably mammals, including but not limited to humans, rodents including but not limited to mice and rats, lagomorpha including but not limited to rabbits and hares, camelidae including but not limited to camels, llamas, and dromedaries, and non-human primates, including but not limited to Prosimians, Platyrrhini (New World monkeys), Cercopithecoidea (Old World monkeys), and Hominoidea including the Gibbons and Lesser and Great Apes. In a most preferred embodiment, the antibody variants of the present invention are substantially human. The antibody variants of the present invention may be substantially encoded by immunoglobulin genes belonging to any of the antibody classes. In a most preferred embodiment, the antibody variants of the present invention comprise sequences belonging to the IgG class of antibodies, including human subclasses IgG1, IgG2, IgG3, and IgG4. In an alternate embodiment, the antibody variants of the present invention comprise sequences belonging to the IgA (including human subclasses IgA1 and IgA2), IgD, IgE, IgG, or IgM classes of antibodies. The antibody variants of the present invention may comprise more than one protein chain. That is, the present invention may find use in an antibody variant that is a monomer or an oligomer, including a homo- or hetero-oligomer.

In the most preferred embodiment, the antibody variants of the invention are based on human IgG sequences, and thus human IgG sequences are used as the "base" sequences against which other sequences are compared, including but not limited to sequences from other organisms, for example rodent and primate sequences, as well as sequences from other immunoglobulin classes such as IgA, IgE, IgGD, IgGM, and the like. It is contemplated that, although the antibody variants of the present invention are engineered in the context of one parent antibody variant, the variants may be engineered in or "transferred" to the context of another, second parent antibody variant. This is done by determining the "equivalent" or "corresponding" residues and substitutions between the first and second antibody variants, typically based on sequence or structural homology between the sequences of the two antibody variants. In order to establish homology, the amino acid sequence of a first antibody variant outlined herein is directly compared to the sequence of a second antibody variant. After aligning the sequences, using one or more of the homology alignment programs known in the art (for example using conserved residues as between species), allowing for necessary insertions and deletions in order to maintain alignment (i.e., avoiding the elimination of conserved residues through arbitrary deletion and insertion), the residues equivalent to particular amino acids in the primary sequence of the first antibody variant are defined. Alignment of conserved residues preferably should conserve 100% of such residues. However, alignment of greater than 75% or as little as 50% of conserved residues is also adequate to define equivalent residues. Equivalent residues may also be defined by determining structural homology between a first and second Antibody variant that is at the level of tertiary structure for antibody variants whose structures have been determined. In this case, equivalent residues are defined as those for which the atomic coordinates of two or more of the main chain atoms of a particular amino acid residue of the parent or precursor (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins. Regardless of how equivalent or corresponding residues are determined, and regardless of the identity of the parent antibody variant in which the antibody variants are made, what is meant to be conveyed is that the antibody variants discovered by the present invention may be engineered into any second parent Antibody variant that has significant sequence or structural homology with said antibody variant. Thus for example, if a variant antibody is generated wherein the parent antibody is human IgG1, by using the methods described above or other methods for determining equivalent residues, said variant antibody may be engineered in another IgG1 parent antibody that binds a different antigen, a human IgG2 parent antibody, a human IgA parent antibody, a mouse IgG2a or IgG2b parent antibody, and the like. Again, as described above, the context of the parent antibody variant does not affect the ability to transfer the antibody variants of the present invention to other parent antibody variants.

Virtually any binding partner or antigen may be targeted by the antibody variants of the present invention, including but are not limited to proteins, subunits, domains, motifs, and epitopes belonging to the following list of proteins: CD2; CD3, CD3E, CD4, CD11, CD11a, CD14, CD16, CD18, CD19, CD20, CD22, CD23, CD25, CD28, CD29, CD30, CD32, CD33 (p67 protein), CD38, CD40, CD40L, CD52, CD54, CD56, CD80, CD147, GD3, IL-1, IL-1R, IL-2, IL-2R, IL-4, IL-5, IL-6, IL-6R, IL-8, IL-12, IL-15, IL-18, IL-23, interferon alpha, interferon beta, interferon gamma; TNF-alpha, TNFbeta2, TNFc, TNFalphabeta, TNF-R1, TNF-RII, FasL, CD27L, CD30L, 4-1BBL, TRAIL, RANKL, TWEAK, APRIL, BAFF, LIGHT, VEG1, OX40L, TRAIL Receptor-1, A1 Adenosine Receptor, Lymphotoxin Beta Receptor, TACI, BAFF-R, EPO; LFA-3, ICAM-1, ICAM-3, EpCAM, integrin beta1, integrin beta2, integrin alpha4/beta7, integrin alpha2, integrin alpha3, integrin alpha4, integrin alpha5, integrin alpha6, integrin alphav, alphaVbeta3 integrin, FGFR-3, Keratinocyte Growth Factor, VLA-1, VLA-4, L-selectin, anti-Id, E-selectin, HLA, HLA-DR, CTLA-4, T cell receptor, B7-1, B7-2, VNRintegrin, TGFbeta1, TGFbeta2, eotaxin1, BLyS (B-lymphocyte Stimulator), complement C5, IgE, factor VII, CD64, CBL, NCA 90, EGFR (ErbB-1), Her2/neu (ErbB-2), Her3 (ErbB-3), Her4 (ErbB4), Tissue Factor, VEGF, VEGFR, endothelin receptor, VLA-4, Hapten NP-cap or NIP-cap, T cell receptor alpha/beta, E-selectin, digoxin, placental alkaline phosphatase (PLAP) and testicular PLAP-like alkaline phosphatase, transferrin receptor, Carcinoembryonic antigen (CEA), CEACAM5, HMFG PEM, mucin MUC1, MUC18, Heparanase I, human cardiac myosin, tumor-associated glycoprotein-72 (TAG-72), tumor-associated antigen CA 125, Prostate specific membrane antigen (PSMA), High molecular weight melanoma-associated antigen (HMW-MAA), carcinoma-associated antigen, Gcoprotein IIb/IIIa (GPIIb/IIIa), tumor-associated antigen expressing Lewis Y related carbohydrate, human cytomegalovirus (HCMV) gH envelope glycoprotein, HIV gp120, HCMV, respiratory syncital virus RSV F, RSVF Fgp, VNRintegrin, IL-8, cytokeratin tumor-associated antigen, Hep B gp120, CMV, gpIIbIIIa, HIV IIIB gp120 V3 loop, respiratory syncytial virus (RSV) Fgp, Herpes simplex virus (HSV) gD glycoprotein, HSV gB glycoprotein, HCMV gB envelope glycoprotein, and Clostridium perfringens toxin. A number biotherapeutic antibodies that are approved for use, in clinical trials, or in development may thus benefit from antibody variants of the present invention. Thus in a preferred embodiment, the antibody variants of the present invention may find use in a range of clinical products and candidates. Other targets and clinical products and candidates that may benefit from the antibody variants of the present invention include but are not limited to those described in U.S. Ser. No. 10/672,280 and U.S. Ser. No. 60/627,774.

The antibody variants of the present invention may comprise one or more additional modifications that provide optimized properties. Said modifications may be amino acid modifications, or may be modifications that are made enzymatically or chemically. Such modification(s) likely provide some improvement in the antibody, for example an enhancement in its stability, solubility, function, or clinical use. The present invention contemplates a variety of improvements that made be made by coupling the antibody variants of the present invention with additional modifications.

In a preferred embodiment, the antibody variants of the present invention may comprise modifications to reduce immunogenicity in humans. In a most preferred embodiment, the immunogenicity of an antibody variant of the present invention is reduced using a method described in U.S. Ser. No. 11/004,590, filed Dec. 3, 2004, entitled "Methods of Generating Variant Proteins with Increased Host String Content and Compositions Thereof". In alternate embodiments, the antibody variants of the present invention are humanized (Clark, 2000, Immunol Today 21:397-402). By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) VL and VH frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). The humanized antibody optimally also will comprise at least a portion of an immunoglobulin constant region, typically that of a human immunoglobulin, and thus will typically comprise a human Fc region. A variety of techniques and methods for humanizing and reshaping non-human antibodies are well known in the art (See Tsurushita & Vasquez, 2004, Humanization of Monoclonal Antibodies, Molecular Biology of B Cells, 533-545, Elsevier Science (USA), and references cited therein). Humanization methods include but are not limited to methods described in Jones et al., 1986, Nature 321:522-525; Riechmann et al., 1988; Nature 332:323-329; Verhoeyen et al., 1988, Science, 239:1534-1536; Queen et al., 1989, Proc Natl Acad Sci, USA 86:10029-33; He et al., 1998, J. Immunol. 160: 1029-1035; Carter et al., 1992, Proc Natl Acad Sci USA 89:4285-9, Presta et al., 1997, Cancer Res. 57(20):4593-9; Gorman et al., 1991, Proc. Natl. Acad. Sci. USA 88:4181-4185; O'Connor et al., 1998, Protein Eng 11:321-8. Humanization or other methods of reducing the immunogenicity of nonhuman antibody variable regions may include resurfacing methods, as described for example in Roguska et al., 1994, Proc. Natl. Acad. Sci. USA 91:969-973. In one embodiment, the parent antibody has been affinity matured, as is known in the art. Structure-based methods may be employed for humanization and affinity maturation, for example as described in U.S. Ser. No. 11/004,590. Selection based methods may be employed to humanize and/or affinity mature antibody variable regions, including but not limited to methods described in Wu et al., 1999, J. Mol. Biol. 294:151-162; Baca et al., 1997, J. Biol. Chem. 272(16):10678-10684; Rosok et al., 1996, J. Biol. Chem. 271(37): 22611-22618; Rader et al., 1998, Proc. Natl. Acad. Sci. USA 95: 8910-8915; Krauss et al., 2003, Protein Engineering 16(10):753-759. Other humanization methods may involve the grafting of only parts of the CDRs, including but not limited to methods described in U.S. Ser. No. 09/810,502; Tan et al., 2002, J. Immunol. 169:1119-1125; De Pascalis et al., 2002, J. Immunol. 169:3076-3084.

Modifications to reduce immunogenicity may include modifications that reduce binding of processed peptides derived from the parent sequence to MHC proteins. For example, amino acid modifications would be engineered such that there are no or a minimal number of immune epitopes that are predicted to bind, with high affinity, to any prevalent MHC alleles. Several methods of identifying MHC-binding epitopes in protein sequences are known in the art and may be used to score epitopes in an Antibody variant of the present invention. See for example WO 98/52976; WO 02/079232; WO 00/3317; U.S. Ser. No. 09/903,378; U.S. Ser. No. 10/039,170; U.S. Ser. No. 60/222, 697; U.S. Ser. No. 10/754,296; PCT WO 01/21823; and PCT WO 02/00165; Mallios, 1999, Bioinformatics 15: 432-439; Mallios, 2001, Bioinformatics 17: 942-948; Sturniolo et al., 1999, Nature Biotech. 17: 555-561; WO 98/59244; WO 02/069232; WO 02/77187; Marshall et al., 1995, J. Immunol. 154: 5927-5933; and Hammer et al., 1994, J. Exp. Med. 180: 2353-2358. Sequence-based information can be used to determine a binding score for a given peptide—MHC interaction (see for example Mallios, 1999, Bioinformatics 15: 432-439; Mallios, 2001, Bioinformatics 17: p942-948; Sturniolo et al., 1999, Nature Biotech. 17: 555-561).

The Fc region of the antibody may be modified in some way to make it more effective therapeutically. For example, the Fc region may comprise substitutions that enhance therapeutic properties. Most preferred substitutions and optimized effector function properties are described in U.S. Ser. No. 10/672,280, U.S. Ser. No. 10/822,231, entitled "Optimized Fc Variants and Methods for their Generation", U.S. Ser. No. 60/627,774, entitled "Optimized Fc Variants", and U.S. Ser. No. 60/642,477, entitled "Improved Fc Variants". Other known Fc variants that may find use in the present invention include but are not limited to those described in U.S. Pat. No. 6,737,056; PCT U.S. 2004/000643; U.S. Ser. No. 10/370,749; PCT/US2004/005112; U.S. 2004/0132101; U.S. Ser. No. 10/672,280; PCT/US03/30249; U.S. Pat. No. 6,737,056, U.S. 2004/0002587; WO 2004/063351; Idusogie et al., 2001, *J. Immunology* 166:2571-2572; Hinton et al., 2004, *J. Biol. Chem.* 279(8): 6213-6216. In alternate embodiments, the constant region may comprise one or more engineered glycoforms, as is known in the art (Umana et al., 1999, *Nat Biotechnol* 17:176-180; Davies et al., 2001, *Biotechnol Bioeng* 74:288-294; Shields et al., 2002, *J Biol Chem* 277:26733-26740; Shinkawa et al., 2003, *J Biol Chem*278:3466-3473); (U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1; Potelligent™ technology [Biowa, Inc., Princeton, N.J.]; GlycoMAb™ glycosylation engineering technology [GLYCART biotechnology AG, Zurich, Switzerland]).

In an alternate embodiment, the antibody variant of the present invention is conjugated or operably linked to another therapeutic compound. The therapeutic compound may be a cytotoxic agent, a chemotherapeutic agent, a toxin, a radioisotope, a cytokine, or other therapeutically active agent. The antibody may be linked to one of a variety of nonproteinaceous polymers, e.g., polyethylene glycol, polypropylene glycol, polyoxyalkylenes, or copolymers of polyethylene glycol and polypropylene glycol.

The present invention provides methods for engineering, producing, and screening antibody variants. The described methods are not meant to constrain the present invention to any particular application or theory of operation. Rather, the provided methods are meant to illustrate generally that one or more antibody variants may be engineered, produced, and screened experimentally to obtain antibodies with optimized effector function. A variety of methods are described for designing, producing, and testing antibody and protein variants in U.S. Ser. No. 10/754,296, and U.S. Ser. No. 10/672,280, which are herein expressly incorporated by reference.

A variety of protein engineering methods may be used to design Fab and/or hinge variants with altered effector function. In one embodiment, a structure-based engineering method may be used, wherein available structural information is used to guide substitutions. In a preferred embodiment, a computational screening method may be used, wherein substitutions are designed based on their energetic fitness in computational calculations. See for example U.S. Ser. No. 10/754,296 and U.S. Ser. No. 10/672,280, and references cited therein.

An alignment of sequences may be used to guide substitutions at the identified positions. One skilled in the art will appreciate that the use of sequence information may curb the introduction of substitutions that are potentially deleterious to antibody structure. The source of the sequences may vary widely, and include one or more of the known databases, including but not limited to the Kabat database (.immuno.b-me.nwu.edu; Johnson & Wu, 2001, *Nucleic Acids Res.* 29:205-206; Johnson & Wu, 2000, *Nucleic Acids Res.* 28:214-218), the IMGT database (IMGT, the international ImMunoGeneTics information system®; imgt.cines.fr; Lefranc et al., 1999, *Nucleic Acids Res.* 27:209-212; Ruiz et al., 2000 *Nucleic Acids Res.* 28:219-221; Lefranc et al., 2001, *Nucleic Acids Res.* 29:207-209; Lefranc et al., 2003, *Nucleic Acids Res.* 31:307-310), and VBASE (.mrc-cpe.cam.ac.uk/vbase-ok.php?menu=901). Antibody sequence information can be obtained, compiled, and/or generated from sequence alignments of germline sequences or sequences of naturally occurring antibodies from any organism, including but not limited to mammals. One skilled in the art will appreciate that the use of sequences that are human or substantially human may further have the advantage of being less immunogenic when administered to a human. Other databases which are more general nucleic acid or protein databases, i.e. not particular to antibodies, include but are not limited to SwissProt (expasy.ch/sprot/), GenBank (ncbi.nlm.nih.gov/Genbank) and Entrez (ncbi.nlm.nih.gov/Entrez/), and EMBL Nucleotide Sequence Database (ebi.ac.uk/embl/). Aligned sequences may comprise VH, VL, CH1, and/or CL sequences. There are numerous sequence-based alignment programs and methods known in the art, and all of these find use in the present invention for generation of sequence alignments.

Alternatively, random or semi-random mutagenesis methods may be used to make amino acid modifications at the desired positions. In these cases positions are chosen randomly, or amino acid changes are made using simplistic rules. For example all residues may be mutated to alanine, referred to as alanine scanning. Such methods may be coupled with more sophisticated engineering approaches that employ selection methods to screen higher levels of sequence diversity. As is well known in the art, there are a variety of selection technologies that may be used for such approaches, including, for example, display technologies such as phage display, ribosome display, cell surface display, and the like, as described below.

Methods for production and screening of antibody variants are well known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, *Curr Opin Chem Biol* 5:683-689; Maynard & Georgiou, 2000, *Annu Rev Biomed Eng* 2:339-76. Also see the methods described in U.S. Ser. No. 10/754, 296, filed on Mar. 3, 2003, U.S. Ser. No. 10/672,280, filed Sep. 29, 2003, and U.S. Ser. No. 10/822,231, filed Mar. 26, 2004.

In one embodiment of the present invention, the antibody variant sequences are used to create nucleic acids that encode the member sequences, and that may then be cloned into host cells, expressed and assayed, if desired. These practices are carried out using well-known procedures, and a variety of methods that may find use in the present invention are described in Molecular Cloning—A Laboratory Manual, $3^{rd}$ Ed. (Maniatis, Cold Spring Harbor Laboratory Press, New York, 2001), and Current Protocols in Molecular Biology (John Wiley & Sons). The nucleic acids that encode the antibody variants of the present invention may be incorporated into an expression vector in order to express the antibody. Expression vectors typically comprise a antibody operably linked, that is placed in a functional relationship, with control or regulatory sequences, selectable markers, any fusion partners, and/or additional elements. The antibody variants of the present invention may be produced by culturing a host cell transformed with nucleic acid, preferably an expression vector, containing nucleic acid encoding the antibody variants, under the appropriate conditions to induce or cause expression of the antibody. A wide variety of appropriate host cells may be used, including but not limited to mammalian cells, bacteria, insect cells, and yeast. For example, a variety of cell lines that may find use in the present invention are described in the ATCC cell line catalog, available from the American Type Culture Collection. The methods of introducing exogenous nucleic acid into host cells are well known in the art, and will vary with the host cell used.

In a preferred embodiment, antibody variants are purified or isolated after expression. Antibodies may be isolated or purified in a variety of ways known to those skilled in the art. Standard purification methods include chromatographic techniques, electrophoretic, immunological, precipitation, dialysis, filtration, concentration, and chromatofocusing techniques. As is well known in the art, a variety of natural antibodys bind antibodies, for example bacterial antibodys A, G, and L, and these antibodys may find use in the present invention for purification. Purification can often be enabled by a particular fusion partner. For example, antibodys may be purified using glutathione resin if a GST fusion is employed, $Ni^{+2}$ affinity chromatography if a His-tag is employed, or immobilized anti-flag antibody if a flag-tag is used. For general guidance in suitable purification techniques, see Antibody Purification: Principles and Practice, $3^{rd}$ Ed., Scopes, Springer-Verlag, NY, 1994.

Antibody variants may be screened using a variety of methods, including but not limited to those that use in vitro assays, in vivo and cell-based assays, and selection technologies. Automation and high-throughput screening technologies may be utilized in the screening procedures. Screening may employ the use of a fusion partner or label, for example an immune label, isotopic label, or small molecule label such as a fluorescent or colorimetric dye.

In a preferred embodiment, the functional and/or biophysical properties of antibody variants are screened in an in vitro assay. In a preferred embodiment, the antibody is screened for functionality, for example its ability to catalyze a reaction or its binding affinity to its target. Binding assays can be carried out using a variety of methods known in the art, including but not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label. Assays may employ a variety of detection methods including but not limited to chromogenic, fluorescent, luminescent, or isotopic labels. The biophysical properties of antibodys, for example stability and solubility, may be screened using a variety of methods known in the art. Antibody stability may be determined by measuring the thermodynamic equilibrium between folded and unfolded states. For example, antibody variants of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of a antibody variant may be quantitatively or qualitatively determined using a wide range of methods that are known in the art. Methods which may find use in the present invention for characterizing the biophysical properties of antibody variants include gel electrophoresis, chromatography such as size exclusion chromatography and reversed-phase high performance liquid chromatography, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, antibody-staining assays, microscopy, and detection of aggregates via ELISA or other binding assay. Structural analysis employing X-ray crystallographic techniques and NMR spectroscopy may also find use.

As is known in the art, a subset of screening methods are those that select for favorable members of a library. The methods are herein referred to as "selection methods", and these methods find use in the present invention for screening antibody variants. When antibody libraries are screened using a selection method, only those members of a library that are favorable, that is which meet some selection criteria, are propagated, isolated, and/or observed. As will be appreciated, because only the most fit variants are observed, such methods enable the screening of libraries that are larger than those screenable by methods that assay the fitness of library members individually. Selection is enabled by any method, technique, or fusion partner that links, covalently or noncovalently, the phenotype of a antibody with its genotype, that is the function of a antibody with the nucleic acid that encodes it. For example the use of phage display as a selection method is enabled by the fusion of library members to the gene III antibody. In this way, selection or isolation of antibody variants that meet some criteria, for example binding affinity to the antibody's target, also selects for or isolates the nucleic acid that encodes it. Once isolated, the gene or genes encoding Fc variants may then be amplified. This process of isolation and amplification, referred to as panning, may be repeated, allowing favorable antibody variants in the library to be enriched. Nucleic acid sequencing of the attached nucleic acid ultimately allows for gene identification.

A variety of selection methods are known in the art that may find use in the present invention for screening antibody libraries. These include but are not limited to phage display (Phage display of peptides and antibodys: a laboratory manual, Kay et al., 1996, Academic Press, San Diego, Calif., 1996; Lowman et al., 1991, *Biochemistry* 30:10832-10838; Smith, 1985, *Science* 228:1315-1317) and its derivatives such as selective phage infection (Malmborg et al., 1997, *J Mol Biol* 273:544-551), selectively infective phage (Krebber et al., 1997, *J Mol Biol* 268:619-630), and delayed infectivity panning (Benhar et al., 2000, *J Mol Biol* 301:893-904), cell surface display (Witrrup, 2001, *Curr Opin Biotechnol*, 12:395-399) such as display on bacteria (Georgiou et al., 1997, *Nat Biotechnol* 15:29-34; Georgiou et al., 1993, *Trends Biotechnol* 11:6-10; Lee et al., 2000, *Nat Biotechnol* 18:645-648; Jun et al., 1998, *Nat Biotechnol* 16:576-80), yeast (Boder & Wittrup, 2000, *Methods Enzymol* 328:430-44; Boder & Wittrup, 1997, *Nat Biotechnol* 15:553-557), and mammalian cells (Whitehorn et al., 1995, *Bio/technology* 13:1215-1219), as well as in vitro display technologies (Amstutz et al., 2001, *Curr Opin Biotechnol* 12:400-405) such as polysome display (Mattheakis et al., 1994, *Proc Natl Acad Sci USA* 91:9022-9026), ribosome display (Hanes et al., 1997, *Proc Natl Acad Sci USA* 94:4937-4942), mRNA display (Roberts & Szostak, 1997, *Proc Natl Acad Sci USA* 94:12297-12302; Nemoto et al., 1997, *FEBS Lett* 414:405-408), and ribosome-inactivation display system (Zhou et al., 2002, *J Am Chem Soc* 124, 538-543).

Other selection methods that may find use in the present invention include methods that do not rely on display, such as in vivo methods including but not limited to periplasmic expression and cytometric screening (Chen et al., 2001, *Nat Biotechnol* 19:537-542), the antibody fragment complementation assay (Johnsson & Varshavsky, 1994, *Proc Natl Acad Sci USA* 91:10340-10344; Pelletier et al., 1998, *Proc Natl Acad Sci USA* 95:12141-12146), and the yeast two hybrid screen (Fields & Song, 1989, *Nature* 340:245-246) used in selection mode (Visintin et al., 1999, *Proc Natl Acad Sci USA* 96:11723-11728). In an alternate embodiment, selection is enabled by a fusion partner that binds to a specific sequence on the expression vector, thus linking covalently or noncovalently the fusion partner and associated Fc variant library member with the nucleic acid that encodes them. For example, U.S. Ser. No. 09/642,574; U.S. Ser. No. 10/080,376; U.S. Ser. No. 09/792,630; U.S. Ser. No. 10/023,208; U.S. Ser. No. 09/792,626; U.S. Ser. No. 10/082,671; U.S. Ser. No. 09/953,351; U.S. Ser. No. 10/097,100; U.S. Ser. No. 60/366,658; PCT WO 00/22906; PCT WO 01/49058; PCT WO 02/04852; PCT WO 02/04853; PCT WO 02/08023; PCT WO 01/28702; and PCT WO 02/07466 describe such a fusion partner and technique that may find use in the present invention. In an alternative embodiment, in vivo selection can occur if expression of the antibody imparts some growth, reproduction, or survival advantage to the cell.

A subset of selection methods referred to as "directed evolution" methods are those that include the mating or breading of favorable sequences during selection, sometimes with the incorporation of new mutations. As will be appreciated by those skilled in the art, directed evolution methods can facilitate identification of the most favorable sequences in a library, and can increase the diversity of sequences that are screened. A variety of directed evolution methods are known in the art that may find use in the present invention for screening antibody variants, including but not limited to DNA shuffling (PCT WO 00/42561 A3; PCT WO 01/70947 A3), exon shuffling (U.S. Pat. No. 6,365,377; Kolkman & Stemmer, 2001, *Nat Biotechnol* 19:423-428), family shuffling (Crameri et al., 1998, *Nature* 391:288-291; U.S. Pat. No. 6,376,246), RACHITT™ (Coco et al., 2001, *Nat Biotechnol* 19:354-359; PCT WO 02/06469), STEP and random priming of in vitro recombination (Zhao et al., 1998, *Nat Biotechnol* 16:258-261; Shao et al., 1998, *Nucleic Acids Res* 26:681-683), exonuclease mediated gene assembly (U.S. Pat. No. 6,352,842; U.S. Pat. No. 6,361,974), Gene Site Saturation Mutagenesis™ (U.S. Pat. No. 6,358,709), Gene Reassembly™ (U.S. Pat. No. 6,358,709), SCRATCHY (Lutz et al., 2001, *Proc Natl Acad Sci USA* 98:11248-11253), DNA fragmentation methods (Kikuchi et al., *Gene* 236:159-167), single-stranded DNA shuffling (Kikuchi et al., 2000, *Gene* 243:133-137), and AMEsystem™ directed evolution antibody engineering technology (Applied Molecular Evolution) (U.S. Pat. No. 5,824,514; U.S. Pat. No. 5,817,483; U.S. Pat. No. 5,814,476; U.S. Pat. No. 5,763,192; U.S. Pat. No. 5,723,323).

In a preferred embodiment, antibody variants are screened using one or more cell-based or in vivo assays. For such assays, purified or unpurified antibodys are typically added exogenously such that cells are exposed to individual variants or pools of variants belonging to a library. These assays are typically, but not always, based on the function of the antibody; that is, the ability of the antibody to bind to its target and mediate some biochemical event, for example effector function, ligand/receptor binding inhibition, apoptosis, and the like. Such assays often involve monitoring the response of cells to the antibody, for example cell survival, cell death, change in cellular morphology, or transcriptional activation such as cellular expression of a natural gene or reporter gene. For example, such assays may measure the ability of antibody variants to elicit ADCC, ADCP, or CDC. For some assays additional cells or components, that is in addition to the target cells, may need to be added, for example example serum complement, or effector cells such as peripheral blood monocytes (PBMCs), NK cells, macrophages, and the like. Such additional cells may be from any organism, preferably humans, mice, rat, rabbit, and monkey. Antibodys may cause apoptosis of certain cell lines expressing the target, or they may mediate attack on target cells by immune cells which have been added to the assay. Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored. In a preferred embodiment, the DELFIA® EuTDA-based cytotoxicity assay (Perkin Elmer, MA) is used. Alternatively, dead or damaged target cells may be monitoried by measuring the release of one or more natural intracellular antibodys, for example lactate dehydrogenase. Transcriptional activation may also serve as a method for assaying function in cell-based assays. In this case, response may be monitored by assaying for natural genes or antibodys which may be upregulated, for example the release of certain interleukins may be measured, or alternatively readout may be via a reporter construct. Cell-based assays may also involve the measure of morphological changes of cells as a response to the presence of a antibody. Cell types for such assays may be prokaryotic or eukaryotic, and a variety of cell lines that are known in the art may be employed. Alternatively, cell-based screens are performed using cells that have been transformed or transfected with nucleic acids encoding the variants. That is, antibody variants are not added exogenously to the cells. For example, in one embodiment, the cell-based screen utilizes cell surface display. A fusion partner can be employed that enables display of antibody variants on the surface of cells (Witrrup, 2001, *Curr Opin Biotechnol,* 12:395-399).

In a preferred embodiment, the immunogenicity of the antibody variants is determined experimentally using one or more cell-based assays. Several methods can be used for experimental confirmation of epitopes. In a preferred embodiment, ex vivo T-cell activation assays are used to experimentally quantitate immunogenicity. In this method, antigen presenting cells and naïve T cells from matched donors are challenged with a peptide or whole antibody of interest one or more times. Then, T cell activation can be detected using a number of methods, for example by monitoring production of cytokines or measuring uptake of tritiated thymidine. In the most preferred embodiment, interferon gamma production is monitored using Elispot assays (Schmittel et. al., 2000, *J. Immunol. Meth.,* 24: 17-24).

The biological properties of the antibody variants of the present invention may be characterized in cell, tissue, and whole organism experiments. As is known in the art, drugs are often tested in animals, including but not limited to mice, rats, rabbits, dogs, cats, pigs, and monkeys, in order to measure a drug's efficacy for treatment against a disease or disease model, or to measure a drug's pharmacokinetics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic. Any organism, preferably mammals, may be used for testing. For example because of their genetic similarity to humans, monkeys can be suitable therapeutic models, and thus may be used to test the efficacy, toxicity, pharmacokinetics, or other property of the antibodys of the present invention. Tests of the in humans are ultimately required for approval as drugs, and thus of course these experiments are contemplated. Thus the antibodys of the present invention may be tested in humans to determine their therapeutic efficacy, toxicity, immunogenicity, pharmacokinetics, and/or other clinical properties.

The antibody variants of the present invention may find use in a wide range of antibody products. In one embodiment the antibody variant of the present invention is a therapeutic, a diagnostic, or a research reagent, preferably a therapeutic. The antibody variant may find use in an antibody composition that is monoclonal or polyclonal. In a preferred embodiment, the antibody variants of the present invention are used to kill target cells that bear the target antigen, for example cancer cells. In an alternate embodiment, the antibody variants of the present invention are used to block, antagonize, or agonize the target antigen, for example for antagonizing a cytokine or cytokine receptor. In an alternately preferred embodiment, the antibody variants of the present invention are used to block, antagonize, or agonize the target antigen and kill the target cells that bear the target antigen.

The antibody variants of the present invention may be used for various therapeutic purposes. In a preferred embodiment, an antibody comprising the antibody variant is administered to a patient to treat an antibody-related disorder. A "patient" for the purposes of the present invention includes both humans and other animals, preferably mammals and most preferably humans. By "antibody related disorder" or "antibody responsive disorder" or "condition" or "disease" herein are meant a disorder that may be ameliorated by the administration of a pharmaceutical composition comprising an antibody variant of the present invention. Antibody related disorders include but are not limited to autoimmune diseases, immunological diseases, infectious diseases, inflammatory diseases, neurological diseases, and oncological and neoplastic diseases including cancer. By "cancer" and "cancerous" herein refer to or describe the physiological condition in mammals that is typically characterized by unregulated cell growth. Examples of cancer include but are not limited to carcinoma, lymphoma, blastoma, sarcoma (including liposarcoma), neuroendocrine tumors, mesothelioma, schwanoma, meningioma, adenocarcinoma, melanoma, and leukemia and lymphoid malignancies.

In one embodiment, an antibody variant of the present invention is the only therapeutically active agent administered to a patient. Alternatively, the antibody variant of the present invention is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The antibody vararaints may be administered concomitantly with one or more other therapeutic regimens. For example, an antibody variant of the present invention may be administered to the patient along with chemotherapy, radiation therapy, or both chemotherapy and radiation therapy. In one embodiment, the antibody variant of the present invention may be administered in conjunction with one or more antibodies, which may or may not comprise a antibody variant of the present invention. In accordance with another embodiment of the invention, the antibody variant of the present invention and one or more other anti-cancer therapies are employed to treat cancer cells ex vivo. It is contemplated that such ex vivo treatment may be useful in bone marrow transplantation and particularly, autologous bone marrow transplantation. It is of course contemplated that the antibodies of the invention can be employed in combination with still other therapeutic techniques such as surgery.

A variety of other therapeutic agents may find use for administration with the antibody variants of the present invention. In one embodiment, the antibody is administered with an anti-angiogenic agent. By "anti-angiogenic agent" as used herein is meant a compound that blocks, or interferes to some degree, the development of blood vessels. The anti-angiogenic factor may, for instance, be a small molecule or a protein, for example an antibody, Fc fusion, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the antibody is administered with a therapeutic agent that induces or enhances adaptive immune response, for example an antibody that targets CTLA-4. In an alternate embodiment, the antibody is administered with a tyrosine kinase inhibitor. By "tyrosine kinase inhibitor" as used herein is meant a molecule that inhibits to some extent tyrosine kinase activity of a tyrosine kinase. In an alternate embodiment, the antibody variants of the present invention are administered with a cytokine. By "cytokine" as used herein is meant a generic term for proteins released by one cell population that act on another cell as intercellular mediators.

Pharmaceutical compositions are contemplated wherein an antibody variant of the present invention and one or more therapeutically active agents are formulated. Formulations of the antibody variants of the present invention are prepared for storage by mixing said antibody having the desired degree of purity with optional pharmaceutically acceptable carriers, excipients or stabilizers (Remington's Pharmaceutical Sciences 16th edition, Osol, A. Ed.,1980), in the form of lyophilized formulations or aqueous solutions. The formulations to be used for in vivo administration are preferrably sterile. This is readily accomplished by filtration through sterile filtration membranes or other methods. The antibodies and other therapeutically active agents disclosed herein may also be formulated as immunoliposomes, and/or entrapped in microcapsules The concentration of the therapeutically active antibody variant in the formulation may vary from about 0.1 to 100 weight %. In a preferred embodiment, the concentration of the antibody is in the range of 0.003 to 1.0 molar. In order to treat a patient, a therapeutically effective dose of the antibody variant of the present invention may be administered. By "therapeutically effective dose" herein is meant a dose that produces the effects for which it is administered. The exact dose will depend on the purpose of the treatment, and will be ascertainable by one skilled in the art using known techniques. Dosages may range from 0.01 to 100 mg/kg of body weight or greater, for example 0.1, 1, 10, or 50 mg/kg of body weight, with 1 to 10 mg/kg being preferred. As is known in the art, adjustments for antibody degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

Administration of the pharmaceutical composition comprising an antibody variant of the present invention, preferably in the form of a sterile aqueous solution, may be done in a variety of ways, including, but not limited to, orally, subcutaneously, intravenously, intranasally, intraotically, transdermally, topically (e.g., gels, salves, lotions, creams, etc.), intraperitoneally, intramuscularly, intrapulmonary (e.g., AERx® inhalable technology commercially available from Aradigm, or Inhance™ pulmonary delivery system commercially available from Inhale Therapeutics), vaginally, parenterally, rectally, or intraocularly.

EXAMPLES

Examples are provided below to illustrate the present invention. These examples are not meant to constrain the present invention to any particular application or theory of operation.

For all constant region (CL, CH1, hinge, CH2, and CH3) positions discussed in the present invention, numbering is according to the EU numbering scheme (Kabat et al., 1991, *Sequences of Proteins of Immunological Interest*, 5th Ed., United States Public Health Service, National Institutes of Health, Bethesda), which refers to the numbering of the EU antibody (Edelman et al., 1969, Proc Natl Acad Sci USA 63:78-85). For all variable region (VL and VH) and J segment (JH and JL) positions discussed in the present invention, numbering is according to the Kabat numbering scheme (Kabat et al., 1991, *Sequences of Proteins of Immunological Interest*, 5th Ed., United States Public Health Service, National Institutes of Health, Bethesda). Exceptions to these numbering schemes are noted where they occur. Those skilled in the art of antibodies will appreciate that these conventions consist of nonsequential numbering in specific regions of an immunoglobulin sequence, enabling a normalized reference to conserved positions in immunoglobulin families. Accordingly, the positions of any given immunoglobulin as defined by EU numbering or Kabat numbering will not necessarily correspond to its sequential sequence.

FIGS. 3a and 3b provide the VL (κ) and VH sequences for four commercial antibodies, along with the sequences of human germine Jκ and JH segments, with positions numbered according to the Kabat numbering scheme. Position numbering according to another common numbering scheme, that of Chothia, is also provided. FIGS. 3c-3f provide the CL (κ and λ) and IgG constant region sequences, with numbering according to the EU numbering scheme. The boundaries of the regions in FIG. 3 are designated based on both genetic (variable, J segment, and constant region boundaries) and structural (CH1, hinge, CH2, and CH3 boundaries). It should be noted that polymorphisms have been observed at a number of immunoglobulin positions (for example see Kim et al., 2001, J Mol Evol 53:1-9), and thus slight differences between the presented sequence and sequences in the scientific literature may exist.

Example 1

Regions Outside Fc Can Impact Interaction of an Antibody with Effector Ligands

Essentially all research aimed at modifying antibody effector function has focused on the Fc region, intuitively because it comprises the binding sites for the FcγRs and C1q. The present invention provides support for a role of antibody regions outside of the Fc region that affect Fc/effector ligand interaction. An initial basis of support for a role of the variable region in antibody effector function is the observation that antibodies that differ solely in their variable region sequences mediate differing levels of effector function. There are a number of potential explanations for this result, the most reasonable of which have concerned the properties of the target antigen, including expression level, structural accessibility, and so forth. Data set forth in the present invention suggest, however, that the variable region can affect antibody/effector ligand affinity.

Binding affinity to human FcγRIIIa was measured for two antibodies with identical Fc regions yet different variable regions—Campath® and Herceptin®. Campath (alemtuzumab, Campath-1H, a registered trademark of Ilex Pharmaceuticals LP) is a humanized anti-CD52 antibody currently approved for treatment of B-cell chronic lymphocytic leukemia. Herceptin (trastuzumab, a registered trademark of Genentech) is a humanized anti-Her2/neu antibody currently approved for treatment of breast cancer. The genes for the variable regions of Campath and Herceptin were constructed using recursive PCR, and subcloned into the mammalian expression vector pcDNA3.1Zeo (Invitrogen) comprising the full length light kappa (Cκ) and heavy chain IgG1 constant regions. DNA was sequenced to confirm the fidelity of the sequences. Plasmids containing heavy chain gene (VH-CH1-CH2-CH3) (wild-type or variants) were co-transfected with plasmid containing light chain gene (VL-Cκ) into 293T cells. Media were harvested 5 days after transfection, and antibodies were purified from the supernatant using protein A affinity chromatography (Pierce).

Figure 4:
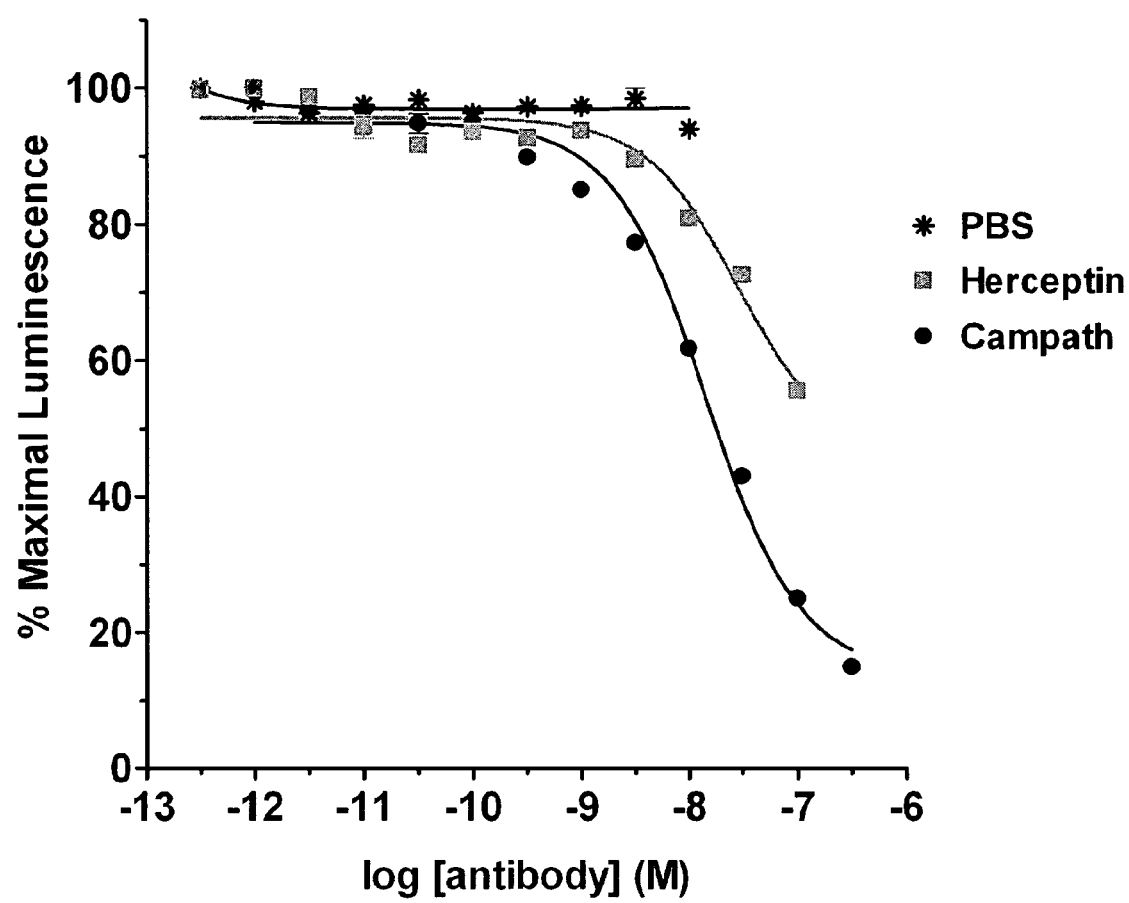
FIG. 4. Binding to human V158 FcγRIIIa by Campath and Herceptin as determined by the AlphaScreen™ assay. In the presence of competitor Campath or Herceptin antibody, a characteristic inhibition curve is observed as a decrease in luminescence signal. Phosphate buffer saline (PBS) alone was used as the negative control. These data were normalized to the maximum and minimum luminescence signal provided by the baselines at low and high concentrations of competitor antibody respectively. The curves represent the fits of the data to a one site competition model using nonlinear regression.

In order to screen for FcγR binding, the extracellular region of human V158 FcγRIIIa was expressed and purified. The extracellular region of this receptor was obtained by PCR from a clone obtained from the Mammalian Gene Collection (MGC:22630). The receptor was fused with glutathione S-Transferase (GST) to enable screening. Tagged FcγRIIIa was transfected in 293T cells, and media containing secreted FcγRIIIa were harvested 3 days later and purified. Binding affinity to human FcγRIIIa by the antibodies was measured using a quantitative and extremely sensitive method, AlphaScreen™ assay. The AlphaScreen is a bead-based luminescent proximity assay. Laser excitation of a donor bead excites oxygen, which if sufficiently close to the acceptor bead will generate a cascade of chemiluminescent events, ultimately leading to fluorescence emission at 520-620 nm. The AlphaScreen was applied as a competition assay for screening the antibodies. Wild-type Campath and Herceptin antibodies were biotinylated by standard methods for attachment to streptavidin donor beads, and tagged human FcγRIIIa (Val158 isoform) was bound to glutathione chelate acceptor beads. In the absence of competing antibody, antibody and FcγR interact and produce a signal at 520-620 nm. Addition of untagged antibody competes with the Fc/FcγR interaction, reducing fluorescence quantitatively to enable determination of relative binding affinities. FIG. 4 presents the AlphaScreen binding data for the binding of Campath and Herceptin to FcγRIIIa. The binding data were normalized to the maximum and minimum luminescence signal provided by the baselines at low and high concentrations of competitor antibody respectively. The data were fit to a one site competition model using nonlinear regression, and these fits are represented by the curves in the figure. These fits provide the inhibitory concentration 50% (IC50) (i.e. the concentration required for 50% inhibition) for each antibody, thus enabling the relative binding affinities of Fc variants to be quantitatively determined. The results show that Campath has significantly greater affinity for the receptor than Herceptin.

The difference in FcγR binding affinities between Campath and Herceptin was further corroborated using Surface Plasmon Resonance (SPR) (Biacore, Uppsala, Sweden). SPR is a sensitive and quantitative method that allows for the measurement of binding affinities of protein-protein interactions, and has been used effectively to measure Fc/FcγR binding (Radaev et al., 2001, *J Biol Chem* 276: 16478-16483). GST-tagged V158 or F158 FcγRIIIa was immobilized to an SPR chip, and Campath and Herceptin antibodies were flowed over the chip at a range of concentrations. Binding constants were obtained from fitting the data using standard curve-fitting methods. Table 1 presents dissociation constants (Kd) for binding of Campath and Herceptin to V158 FcγRIIIa and F158 FcγRIIIa obtained using SPR.

TABLE 1

|  | V158 FcγRIIIa Kd (nM) | F158 FcγRIIIa Kd (nM) |
| --- | --- | --- |
| Campath | 68 | 730 |
| Herceptin | 364 | 503 |

The SPR results confirm the AlphaScreen data, further indicating that there is a difference in the binding affinities of the two antibodies for FcγRIIIa. Furthermore, there is a substantial difference in binding specificity for the different FcγRIIIa isoforms. Because the constant region sequences of the Campath and Herceptin antibodies used in these experiments, including CL, CH1, CH2, and CH3, are identical, there exists some difference or differences between these antibodies in their variable regions that impacts the Fc/FcγR interaction.

Figure 2:
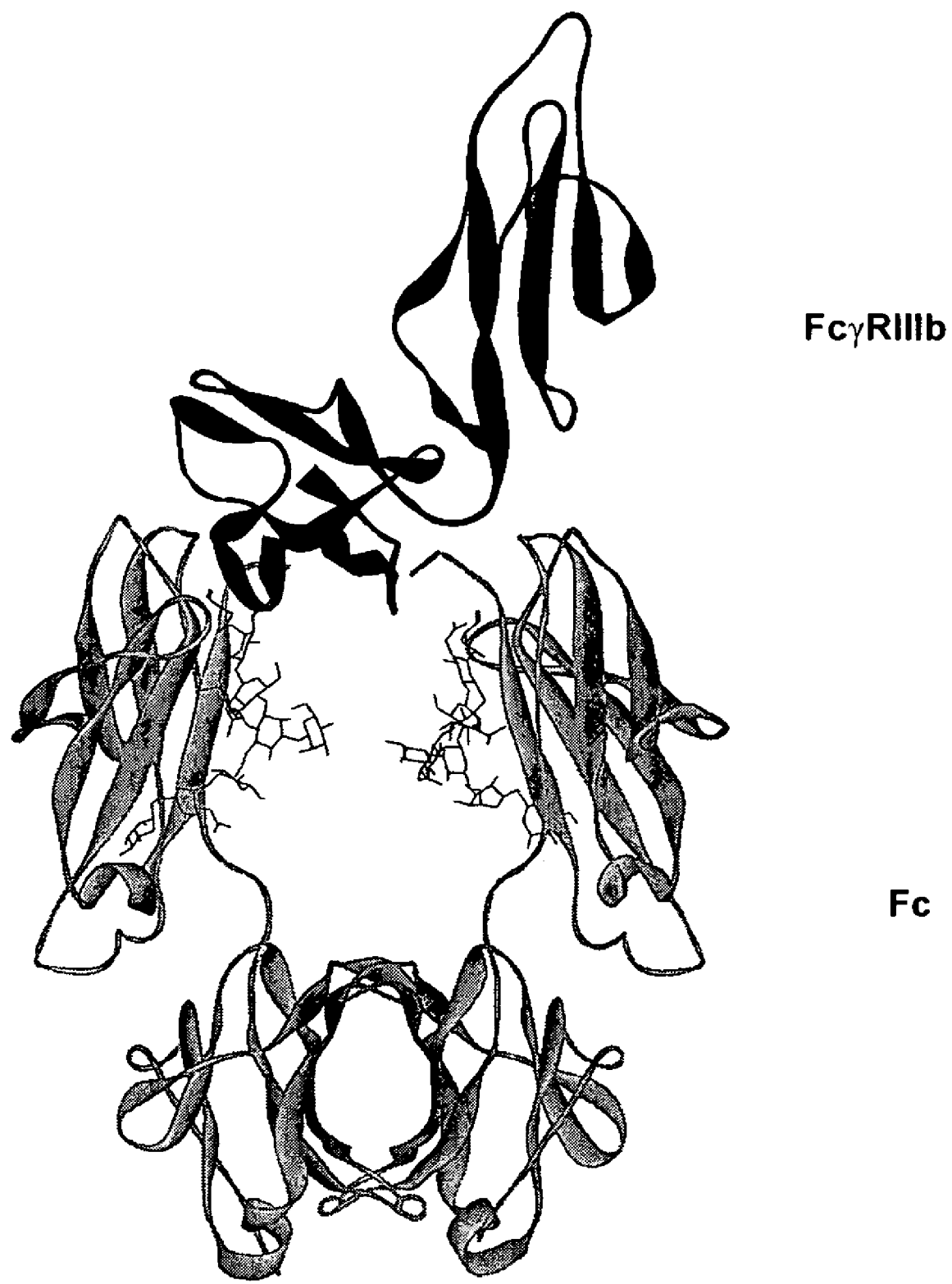
FIG. 2. The Fc/FcγRIIIb complex structure 1IIS (Radaev et al., 2001, *J Biol Chem* 276:16469-16477). Fc is shown as a gray ribbon diagram, and FcγRIIIb is shown as a black ribbon. The N297 carbohydrate is shown as black sticks.
Figure 5A:
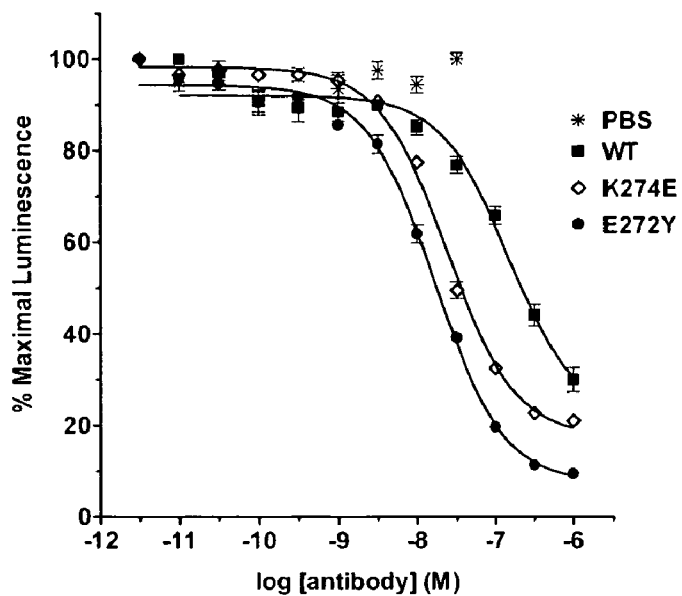
FIGS. 5a-5b. Impact of Fc mutations distal to the Fc/FcγR binding site on Fc/FcγR affinity.
Figure 5B:
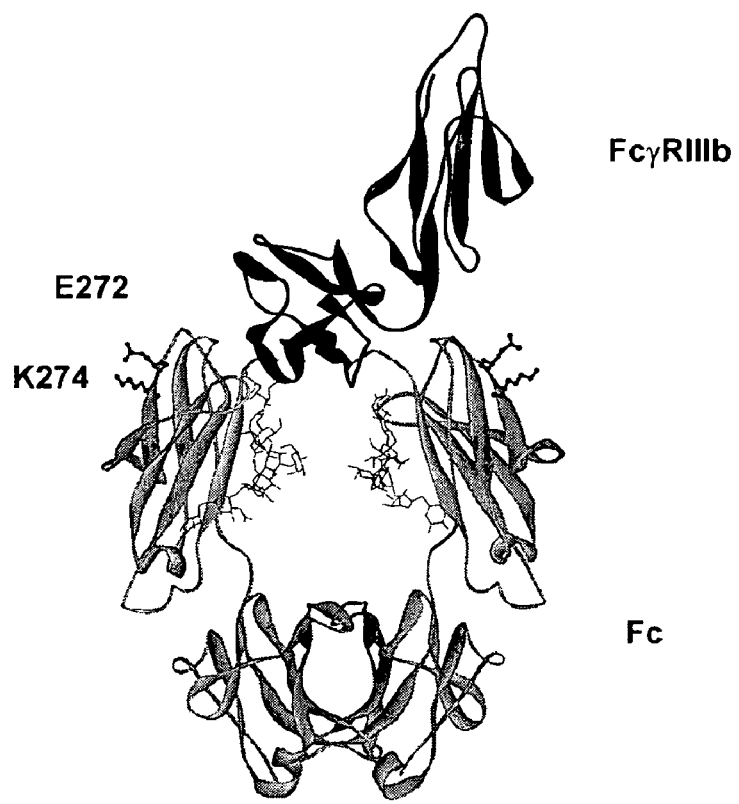
Figure 6A:
FIG. 6a-6b. Structure of a full length human antibody IgG1 b12 (pdb accession code 1HZH, Saphire et al., 2002, *J Mol Biol* 319:9-18).
Figure 6B:
Figure 7:
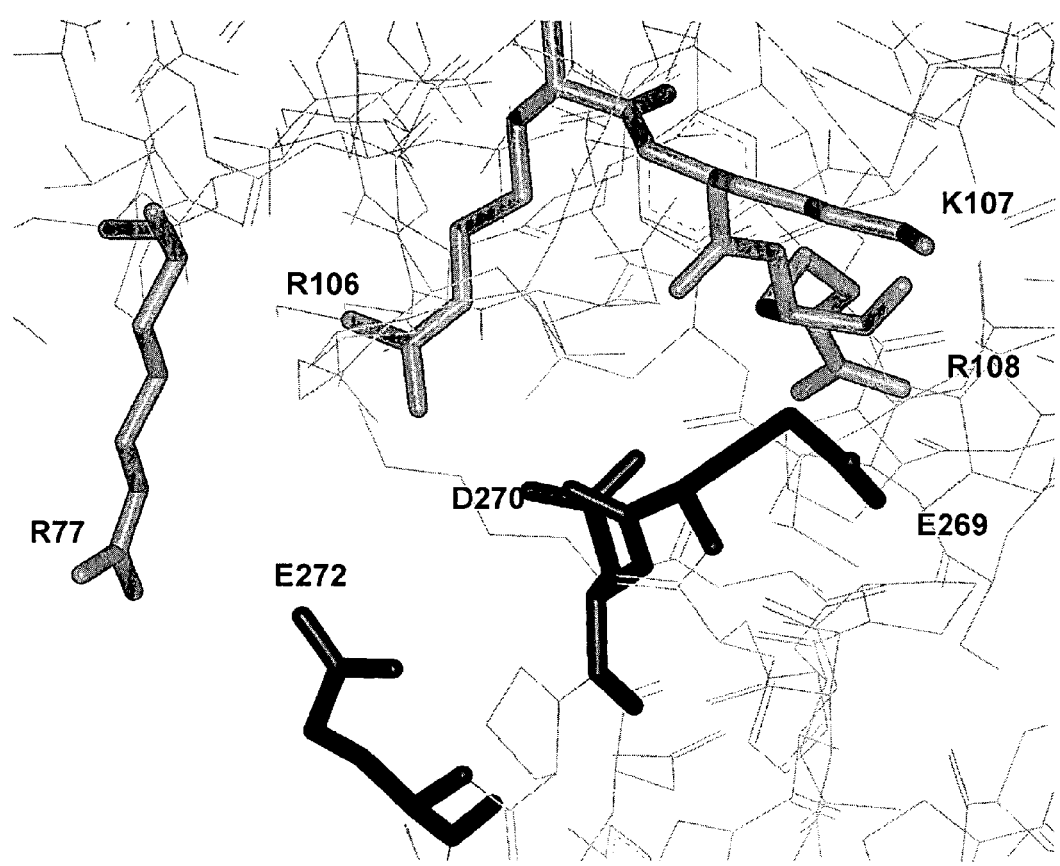
FIG. 7. The Fab/Fc interface in the 1HZH structure, showing interaction of positively charged Fab residues R77, R106, K107, and R108 (Kabat and 1HZH numbering) with negatively charged Fc residues E269, D270, and E272 (EU numbering scheme numbering, which correspond to 1HZH residues E282, D283, and E285 respectively).

Another set of data that suggests that there is more to the antibody/effector ligand interaction than the residues at the Fc/FcγR interface is the observation that a number of mutations at Fc residues distal to the Fc/FcγR interface affect affinity of the interaction (U.S. Ser. No. 10/672,280, U.S. Ser. No. 10/822,231, U.S. Ser. No. 60/627,774, and U.S. Ser. No. 60/642,477). FIG. 5a shows AlphaScreen data for binding to human V158 FcγRIIIa by Fc variants E272Y and K274E, carried out as described above. These substitutions significantly enhance the affinity of Fc for FcγRIIIa, in the case of E272Y by an order of magnitude. As shown in FIG. 5b, however, these residues, are distal to the Fc/FcγR interface. Thus it appears that these residues are playing some role in the Fc/FcγR binding event, but one which does not involve direct interaction at the interface. One possible explanation for the effect of these mutations on FcγR binding is suggested by visual inspection of the structure of a full length human antibody (pdb accession code 1HZH, Saphire et al., 2002, *J Mol Biol* 319:9-18). This structure, illustrated in FIG. 6a, shows that a full length antibody is not an extended structure as suggested by the model in FIG. 1, but rather has intra-molecular interactions between the Fab and Fc regions, shown in a closer view in FIG. 6b. Comparing the human complex structure in FIG. 6a with the Fc/FcγR complex structure in FIG. 2, it seems that the Fab/Fc interaction would sterically occlude binding of Fc to FcγRs, as well as potentially C1q based on the putative Fc/C1q binding site. E272 (EU numbering) in the 1IIS structure (Radaev et al., 2001, *J Biol Chem* 276:16469-16477) corresponds to position E285 in the 1HZH structure (the Fc sequences in the two structures must be been aligned to identify the corresponding residues). FIG. 7 provides a closeup view of the Fab/Fc binding site, showing that E272 in fact resides at the Fab/Fc interface and makes potential interactions with residues in the Fab region. Overall there is a substantial amount of charge complementarity at the interface, with a number of positively charged Fab residues (R77, R106, K107, and R108; Kabat and 1HZH numbering) facing a number of negatively charged Fc residues (E282, D283, and E285 in 1HZH, corresponding to EU numbering 269, 270, and 272 respectively). Notably, FcγRIIIa also has a number of positively charged residues that mediate interaction with Fc, further supporting the idea that the positively charged Fab competes with the positively charged FcγR for the negatively charged Fc.

Figure 8A:
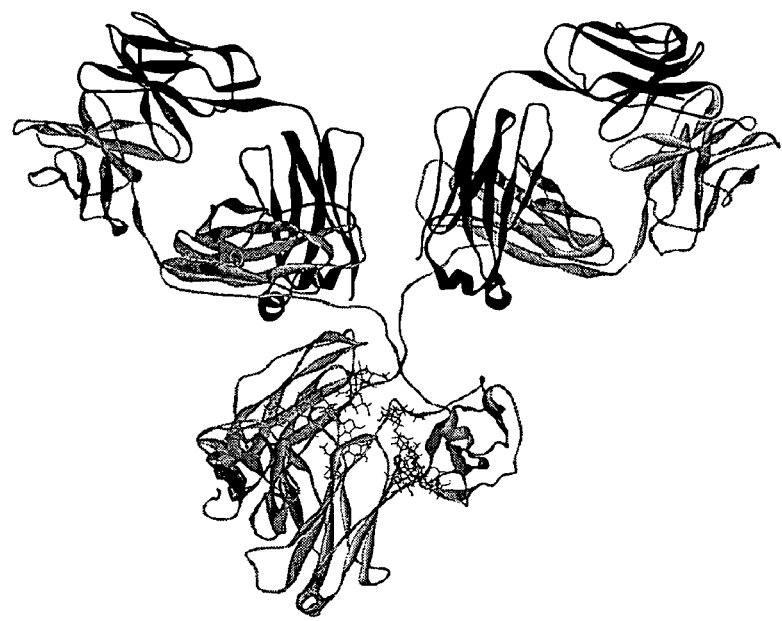
FIGS. 8a-8b. Full length antibody complex structures mAb 61.1.3, a murine IgG1 (pdb accession code 1GY, Harris et al., 1995, Nature 360:369-372) (FIG. 8a) and mAb 231, a murine IgG2a (pdb accession code 1GT, Harris et al., 1997, Biochemistry 36:1581-1597) (FIG. 8b). The heavy chains are shown as grey ribbon, the light chains are shown as black ribbon, and the carbohydrates are shown as black sticks.
Figure 8B:

Given the high degree of flexibility between the different antibody domains, the conformation of the binding interface may not be well-ordered, or may be one of an ensemble of Fab/Fc interaction conformations. Indeed there are a lower number of specific interactions in the 1HZH structure relative to other protein-protein interfaces, and two other structures of full length murine antibodies, shown in FIGS. 8a and 8b, also indicate intra-molecular interaction between Fab and Fc, but in different conformations (pdb accession code 1GY, Harris et al., 1995, *Nature* 360:369-372; pdb accession code 1GT, Harris et al., 1997, *Biochemistry* 36:1581-1597). Accordingly, discussion of E272 and K274 is not meant to imply that they are necessarily specific binding determinants of the Fab/Fc interaction, nor that electrostatics necessarily play the dominant role. Rather, these residues are provided to illustrate that a collection of loosely defined interactions may characterize the Fab/Fc binding event. Because Fab/Fc interaction is intramolecular, a substantial amount of the entropy cost binding has already been paid. Thus it is reasonable to suspect that a loose set of interactions, for example one or more clusters of electrostatic interactions, may provide sufficient energy to promote binding.

Figure 9A:
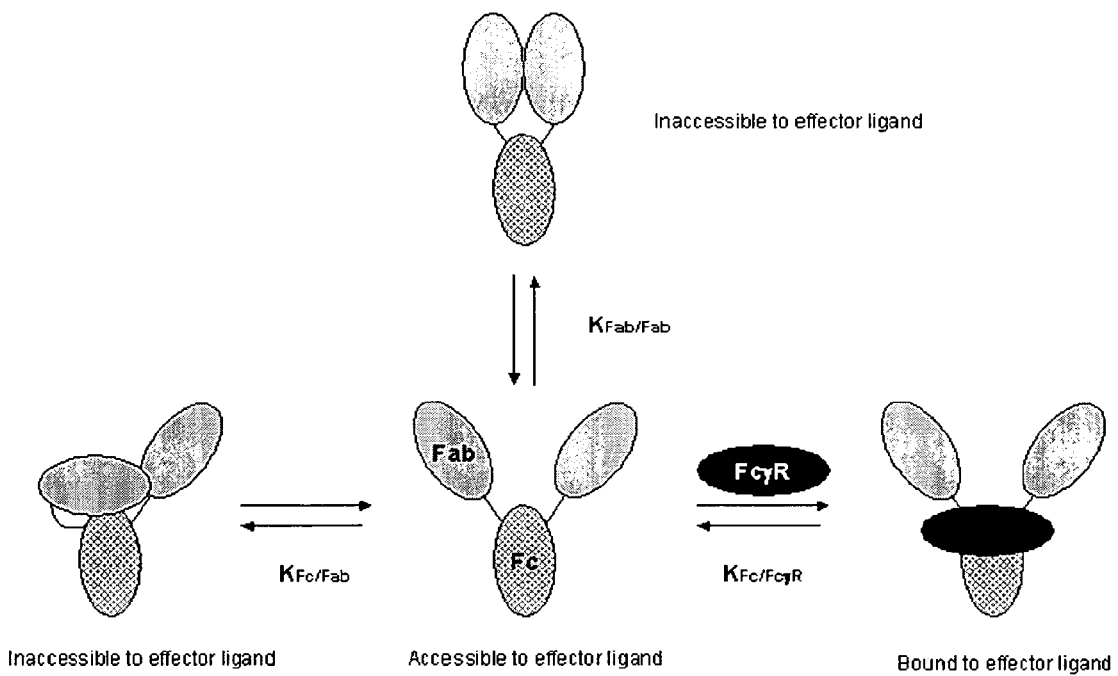
FIGS. 9a-9b. Models illustrating how residues outside the Fc region may affect interaction of the antibody with effector ligands.
Figure 9B:
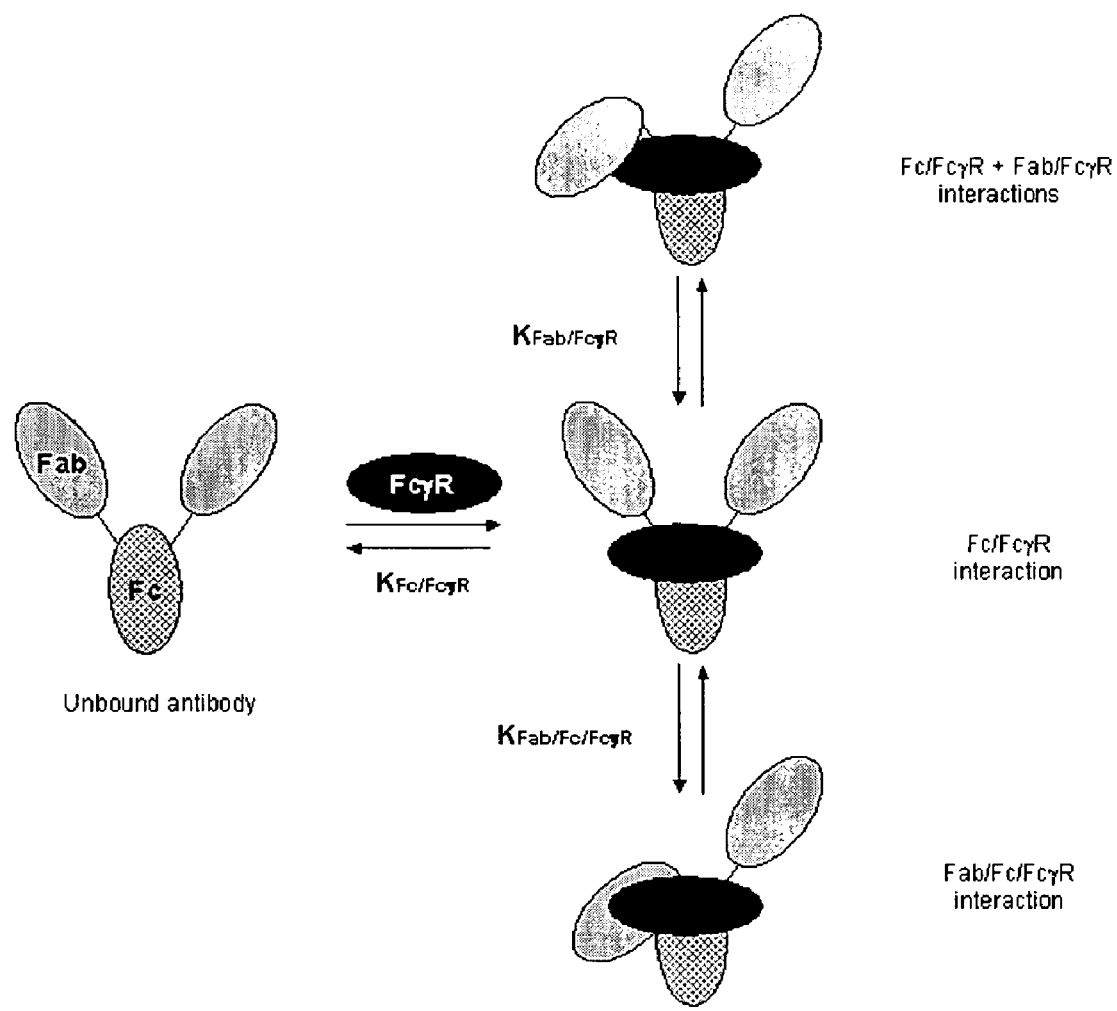

It follows that a possible explanation for the enhanced FcγR binding properties of E272Y and other Fc variants distal to the Fc/FcγR interface that enhance binding, is that by disrupting the favorable interaction between Fab and Fc, the equilibrium between them is disfavored, and thus Fc resides in an unbound state that is free to interact with FcγR. In effect, the Fab region competes with FcγR for binding to Fc. A model describing this inhibition hypothesis is illustrated in FIG. 9a. The unbound form of the antibody is in equilibrium with a set of mutually exclusive bound states— one wherein Fc is bound to effector ligand, and one wherein Fc is bound to Fab. The model shows additionally that perhaps interactions between the Fab regions may also exclude or compete for binding to effector ligand. The equilibrium constants that govern this system are $K_{Fc/Fab}$, which defines the equilibrium between Fc and Fab, $K_{Fab/Fab}$, which defines the equilibrium between Fab and Fab, and $K_{Fc/Fc\gamma R}$, which defines the equilibrium between Fc and FcγR. Thus different Fab and Fc sequences, although having limited impact on $K_{Fc/Fc\gamma R}$ directly, may affect the observed affinity of Fc/FcγR by altering KFC/Fab or $K_{Fab/Fab}$. An alternative to the inhibition model is one in which, rather than competing with effector ligand binding, the Fab region positively impacts effector ligand binding. This activation model is illustrated in FIG. 9b. In this model, the Fab region makes favorable interactions with FcγR, the Fc/FcγR complex, or both. Thus the Fab/FcγR+Fc/FcγR state and the Fab/Fc/FcγR state are more stable complexes than the Fc/FcγR state. These two models are meant to provide a hypothetical account for differences in Fc/FcγR binding observed between antibody variable regions and by Fc mutations distal to the Fc/FcγR interface. Although the models are shown with an FcγR as the effector ligand, they are meant to generally apply for any effector ligands as defined herein. For example it follows that, since the C1q site is proximal and overlapping with the FcγR binding site on Fc, the same models may apply to binding of Fc to C1q.

An implication of either of the proposed models is that they suggest that engineering substitutions in regions outside of the antibody Fc region may be a means to optimize effector ligand binding and effector function. As discussed, there are many possible reasons for the differing levels of effector function observed for therapeutic antibody, including but not limited expression level, availability, and accessibility of target antigen. The present invention suggests that another possible parameter determining the effector function of antibodies, and potentially in turn their clinical behavior, is the impact of the Fab and hinge region on interaction of the Fc region with effector ligands. It is contemplated that substitutions can be engineered into the Fab and hinge regions that modulate this effect, and thus favor or disfavor interaction of the antibody with effector ligands so that antibodies can be tuned for a desired clinical outcome.

Example 2

Engineered Variable Region Variants

As discussed, the flexibility between the Fab and Fc regions, as well as the differences between different antibody variable regions, may dictate that different antibodies have different Fab/Fc interactions. Thus although the available structures (1HZH, 1GY, and 1GT as described above) may provide information on the Fab/Fc interface, it may be imprudent to rely on this information as a definitive structural picture. Another important source of information is the structure activity relationship (SAR) data provided by different antibodies with different effector ligand affinities. For example, as described above, there exists some difference or differences between Campath and Herceptin in their variable regions that impact interaction of the antibody with FcγR. FIGS. 3a and 3b show alignments of the Campath and Herceptin VL and VH sequences respectively. These alignments highlight the differences between the two antibodies (shown in bold) that are putatively involved in determining their FcγR affinity differences. Thus one strategy for characterizing Fab/Fc interaction, and for designing variable region variants with altered effector ligand affinity and effector function, is to replace some or all of the residues in Herceptin with the corresponding residues in Campath. Substitutions may be engineered at FR positions, CDR positions, or both. Here, because Herceptin is the weaker FcγR binder, replacement of one or more residues with the corresponding Campath amino acid is expected to enhance FcγR.

Based on this strategy, a variant library was designed wherein for residues at which the two antibody variable regions differ, the Herceptin residue was replaced with the corresponding Campath-1G residue. Only surface exposed differences (determined by visual inspection of a modeled Herceptin structure) were considered in order not to perturb the stability of the variable region. Residues were grouped according to structural proximity to each other; CDR residues were grouped together accordingly (VL CDR1, VL CDR2, etc.), and were defined according to the structural definition of Chothia (Chothia & Lesk, 1987, *J. Mol. Biol.* 196: 901-917; Chothia et al., 1989, *Nature* 342: 877-883; Al-Lazikani et al., 1997, *J. Mol. Biol.* 273: 927-948). Table 2 provides a list of the designed VL and VH variants. In this library, VL1, VL2, and VL3 represent the light chain CDR differences between Herceptin and Campath-1G, VH1, VH2, and VH3 represent the heavy chain CDR differences, VL4 and VH4 provide the combined CDR differences for VL and VH respectively, and VL4-VH4 provides all mutated CDRs. Residues are numbered according to Kabat. Dashes denote deletions or insertions; for example, -52bK indicates an insertion of lysine at Kabat position 52b, and A100b- indicates a deletion of alanine at Kabat position 100b.

TABLE 2

Variable Region Variants

| Variant | Substitution(s) (Kabat numbering) |
|---|---|
| VL1 | D28N/N30D/T31K/A32Y |
| VL2 | S50N/A51T/S52N/F53N/Y55Q/S56T |
| VL3 | Y92I/T93S/T94R/P96R |
| VL4 | D28N/N30D/T31K/A32Y/S50N/A51T/S52N/F53N/Y55Q/S56T/Y92I/T93S/T94R/P96R |
| VL5 | Q3K/Q100T |
| VL6 | S10F |
| VL7 | T22N/R24K |
| VL8 | P40L/K42E/A43S |
| VL9 | R66G |
| VL10 | F83V/I106L |
| VL11 | Y87F |
| VL12 | K103A/E105A[a] |
| VL13 | K107A/R108A[a,b] |
| VH1 | N28T/K30T/T32F |
| VH2 | R50F/Y52R/P52aD/-52bK/-52cA/T53K/N54G/G55Y/Y56T |
| VH3 | W95E/G97H/D98T/G99A/F100A/Y100aP/A100b-[c] |
| VH4 | N28T/K30T/T32F/R50F/Y52R/P52aD/-52bK/-52cA/T53K/N54G/G55Y/Y56T/W95E/G97H/D98T/G99A/F100A/Y100aP/A100b-[c] |
| VH5 | Q3K/V5L |
| VH6 | L18M/A24G |
| VH7 | H35N |
| VH8 | A40P/P41A |
| VH9 | G44A/L45P |
| VH10 | R58E/A60N/D61P |
| VH11 | A71R |
| VH12 | T73N/S74T/K75Q/T77M |
| VH13 | S82bT |
| VH14 | V89T/T107V/L108M |
| VL4-VH4 | VL4 + VH4 |

[a]VL12 and VL13 are double alanine mutations at Herceptin K103 and E105, and K107 and R108 respectively, and are not differences between Herceptin and Campath-1G.
[b]Residue R108 is in the Cκ region, and numbering is according to the EU numbering scheme
[c]VH residues Herceptin M100d and Campath-1G F100d were aligned with the sequential JH region (see FIG. 3b), and as a result are not numbered according to Kabat.

Figure 10A:
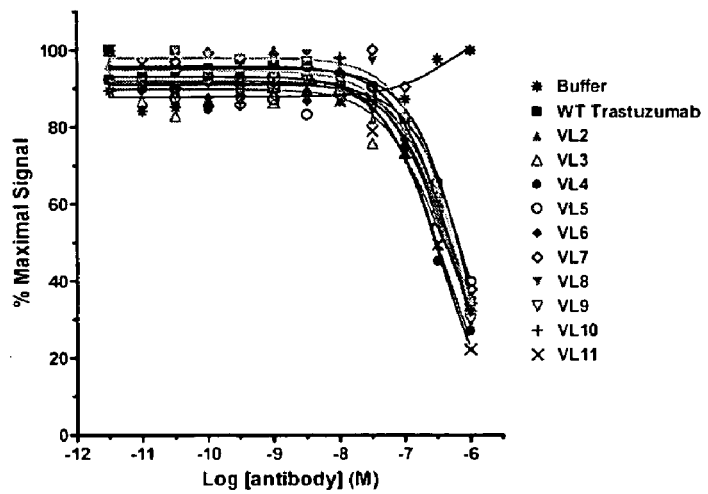
FIG. 10a-10c. Binding to human V158 FcγRIIa by VH and VL variants in the context of Herceptin as determined by the AlphaScreen assay. In the presence of competitor antibody, a characteristic inhibition curve is observed as a decrease in luminescence signal. Phosphate buffer saline (PBS) alone was used as the negative control. These data were normalized to the maximum and minimum luminescence signal provided by the baselines at low and high concentrations of competitor antibody respectively. The curves represent the fits of the data to a one site competition model using nonlinear regression.
Figure 10B:
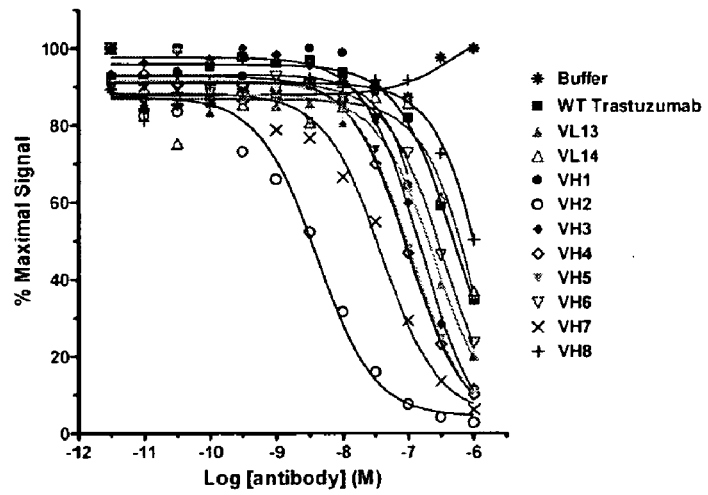
Figure 10C:
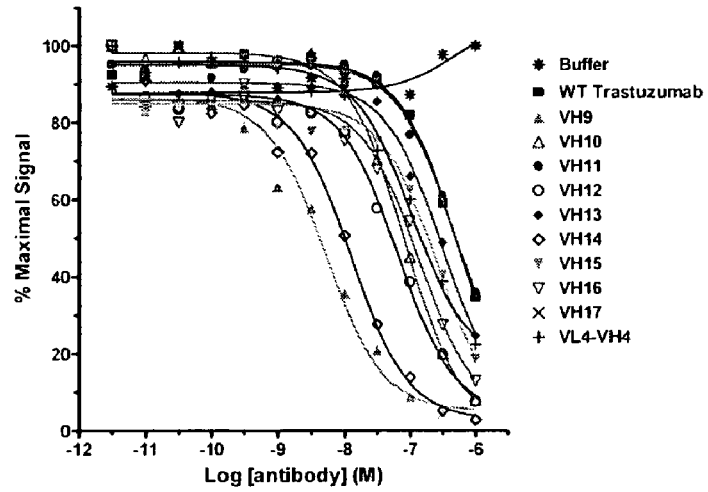
Figure 11:
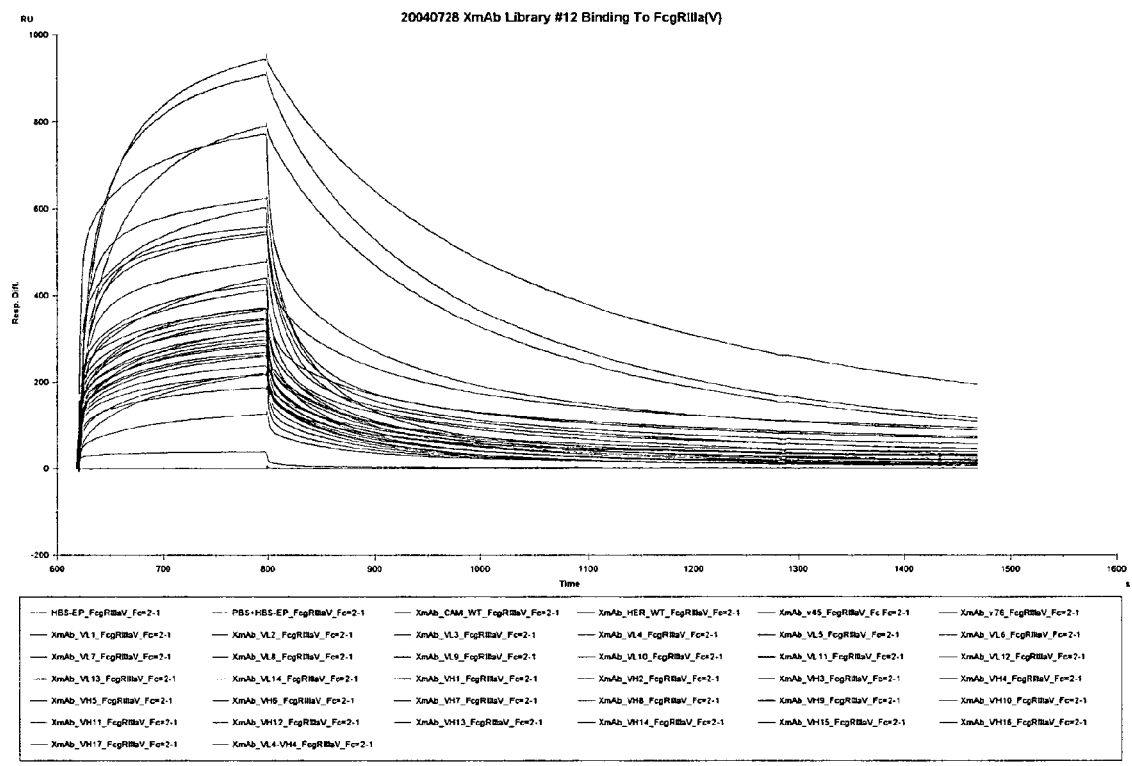
FIG. 11. SPR kinetic data curves. 5 ul of 200 nM FcγRIIIa(V158)-GST was injected at 1 ul/min over an anti-GST antibody flowcell, 1 uM antbody was flowed over the bound chip by KINJECT of 120 ul injection at 40 ul/min, followed by a dissociation time of 600 seconds. The chip was regenerated each cycle with 2 injections of 10 mM glycine, pH 1.5. Equilibrium constants (Kd's) from the fits to the data are provided in Table 3.
Figure 12:
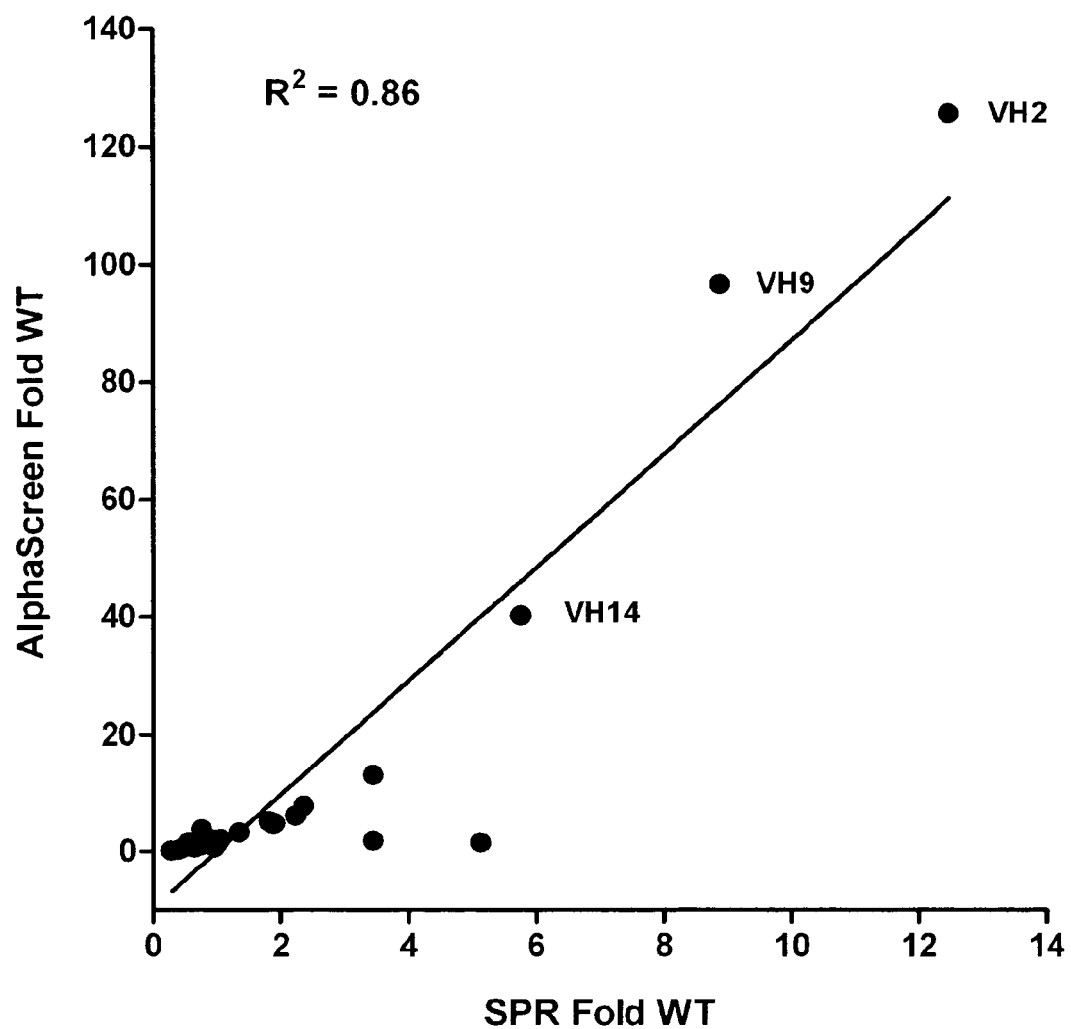
FIG. 12. Correlation between fold IC50's relative to WT obtained from the AlphaScreen and fold Kd's relative to WT obtained from SPR for binding of VH and VL Herceptin variants to human V158 FcγRIIIa.

These variants were constructed in the variable region of the antibody Herceptin in the pcDNA3.1Zeo vector using quick-change mutagenesis techniques (Stratagene), expressed in 293T cells, and purified as described above. Binding affinity to human FcγRIIIa was measured for the variants using the AlphaScreen assay as described above. The results, provided in FIG. 10, show that a number of the variants significantly enhance the binding of Herceptin to FcγRIIIa. The binding data were normalized to the maximum and minimum luminescence signal for each particular curve, provided by the baselines at low and high antibody concentrations respectively. The data were fit to a one site competition model using nonlinear regression, and these fits are represented by the curves in the figure. These fits provide the inhibitory concentration 50% (IC50) (i.e. the concentration required for 50% inhibition) for each antibody, enabling the relative binding affinities of Fc variants to be quantitatively determined. By dividing the IC50 for each variant by that of WT Herceptin, the fold-enhancement or reduction relative to WT Herceptin (Fold WT) were obtained. These values are provided in Table 3. Here a fold above 1 indicates an enhancement in binding affinity, and a fold below 1 indicates a reduction in binding affinity relative to WT Herceptin. The FcγR binding affinities of the variants were further investigated using Surface Plasmon Resonance (SPR) (Biacore, Uppsala, Sweden). FcγRIIIa(V158)-GST was immobilized to an SPR chip, and WT and variant Herceptin antibodies were flowed over the chip at a range of concentrations. FIG. 11 shows the raw data obtained from this set of binding experiments. Binding constants were obtained from fitting the data using standard curve-fitting methods. Table 3 presents dissociation constants (Kd) and Fold Kd relative to WT (Fold WT) for binding of select Fc variants to human V158 FcγRIIIa obtained using SPR, and compares these with IC50s obtained from the AlphaScreen assay. The correlation between Fold WT's obtained from the SPR and AlphaScreen binding measurements is shown in FIG. 12; the good fit of these data to a straight line (R=0.86) supports the accuracy of the data. The SPR data corroborate the improvements to FcγRIIIa affinity observed by AlphaScreen assay.

TABLE 3

| Antibody | AlphaScreen | | SPR | |
| --- | --- | --- | --- | --- |
| | IC50 (uM) | Fold WT | Kd (uM) | Fold WT |
| WT Herceptin | 0.502 | 1.00 | 1.44 | 1.00 |
| VL1 | | | 1.22 | 1.18 |
| VL2 | 0.346 | 1.45 | 2.58 | 0.56 |
| VL3 | 0.290 | 1.73 | 0.42 | 3.46 |
| VL4 | 0.352 | 1.43 | 0.28 | 5.15 |
| VL5 | 0.972 | 0.52 | 1.49 | 0.97 |
| VL6 | 0.524 | 0.96 | 1.88 | 0.77 |
| VL7 | 1.002 | 0.50 | 2.18 | 0.66 |
| VL8 | 0.727 | 0.69 | 2.54 | 0.57 |
| VL9 | 0.672 | 0.75 | 2.92 | 0.49 |
| VL10 | 0.392 | 1.28 | 2.04 | 0.71 |
| VL11 | 0.336 | 1.49 | 1.55 | 0.93 |
| VL12 | | | 2.14 | 0.68 |
| VL13 | 0.249 | 2.02 | 1.35 | 1.07 |
| VH1 | | | 4.98 | 0.29 |
| VH2 | 0.004 | 125.48 | 0.12 | 12.50 |
| VH3 | 0.158 | 3.17 | 1.06 | 1.36 |
| VH4 | 0.098 | 5.11 | 0.79 | 1.82 |
| VH5 | 0.111 | 4.51 | 0.76 | 1.90 |
| VH6 | 0.342 | 1.47 | 2.17 | 0.66 |
| VH7 | 0.039 | 12.98 | 0.42 | 3.46 |
| VH8 | 3.367 | 0.15 | 3.64 | 0.40 |
| VH9 | 0.005 | 96.53 | 0.16 | 8.90 |
| VH10 | 0.083 | 6.04 | 0.65 | 2.24 |
| VH11 | 0.446 | 1.12 | 1.51 | 0.95 |
| VH12 | 0.065 | 7.72 | 0.61 | 2.37 |
| VH13 | 0.308 | 1.63 | 1.67 | 0.87 |
| VH14 | 0.013 | 40.14 | 0.25 | 5.77 |
| VL4-VH4 | 0.106 | 4.74 | 0.75 | 1.92 |

Figure 13:
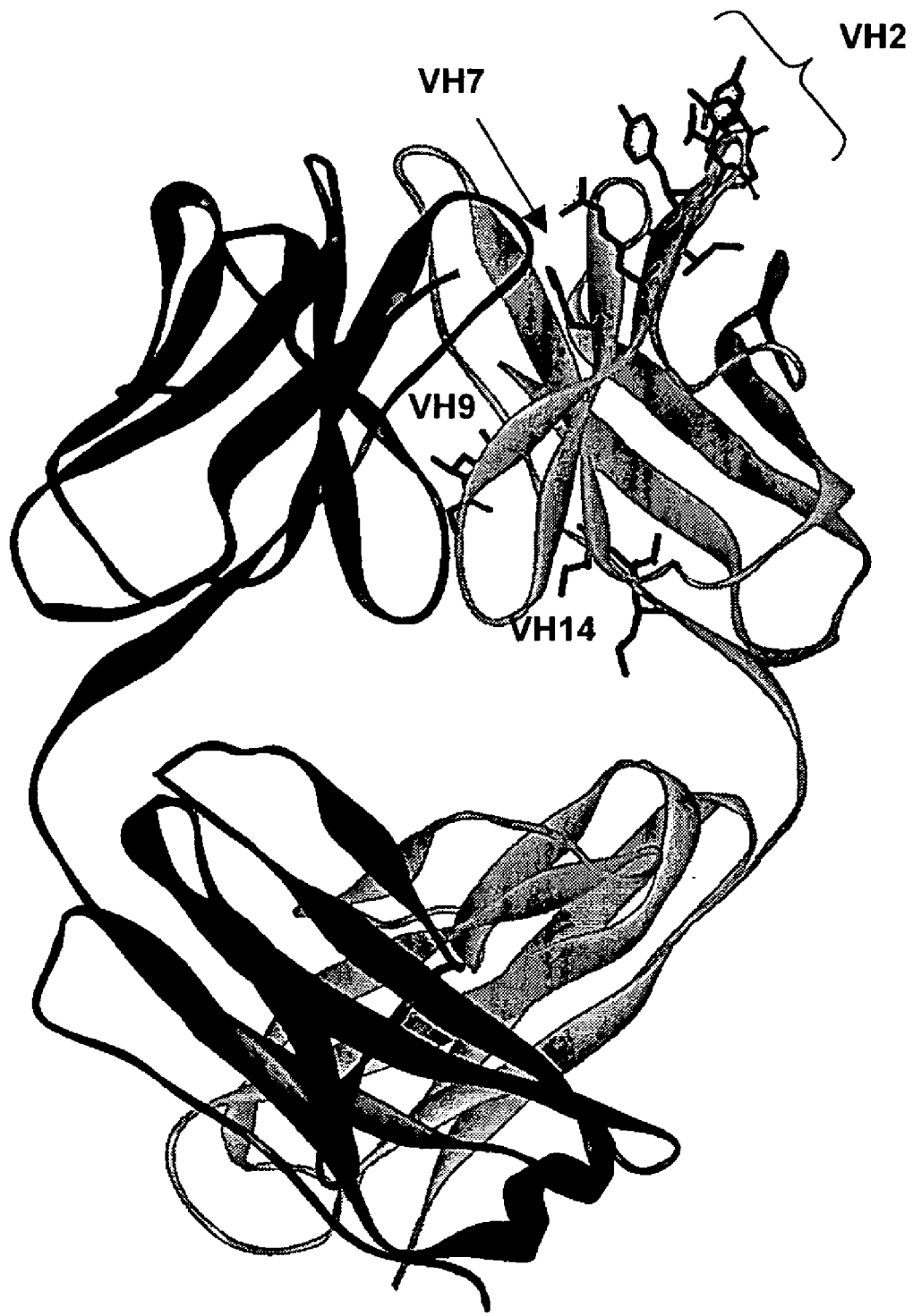
FIG. 13. Structure of Herceptin (pdb accession code 1FVE, Eigenbrot et al, 1993, J Mol Biol 229:969-995) showing residues mutated in variants VH2, VH7, VH9, and VH14. The VL and VH chains are shown as black and grey ribbon respectively.

In one embodiment, variants that bind FcγR with greater than 1-fold affinity relative to WT may be considered as providing improved or enhanced binding to an effector ligand. In a preferred embodiment, variants that bind with greater than 2-fold affinity may be considered. In a particularly preferred embodiment, variants that bind FcγR with greater than 3-fold affinity relative to WT may be considered as providing enhanced effector ligand binding. FIG. 13 shows 4 variants, VH2, VH7, VH9, and VH14, that provide greater than 10-fold FcγR affinity relative to WT, mapped onto the Herceptin Fab structure (pdb accession code 1FVE, Eigenbrot et al, 1993, J Mol Biol 229:969-995). The structure shows that the residues reside in VH CDR2 (variant VH2) and at or proximal to the interface between VL and VH (variants VH7, VH9, and VH14). The use of Campath and Herceptin sequences here is only an example, and is not meant to constrain the concept that variable region engineering can be used to modulate binding to effector ligands and effector function to these particular antibodies. The variable regions of other antibodies, particularly ones that show differential binding to effector ligands, may be used. For example, also included in FIGS. 3a and 3b are alignments of the VH and VL sequences of Rituxan and Erbitux, although any two or more antibodies can be used to generate modifications and tested as outlined here.

Indeed it may be that differences in effector ligand binding and effector function for different antibodies are not determined by simplistic rules, for example by specific variable region residues that consistently effector ligand binding for all antibodies. The implication here is that no set of mutations can be made in a Fab that are generally applicable for controlling the effector ligand affinity/specificity and effector function of all antibodies. A reasonable approach to this problem, and an embodiment of the present invention, is to characterize the effector ligand binding and effector function properties of groups of similar variable regions. In a most preferred embodiment, this concept is applied to the human variable region and J segment germline sequences. There are approximately 40 functional Vκ genes located on chromosome 2, about 30 functional Vλ genes on chromosome 22, and approximately 50 functional VH germline genes located on chromosome 14, along with 5 Jκ sequences, 7 Jλ sequences, and 6 JH sequences (Cox et al., 1994, Eur J Immunol 24:827-836; Barbie & Lefranc, 1998, Exp Clin Immunogenet 15:171-183; Williams et al., 1996, J Mol Biol 264:220-232; Kawasaki et al., 1997, Genome Res 7: 250-261; Pallares et al., 1998, Exp Clin Immunogenet 15:8-18; Tomlinson et al., 1992, J Mol Biol 227:776-798; Matsuda & Honjo, 1996, Advan Immunol 62:1-29; Matsuda et al., 1998, J Exp Med 188:2151-62; Scaviner et al., 1999, Exp Clin Immunogenet 16:234-40). The Vκ, Vλ, and VH germline sequences vary in size, and can be grouped into subfamilies based on sequence homology. There are approximately 7 VK subfamilies, 8-10 Vλ subfamilies, and 6-7 VH subfamilies; the binning into subfamilies is somewhat arbitrary, depending on how the homology cutoff between families is defined. The idea is to characterize the impact on effector ligand binding and/or effector function of each germline sequence, or given that the sequences within a given subfamily may behave similarly, each germline subfamily. Antibodies comprising the sequences, or one or more representative sequences from each subfamily, may be produced and screened experimentally to determine their binding affinity to FcγR, C1q, or other effector ligands, and/or their ability to mediate effector function in one or more cell-based ADCC, ADCP, and/or CDC assays. Ideally the constant regions in such an experiment would be the same between the different antibodies. The variable regions for these antibodies may comprise the germline sequences themselves, or may be naturally occurring antibodies that were derived from these sequences, determined for example by sequence homology. The end result would be that for each antibody germline sequence or each germline subfamily, the relative affinity for each effector ligand and the relative capacity to mediate each effector function would be known.

An important application of such information would be its use in immunogenicity reduction methods that are employed to replace nonhuman sequences (typically mouse and rat) in an antibody with sequences that are more common in humans. The dominant method in use for antibody immunogenicity reduction, referred to as "humanization", relies principally on the grafting of "donor" (typically mouse or rat) complementarity determining regions (CDRs) onto "acceptor" (human) VL and VH frameworks (FRs) (Tsurushita & Vasquez, 2004, Humanization of Monoclonal Antibodies, Molecular Biology of B Cells, 533-545, Elsevier Science (USA)). This strategy is referred to as "CDR grafting" (Winter U.S. Pat. No. 5,225,539). "Back-mutation" of selected acceptor framework residues to the corresponding donor residues is often required to regain affinity that is lost in the initial grafted construct (U.S. Pat. No. 5,530,101; U.S. Pat. No. 5,585,089; U.S. Pat. No. 5,693,761; U.S. Pat. No. 5,693,762; U.S. Pat. No. 6,180,370; U.S. Pat. No. 5,859,205; U.S. Pat. No. 5,821,337; U.S. Pat. No. 6,054,297; U.S. Pat. No. 6,407,213). Knowledge of the effector ligand affinity and effector function of individual germline variable region sequences and/or subfamilies would allow acceptor frameworks to be chosen based on the desired effector ligand affinity and specificity, and/or the desired degree of effector function.

A method that is particularly well suited for engineering variable regions with altered effector ligand properties is described in U.S. Ser. No. 11/004,590, filed Dec. 3, 2004, entitled "Methods of Generating Variant Proteins with Increased Host String Content and Compositions Thereof". This method reduces antibody immunogenicity by maximizing the content of human linear sequence strings, typically by utilizing the local sequence information contained in an alignment of human sequences. In this way immunogenicity is addressed at the local sequence level. This strategy provides a more accurate measure of the immunogenicity, and employs an optimal balance between binding determinants and humaness. With respect to effector ligand properties, the advantage of this method is that it samples a large diversity of local sequence and structure space, which is both quality in structure and stability and low in immunogenicity. Indeed, the effector ligand determinants in the variable region need not reside over the entire sequence, but rather may occur at the local level. By sampling this diversity, a library of stable, soluble, and low immunogenic variable region variants can be sampled, some of which may possess different effector ligand and effector function properties than others. Thus this method may be employed to optimize effector function during the immunogenicity reduction process, or to reengineer a variable region with suboptimal effector function such that it possesses more favorable effector function properties. The engineering and screening of multiple variable region sequences for their effector ligand and effector function properties, and further the use of this information as a criteria for evaluating clinical candidates, are embodiments of the present invention.

Example 3

Engineered JL, JH, CL, and CH1 Variants

In contrast to VH and VL sequences, the J segments encoding the C-termini of the variable regions and constant light and first constant heavy regions are more conserved among antibodies of the same class and among therapeutically useful antibodies. Thus residues within these regions that play a role in determining effector ligand affinity/specificity and effector function properties may be more consistent from antibody to antibody, and accordingly variants that alter these properties may be more generally applicable to therapeutically useful antibodies. In order to characterize the effector determinants in these regions of the Fab, and to generate variants that modulate effector ligand binding and effector function, substitutions were engineered using a computational, structure-based and sequence-based approach.

A set of computational structure-based design calculations were carried out to design point mutations that retain a stable, well-folded, structure using a design algorithm described generally as Protein Design Automation®) (PDA®) technology, as described in U.S. Pat. No. 6,188, 965; U.S. Pat. No. 6,269,312; U.S. Pat. No. 6,403,312; U.S. Ser. No. 09/782,004; U.S. Ser. No. 09/927,790; U.S. Ser. No. 10/218,102; PCT WO 98/07254; PCT WO 01/40091; and PCT WO 02/25588. These algorithms use an energy function with terms that include van der Waals forces, electrostatic forces, hydrogen bonding, desolvation interactions, and entropy. Other statistical energy terms include those based on known structures and those that compensate for effects on the unfolded state. Calculations were run using the 1.8 Å resolution structure of the anti-ErbB2 antibody Fab2C4 (pdb accession code 1L7I, Vajdos et al., 2002, J Mol Biol 320(2):415-28) as a structural template. The energies of all 20 natural amino acids were evaluated for all Jκ, JH, Cκ, and CH positions. The lowest energy rotamer conformation for all 20 amino acids was determined, and this energy was defined as the energy of substitution for that amino acid at that variable position. These calculations thus provided an energy of substitution for each of the 20 amino acids at each variable position. FIG. 14 shows the energy predictions from these calculations. In addition to computational screening calculations, sequence information was also used to guide variant design. Sequences encoding the human immunoglobulin kappa light J region (Jκ), lambda light J region (Jλ), heavy J region (JH), kappa light constant region (Cκ), lambda light constant region (Cλ), and IgG1-IgG4 gamma heavy constant regions (CH1, CH2, CH3, and CH4) were aligned, shown in FIG. 15. Additionally, visual inspection of the 1L7I Fab structure was used to identify residues that are surface exposed, boundary residues, core residues, and residues that reside at or may impact important binding interfaces, such as interfaces with other Ig domains in the Fab and the antigen binding interface. These positions are listed in FIG. 15. Together, these calculations, alignments, and structural analyses were used to design a set of variants, listed in FIG. 15.

Figure 16:
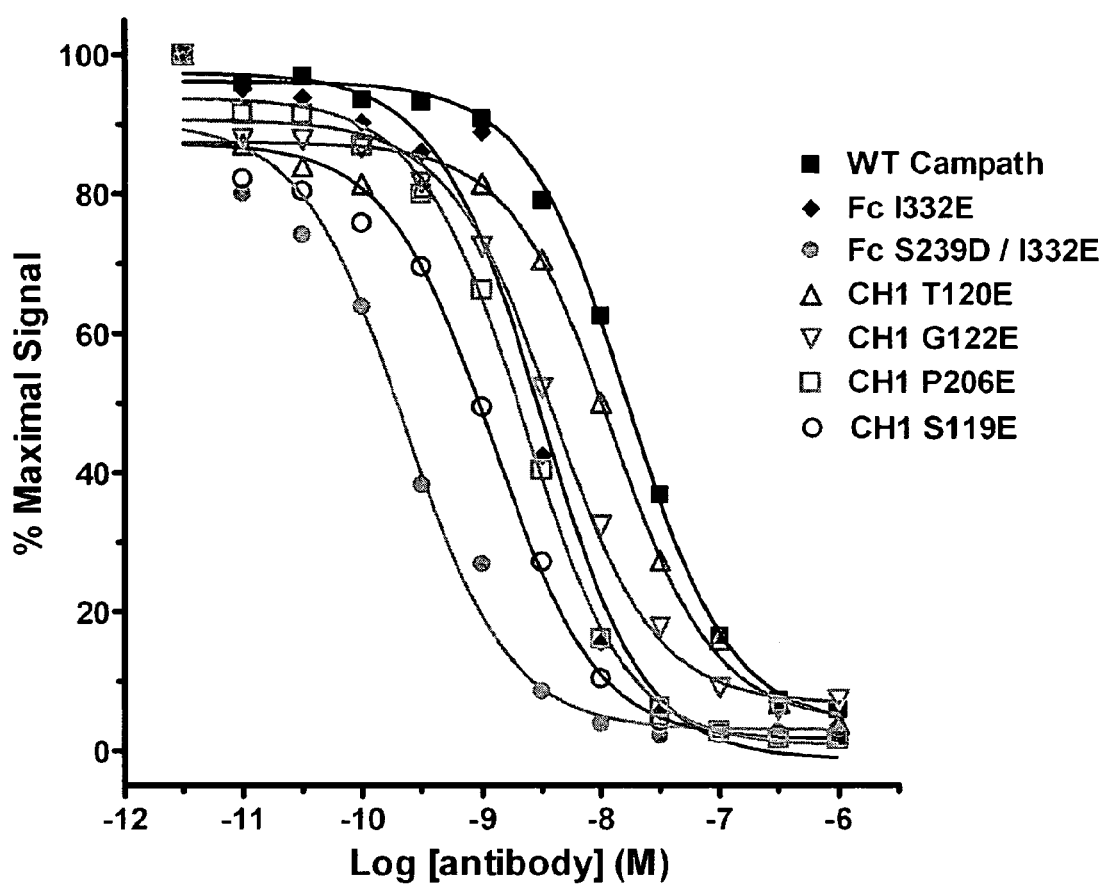
FIG. 16. Binding to human V158 FcγRIIa by select Fab variant and WT Campath antibodies as determined by the AlphaScreen assay. Also shown for comparison are two Fc variants, I332E and S239D/I332E, that have been previously been shown to enhance binding to FcγRIIIa and ADCC in a cell based assay. Numbering is according to the EU numbering scheme. Phosphate buffer saline (PBS) alone was used as the negative control. These data were normalized to the maximum and minimum luminescence signal provided by the baselines at low and high concentrations of competitor antibody respectively. The curves represent the fits of the data to a one site competition model using nonlinear regression.

Designed variants were constructed in the light and heavy chains of Campath in the pcDNA3.1Zeo vector using quick-change mutagenesis, expressed in 293T cells, and purified as described above. Binding affinity to human V158 FcγRIIIa, human F158 FcγRIIIa, and bacterial protein A were measured for the variants using the AlphaScreen assay as described above. FIG. 16 provides a representative data set from this series of binding assays, showing select Fab variants that enhance FcγR binding. Also shown for comparison are two Fc variants, I332E and S239D/I332E, that have been previously been shown to enhance binding to FcγRIIIa and ADCC in a cell based assay. Fold WT values for these data were generated as described above, and these are provided in Table 4. In this table, variants in the JL and JH regions are numbered according to the Kabat numbering scheme, and variants in the CL and CH1 regions are numbered according to the EU numbering scheme. Of particular importance are modifications that result in greater than 1-fold increase in affinity as compared to the wild-type (e.g. parent antibody) for any particular receptor. Thus, for example, in the JL and CL regions, all mutants exhibited better affinity to the RIIIa receptor than either of the "wild-types" tested. It is an aspect of the invention to provide modifications that provide higher affinity for at least one receptor.

TABLE 4

FcγR Binding Data for JL, JH, CL, and CH1 Variants

| Substitution(s) | Fold WT FcγRIIIa V158 | Fold WT FcγRIIIa F158 | ProtA |
|---|---|---|---|
| JL Region Kabat | | | |
| Q100P | 2.48 | 4.46 | |
| Q100G | 2.48 | 3.47 | |
| Q100K | 3.91 | 5.73 | |
| K103R | 3.54 | 5.62 | |
| K103D | 2.98 | 4.00 | |
| K103L | 4.28 | 6.90 | |
| E105D | 2.90 | 3.84 | |
| E105K | 12.36 | 21.88 | |
| E105I | 7.68 | 12.47 | |
| I106L | 6.05 | 8.94 | |
| K107E | 2.75 | 4.15 | |
| K107L | 2.22 | 3.00 | |
| JH Region Kabat | | | |
| Y102L | 1.58 | 2.34 | |
| Q105E | | | |
| Q105E | 0.99 | 1.21 | |
| Q105E | 0.90 | 0.85 | |
| Q105L | 1.48 | 1.69 | |
| S107T | 1.24 | 0.99 | |
| L108T | 1.39 | 1.21 | |
| L108E | 1.60 | 2.41 | |
| L108K | 1.10 | 1.15 | |
| T110K | 1.70 | 1.63 | |
| T110E | 2.03 | 2.95 | |
| T110I | 2.88 | 3.37 | |
| S112D | 3.77 | 6.18 | |
| S112K | 2.00 | 2.03 | |
| S112Y | 1.41 | 1.64 | |
| S113D | 4.11 | 6.10 | |
| S113R | 2.86 | 4.73 | |
| S113L | | | |
| CL Region EU | | | |
| R108Q | 3.64 | 5.47 | |
| R108D | 5.65 | 9.28 | |
| R108I | 8.97 | 16.24 | |
| T109P | 4.08 | 5.86 | |
| T109R | 3.98 | 5.59 | |
| T109D | 3.28 | 4.62 | |
| V110K | 5.31 | 8.95 | |
| V110E | 2.46 | 3.43 | |
| V110I | 2.06 | 2.90 | |
| A111K | 5.64 | 8.18 | |
| A111E | 5.57 | 9.45 | |

TABLE 4-continued

FcγR Binding Data for JL, JH, CL, and CH1 Variants

| Substitution(s) | Fold WT FcγRIIIa V158 | Fold WT FcγRIIIa F158 | ProtA |
|---|---|---|---|
| A111L | 2.90 | 4.11 | |
| A112R | 4.81 | 8.72 | |
| A112E | 5.34 | 8.70 | |
| A112Y | 6.96 | 11.48 | |
| S114D | 1.64 | 2.32 | |
| S114K | 3.35 | 5.06 | |
| S114I | 3.57 | 4.67 | |
| F116T | 2.25 | 3.30 | |
| S121D | 1.33 | 1.30 | |
| D122S | 2.67 | 3.09 | |
| D122R | | | |
| D122Y | 2.98 | 3.11 | |
| E123R | 2.32 | 3.17 | |
| E123L | 2.76 | 3.46 | |
| Q124E | 3.86 | 6.46 | |
| L125E | 4.18 | 5.79 | |
| L125K | 0.23 | 0.17 | |
| K126Q | 0.39 | 0.20 | |
| K126D | 0.44 | 0.29 | |
| K126L | 0.48 | 0.35 | |
| S127A | 0.70 | 0.55 | |
| S127D | | | |
| S127K | 0.42 | 0.27 | |
| G128N | 0.70 | 0.48 | |
| T129K | 0.76 | 0.51 | |
| T129E | 0.83 | 0.62 | |
| T129I | 1.28 | 0.78 | |
| S131T | 0.45 | 0.31 | |
| N137S | | | |
| N137K | 0.88 | 0.67 | |
| N138D | 0.84 | 0.55 | |
| N138K | 0.29 | 0.18 | |
| N138L | 0.53 | 0.48 | |
| Y140K | 0.74 | 0.56 | |
| Y140E | 1.40 | 0.95 | |
| Y140H | 1.91 | 1.47 | |
| P141K | 1.89 | 1.91 | |
| P141E | 1.26 | 0.98 | |
| R142G | 0.49 | 0.34 | |
| R142L | 0.39 | | |
| R142D | 0.72 | 0.52 | |
| E143A | 1.18 | 0.90 | |
| E143R | 1.48 | 0.94 | |
| E143L | 1.22 | 0.80 | |
| K145T | 1.07 | 0.79 | |
| K145D | 0.65 | 0.53 | |
| K145Y | 1.64 | 1.43 | |
| Q147A | 3.35 | 2.71 | 1.41 |
| Q147E | 3.21 | 3.12 | 1.55 |
| Q147K | 3.83 | 3.53 | 1.26 |
| K149D | 5.19 | | |
| K149Y | 2.57 | 2.42 | 1.19 |
| V150A | 3.17 | 2.70 | 1.05 |
| D151K | 10.51 | 9.83 | 1.39 |
| D151I | 1.71 | 1.36 | 1.27 |
| N152S | 4.09 | 3.26 | 1.07 |
| N152R | 2.61 | 2.27 | 1.01 |
| N152L | 3.52 | 3.31 | 1.29 |
| A153S | 1.62 | 1.92 | 0.96 |
| A153D | 2.55 | 2.12 | 1.24 |
| A153H | 3.34 | 2.45 | 1.11 |
| L154V | 2.33 | 1.68 | 1.21 |
| L154E | 3.14 | 2.33 | 1.10 |
| L154R | 2.66 | 2.33 | 1.11 |
| Q155K | 4.27 | 3.47 | 1.35 |
| Q155E | 3.19 | 2.90 | 1.61 |
| Q155I | 2.49 | 2.21 | 1.39 |
| S156A | 4.01 | 3.75 | 1.42 |
| S156D | 1.96 | 1.63 | 1.44 |
| S156R | 3.61 | 2.51 | 1.53 |
| G157N | 1.24 | 0.95 | 2.32 |
| N158R | 4.05 | 2.83 | 1.79 |

TABLE 4-continued

FcγR Binding Data for JL, JH, CL, and CH1 Variants

| Substitution(s) | FcγRIIIa V158 (Fold WT) | FcγRIIIa F158 (Fold WT) | ProtA |
|---|---|---|---|
| N158D | 5.00 | 4.44 | 1.82 |
| N158L | | | |
| S159K | 11.29 | 9.34 | 2.40 |
| S159E | 3.88 | 3.91 | 1.20 |
| S159L | 5.49 | 5.21 | 1.23 |
| Q160V | 0.87 | 0.92 | 1.25 |
| Q160K | | | |
| E161K | 1.19 | 1.45 | 0.93 |
| E161L | 0.76 | 0.80 | 0.88 |
| S162T | 0.95 | 0.94 | 1.27 |
| V163T | | | |
| V163K | 0.98 | 1.02 | 0.79 |
| V163E | 0.93 | 1.19 | 1.02 |
| T164Q | 2.40 | 2.60 | 1.41 |
| E165P | 2.40 | 2.51 | 1.17 |
| E165K | 1.42 | 1.53 | 1.07 |
| E165Y | | | |
| Q166S | 0.94 | 0.39 | 1.04 |
| Q166E | 0.67 | 0.90 | 1.01 |
| Q166M | 0.52 | 0.49 | 0.99 |
| D167K | 0.53 | 0.58 | 1.62 |
| D167L | 0.44 | 0.52 | 1.04 |
| S168Q | 0.48 | 0.43 | 1.11 |
| S168K | 0.41 | 0.34 | 2.48 |
| S168Y | | | |
| K169S | | | |
| K169H | | | |
| K169D | | | |
| D170N | 0.80 | 0.71 | 1.26 |
| D170R | 0.45 | 0.45 | 0.94 |
| D170I | 0.74 | 0.82 | 0.73 |
| S171N | 1.21 | 0.65 | 1.20 |
| S171A | 0.83 | 0.91 | 1.22 |
| S171V | 0.95 | 1.03 | 1.15 |
| T172K | 0.62 | 1.84 | 1.24 |
| T172I | 1.20 | 1.40 | 1.01 |
| T172E | 1.12 | 1.41 | 1.01 |
| Y173K | 1.04 | 2.54 | 1.30 |
| Y173Q | 1.35 | 1.52 | 1.00 |
| Y173L | 1.08 | 1.18 | 0.73 |
| S174A | 0.63 | 0.81 | 1.30 |
| S176T | 0.45 | 0.39 | 1.11 |
| T180S | 0.25 | 0.87 | 0.99 |
| T180K | 0.84 | 1.00 | 0.81 |
| T180E | 0.71 | 0.55 | 1.09 |
| L181K | | | 1.09 |
| S182T | 0.76 | 0.82 | |
| S182E | 0.83 | 0.86 | |
| S182R | 0.55 | 1.17 | 0.94 |
| K183P | 0.74 | 0.46 | 1.04 |
| K183D | 0.52 | 0.65 | 1.00 |
| K183L | 0.60 | 0.45 | 1.03 |
| A184E | 0.61 | 0.64 | 0.82 |
| A184K | 0.43 | 0.72 | 1.21 |
| A184Y | 0.76 | 0.87 | |
| D185Q | | | |
| D185R | | | |
| D185I | 0.58 | 4.86 | 1.08 |
| E187K | 0.46 | 0.40 | |
| E187Y | 0.52 | 0.49 | 1.10 |
| K188S | 1.05 | 0.69 | 1.11 |
| K188E | 0.84 | 1.14 | 0.97 |
| K188Y | 1.89 | 0.98 | 1.30 |
| H189D | 0.63 | 1.33 | 1.22 |
| H189K | 0.27 | 0.02 | 0.87 |
| H189Y | 0.16 | 0.01 | 0.89 |
| K190R | 0.15 | 0.02 | 0.97 |
| K190E | 0.07 | 0.03 | 1.00 |
| K190L | 0.31 | 0.03 | 1.03 |
| V191S | 0.35 | 0.03 | 1.32 |
| V191E | 0.52 | 0.03 | 1.24 |
| V191R | 2.30 | 4.00 | 1.20 |
| A193S | 0.30 | 0.02 | 1.06 |
| A193E | | | |
| A193K | 0.21 | 0.03 | 1.10 |
| E195Q | 0.19 | 0.03 | 1.01 |
| E195K | 17.77 | 7.43 | 4.93 |
| E195I | 0.60 | 0.81 | 1.09 |
| T197E | | | |
| T197K | 0.28 | 0.02 | 1.06 |
| T197L | | | |
| Q199E | 0.26 | 0.01 | 1.08 |
| Q199K | 0.45 | 0.03 | 1.23 |
| Q199Y | 0.52 | 1.04 | 1.01 |
| G200S | 0.16 | 0.01 | 1.00 |
| S202D | 0.21 | 0.01 | 0.98 |
| S202R | 0.18 | 0.02 | 1.13 |
| S202Y | 0.17 | 0.02 | 1.12 |
| S203D | 0.06 | 0.01 | 1.02 |
| S203R | 0.33 | 0.01 | 1.05 |
| S203L | 5.58 | | |
| P204T | 0.31 | 0.03 | 1.10 |
| V205E | 0.46 | 0.03 | 1.35 |
| V205K | 0.16 | 0.01 | 1.03 |
| T206E | 0.31 | 0.02 | |
| T206K | 0.18 | 0.02 | 0.92 |
| T206I | 0.23 | 0.05 | 1.05 |
| K207E | 0.06 | 0.02 | 1.00 |
| K207L | 4.10 | 5.90 | 1.10 |
| S208T | 4.40 | 9.60 | 1.10 |
| S208E | | | |
| S208K | | | |
| N210A | | | |
| N210E | 3.10 | 3.10 | 0.90 |
| N210K | | | |
| R211P | | | |
| R211E | | | |
| G212T | | | |
| G212K | | | |
| G212E | 8.30 | 5.30 | 1.40 |
| E213R | 5.30 | 4.00 | 0.80 |
| E213L | | | |
| K207A/ R211A* | 0.32 | | |
| CH1 Region EU | | | |
| A118K | 2.80 | 4.52 | |
| A118E | 2.67 | 3.61 | |
| A118Y | 3.00 | 3.68 | |
| S119R | 2.22 | 2.54 | |
| S119E | 11.81 | 15.89 | 3.39 |
| S119Y | 1.67 | 2.22 | |
| T120R | 2.41 | 2.93 | |
| T120E | 3.62 | 5.55 | |
| T120I | 1.50 | 1.67 | |
| K121E | 2.06 | 2.83 | |
| K121Y | 1.62 | 1.62 | |
| K121H | 2.89 | 3.95 | |
| G122E | 4.17 | 5.31 | |
| G122R | 1.41 | | |
| S124K | 1.33 | 1.66 | |
| S124E | 1.43 | 1.46 | |
| S124Y | 0.62 | 0.55 | |
| F126K | 0.79 | 0.62 | |
| F126D | | | |
| A129L | 0.72 | 0.74 | |
| A129D | 0.78 | 0.67 | |
| S131G | 0.60 | 0.51 | |
| S131T | 0.38 | 0.38 | |
| S132D | 1.12 | 1.20 | |
| S132R | 0.45 | | |
| S132L | 0.72 | 0.53 | |
| K133R | 0.84 | 0.70 | |

TABLE 4-continued

FcγR Binding Data for JL, JH, CL, and CH1 Variants

| Substitution(s) | Fold WT | | |
|---|---|---|---|
| | FcγRIIIa V158 | FcγRIIIa F158 | ProtA |
| K133E | 0.83 | 0.62 | |
| K133L | 0.38 | 0.33 | |
| T135I | 0.61 | 0.48 | |
| T135E | 0.76 | 0.64 | |
| T135K | 0.63 | 0.37 | |
| S136E | 0.56 | 0.46 | |
| S136K | 0.43 | 0.30 | |
| S136I | 0.76 | 0.59 | |
| G137E | 0.64 | 0.50 | |
| G138S | 1.04 | 1.08 | |
| G138R | 0.69 | 0.65 | |
| G138D | 0.90 | 0.80 | |
| T139I | 0.65 | 0.53 | |
| T139E | 0.92 | 0.76 | |
| T139K | 0.66 | 0.52 | |
| K147A | 0.68 | 0.59 | |
| K147E | 0.65 | 0.41 | |
| D148Y | 0.73 | 0.83 | |
| D148K | 0.90 | 0.80 | |
| F150L | 0.57 | 0.44 | |
| F150K | 0.70 | 0.53 | |
| F150E | 0.54 | 0.52 | |
| P151A | 0.47 | 0.41 | |
| P151D | | | |
| E152L | 0.44 | 0.31 | |
| E152K | 0.50 | 0.50 | |
| P153L | 0.54 | 0.69 | |
| P153D | 1.03 | 1.34 | |
| T155E | 0.61 | 0.81 | |
| T155K | 0.72 | 0.65 | |
| T155I | 0.66 | 0.70 | |
| S157E | | | |
| S157K | 0.30 | 0.32 | |
| S157Y | 0.53 | 0.60 | |
| N159K | 0.45 | 0.41 | |
| N159D | 0.52 | 0.49 | |
| N159L | 0.39 | 0.44 | |
| S160K | 0.66 | 0.55 | |
| S160E | 0.76 | 0.45 | |
| S160Y | 0.59 | 0.44 | |
| G161D | 0.66 | 0.41 | |
| A162D | 0.79 | 0.47 | |
| A162K | | | |
| A162Y | 0.65 | 0.36 | |
| L163R | 0.87 | 0.48 | |
| T164R | 0.70 | 0.32 | |
| T164E | 0.53 | 0.30 | |
| T164Y | 0.70 | 0.41 | |
| S165D | 0.67 | 0.37 | |
| S165R | 0.67 | 0.45 | |
| S165Y | | | |
| G166D | 0.76 | 0.47 | |
| V167A | 0.46 | 0.39 | |
| H168L | 0.98 | 1.05 | |
| T169E | | | |
| P171G | 0.51 | 0.34 | |
| P171H | 2.14 | 1.52 | |
| A172K | 0.42 | 0.37 | |
| A172L | 0.54 | 0.37 | |
| A172E | 0.58 | 0.41 | |
| V173T | 0.63 | 0.65 | |
| V173D | 0.47 | 0.37 | |
| L174E | 0.93 | 0.89 | |
| L174K | | | |
| L174Y | 1.73 | 1.71 | |
| Q175D | 0.67 | 0.52 | |
| Q175L | 0.58 | 0.47 | |
| S176D | 0.66 | 0.54 | |
| S176R | 0.74 | 0.70 | |
| S176L | 0.67 | 0.73 | |
| S177R | 0.67 | 0.51 | |
| S177E | 1.00 | 0.87 | |
| S177Y | 0.81 | 0.62 | |
| G178D | 0.73 | 0.57 | |
| L179K | 0.66 | 0.67 | |
| L179Y | | | |
| L179E | 0.70 | 0.48 | |
| Y180K | 0.58 | 0.46 | |
| Y180L | 0.61 | 0.59 | |
| Y180E | 0.47 | 0.37 | |
| S183T | 2.11 | 1.02 | |
| T187I | 0.60 | 0.47 | |
| T187K | 0.42 | 0.35 | |
| T187E | 0.50 | 0.41 | |
| V188I | 0.40 | 0.33 | |
| P189D | 0.69 | 0.65 | |
| P189G | 0.24 | 0.16 | |
| S190I | 0.50 | 0.53 | |
| S190K | 0.32 | 0.34 | |
| S190E | 0.55 | 0.44 | |
| S191D | 0.52 | 0.43 | |
| S191R | 0.54 | 0.56 | |
| S191Y | 0.51 | 0.44 | |
| S192N | 0.67 | 0.62 | |
| S192R | 0.69 | 0.69 | |
| S192L | 0.32 | 0.29 | |
| L193F | 0.57 | 0.51 | |
| L193E | 0.72 | 0.58 | |
| G194R | 0.63 | 0.54 | |
| G194D | 0.79 | 0.70 | |
| T195R | 0.29 | 0.29 | |
| T195D | 0.53 | 0.41 | |
| T195Y | 0.38 | 0.31 | |
| Q196K | 0.26 | 0.29 | |
| Q196D | 0.40 | 0.45 | |
| Q196L | 0.42 | 0.29 | |
| T197R | 0.40 | 0.34 | |
| T197E | 0.44 | 0.41 | |
| T197Y | 0.47 | 0.51 | |
| Y198L | 1.04 | 1.11 | |
| I199T | 0.37 | 0.26 | |
| I199D | 0.32 | 0.34 | |
| I199K | 0.31 | 0.30 | |
| N201A | 2.23 | 3.47 | |
| N201K | 0.87 | 0.94 | |
| N201L | 0.77 | 1.06 | |
| N203D | 0.87 | 0.87 | |
| N203L | | | |
| N203K | 0.93 | 1.10 | |
| K205D | 1.84 | 2.35 | |
| K205L | 1.18 | 1.43 | |
| P206A | 1.44 | 1.71 | |
| P206E | 7.35 | 9.55 | 2.55 |
| S207K | 1.02 | 1.05 | |
| S207D | 1.15 | 1.43 | |
| N208R | 0.62 | 1.01 | |
| N208E | 1.74 | | |
| N208Y | 0.93 | | |
| T209E | 0.86 | 0.78 | |
| T209K | 0.90 | 1.04 | |
| T209Y | 0.87 | 1.21 | |
| K210L | 0.83 | 0.86 | |
| K210E | 0.40 | | |
| K210Y | 1.45 | | |
| V211R | 1.23 | 1.49 | |
| V211E | 0.97 | 1.05 | |
| V211Y | 1.21 | 1.70 | |
| D212Q | 0.40 | | |
| D212K | 0.73 | | |
| D212H | 0.30 | | |
| D212L | 0.53 | | |
| D212Y | 0.29 | | |
| K213N | 0.84 | | |
| K213E | 0.79 | | |

TABLE 4-continued

FcγR Binding Data for JL, JH, CL, and CH1 Variants

| Substitution(s) | Fold WT | | |
|---|---|---|---|
| | FcγRIIIa V158 | FcγRIIIa F158 | ProtA |
| K213H | 1.13 | | |
| K213L | 0.66 | | |
| K213Y | 0.34 | | |
| K214N | 1.20 | | |
| K214E | 1.43 | | |
| K214H | 0.84 | | |
| K214L | | | |
| K214Y | 1.53 | | |
| E216N | 0.30 | | |
| E216K | 2.04 | | |
| E216H | 0.68 | | |
| E216L | | | |
| E216Y | 1.12 | | |
| P217D | 1.22 | | |
| P217H | 0.19 | | |
| P217A | 0.94 | | |
| P217V | 1.56 | | |
| P217G | 1.21 | | |
| K218D | 1.17 | | |
| K218E | 0.66 | | |
| K218Q | 1.19 | | |
| K218T | | | |
| K218H | | | |
| K218L | | | |
| K218Y | | | |
| S219D | | | |
| S219E | | | |
| S219Q | | | |
| S219K | | | |
| S219T | | | |
| S219H | | | |
| S219L | | | |
| S219I | 0.27 | | |
| S219Y | | | |
| K205A/K210A* | 1.97 | | |
| K213A/K214A/K218A* | 3.70 | | |

Figure 17:
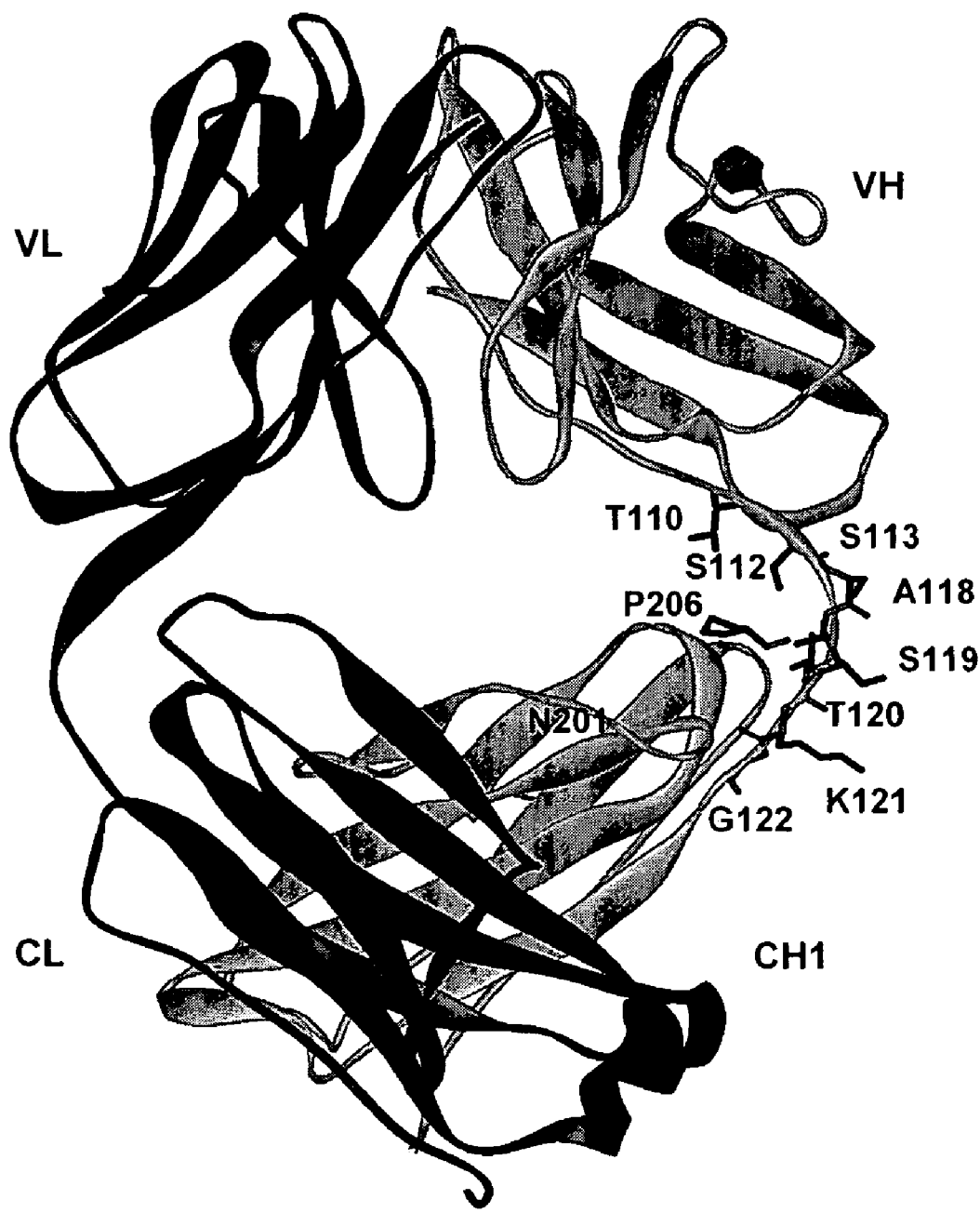
FIG. 17. Structure of a human Fab (pdb accession code 1L71) highlighting Fab heavy chain residues at which mutation provides enhanced FcγR binding. The light chain (VL-CL) is shown in black, and the heavy chain (VH-CH1) is shown in grey. Residues on the heavy chain at which single substitution results in FcγR binding greater than 3-fold relative to WT are shown as black sticks. Numbering is according to Kabat or EU numbering schemes as indicated in Table 4.
Figure 18:
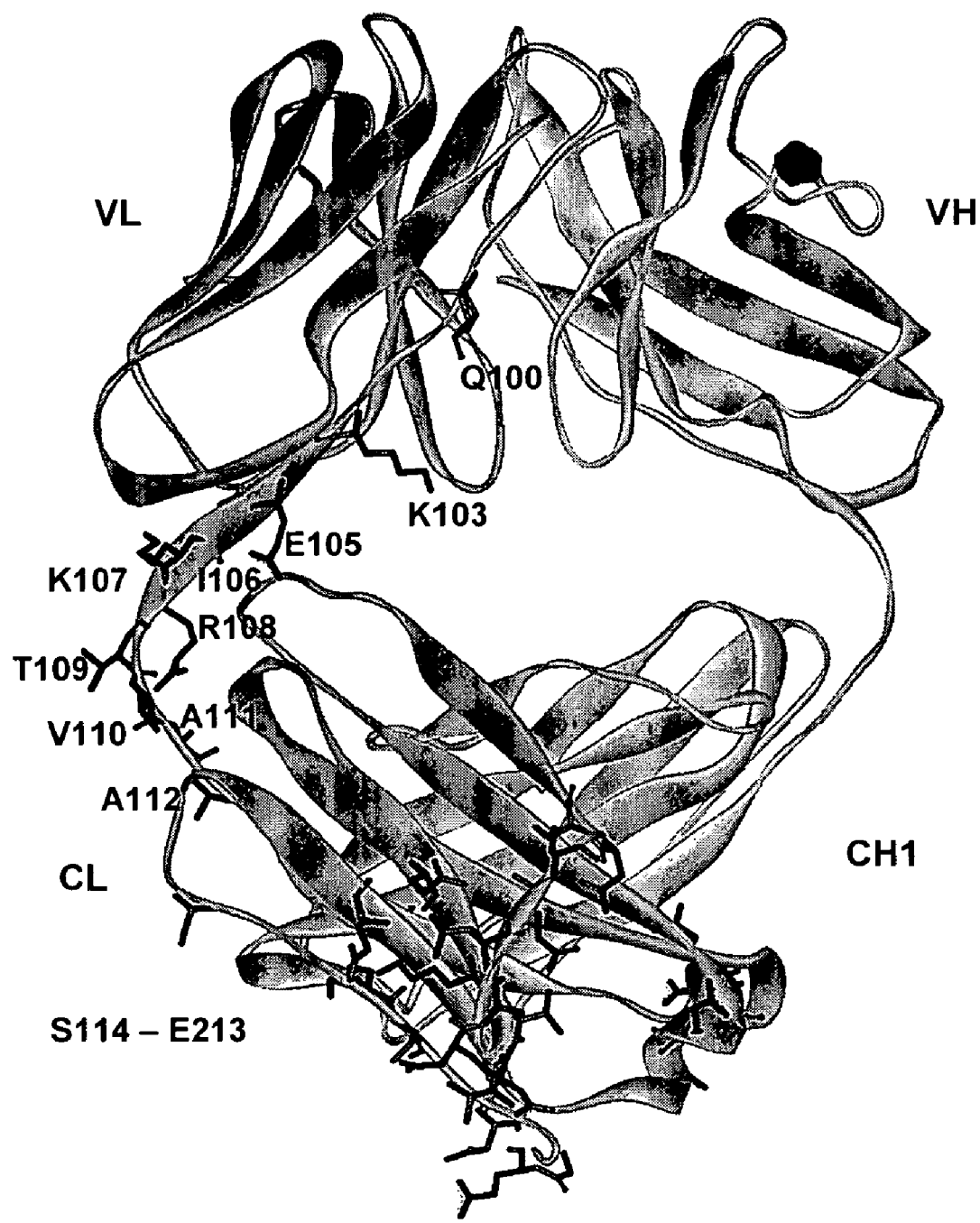
FIG. 18. Structure of a human Fab (pdb accession code 1L71) highlighting Fab light chain variants with enhanced FcγR binding. The light chain (VL-CL) is shown in dark grey, and the heavy chain (VH-CH1) is shown in light grey. Residues on the light chain at which single substitution results in FcγR binding greater than 3-fold relative to WT are shown as black sticks. Numbering is according to Kabat and EU numbering schemes as indicated in Table 4.

*CL double variant K207A/R211A, and CH1 double and triple variants K205A/K210A and K213A/K214A/K218A were designed in the context of Herceptin, not Campath On the heavy chain, a number of variants show significant improvements in FcγRIIIa binding. In one embodiment, variants that bind FcγR with greater than 1-fold affinity relative to WT may be considered as providing improved or enhanced binding to an effector ligand. In a preferred embodiment, variants that bind with greater than 2-fold affinity may be considered. In a particularly preferred embodiment, variants that bind FcγR with greater than 3-fold affinity relative to WT may be considered as providing enhanced effector ligand binding. For example, mutation variants T110I, S112D, S113D, S113R (Kabat numbering) in the JH region of the VH domain, and A118K, A118E, A118Y, S119E, T120E, K121H, G122E, N201E, and P206E (EU numbering) in the first heavy constant domain (CH1) all show greater than 3-fold FcγR binding relative to WT. FIG. 17 shows these residues mapped onto the heavy chain of the 1L71 Fab structure. As can be seen, these residues residue in and around the interface between the VH and Cγ1 domain. Particularly striking is that P206E, which shows a substantial enhancement in binding to FcγRIIIa, is distal in sequence to the other residues yet very close structurally. On the light chain, a number of variants show significant improvements in FcγRIIIa binding. For example, a number of single mutation variants show greater than 3-fold FcγR binding relative to WT, including Q100P, Q100G, Q100K, K103R, K103D, K103L, E105D, E105K, E105K, E105I, E105I, I106L, and K107E (Kabat numbering) in the JL region of VL domain, and R108Q, R108D, R108I, T109P, T109R, T109D, V110K, V110E, A111K, A111E, A111L, A112R, A112E, A112Y, S114K, S114I, F116T, D122S, D122Y, E123R, E123L, Q124E, L125E, Q147A, Q147E, 0147K, K149D, V150A, D151K, N152S, N152L, A153H, L154E, Q155K, Q155E, S156A, S156R, N158R, N158D, S159K, S159E, S159L, D185I, V191R, E195K, E195K, S203L, K207T, S208T, N210E, G212E, and E213R (EU numbering) in light constant domain CL. FIG. 18 shows these residues mapped onto the light chain of the 1L71 Fab structure. Notably, the J segments and interfaces between both the VL/CL and VH/CH1 domains are involved in determining effector ligand binding. Equally important to residues at which mutation enhances binding are those at which mutation reduces or ablates binding; these results provide structure activity relationship (SAR) data that may be used to better understand the effector ligand binding determinants of the Fab region, and indicate that additional mutation at these positions may generate variants that provide enhanced effector ligand binding.

Figure 19:
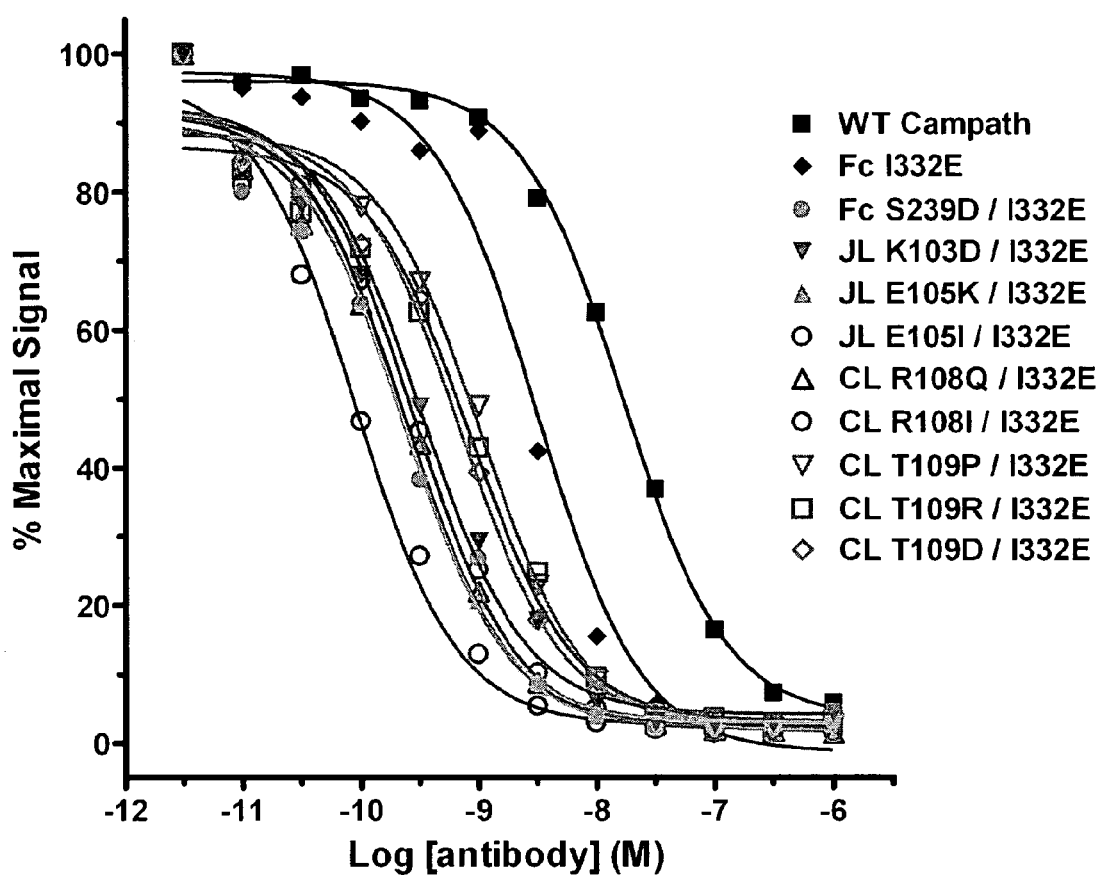
FIG. 19. Binding to human V158 FcγRIIIa by select J and constant region variant/Fc variant combinations, as determined by the AlphaScreen assay. Phosphate buffer saline (PBS) alone was used as the negative control. Fc variants I332E and S239D/I332E are also shown for direct comparison. Numbering is according to Kabat and EU numbering schemes as indicated in Table 4. The data were normalized to the maximum and minimum luminescence signal provided by the baselines at low and high concentrations of competitor antibody respectively. The curves represent the fits of the data to a one site competition model using nonlinear regression.

In an embodiment of the present invention, any of these Fab variants may be combined to potentially obtain further optimized effector ligand properties. In a preferred embodiment, any of the aforedescribed Fab variants is combined with one or variants in the Fc region, particularly Fc variants that provide optimized or altered effector function, with Fc variants described in U.S. Ser. No. 10/672,280, U.S. Ser. No. 10/822,231, U.S. Ser. No. 60/627,774, and U.S. Ser. No. 60/642,477 being most preferred. Select enhanced binding variants were combined with a previously described Fc variant, I332E, that also provides enhanced FcγR binding and effector function (U.S. Ser. No. 10/672,280). These Fab/Fc combination variants were constructed in the light and heavy chains of Campath in the pcDNA3.1Zeo vector using quick-change mutagenesis, expressed in 293T cells, and purified as described above. Binding affinity to human V158 FcγRIIIa, human F158 FcγRIIIa, and bacterial protein A were measured for the variants using the AlphaScreen assay as described above. FIG. 19 provides a representative data set from this series of binding assays, showing select Fab/Fc variant combinations that enhance FcγR binding. The Fold WT values provided by the fits to these data, generated as described above, are provided in Table 5. As can be seen, combination of some Fab variants with the Fc variant provides additive or synergistic effects. Again, as described above in Table 4, of particular importance are modifications that result in greater than 1-fold increase in affinity as compared to the wild-type (e.g. parent antibody) for any particular receptor. It is an aspect of the invention to provide modifications that provide higher affinity for at least one receptor.

TABLE 5

FCγR Binding Data for Fab/Fc Combination Variants

| Substitution(s) | Fold WT | | |
|---|---|---|---|
| | FcγRIIIa V158 | FcγRIIIa F158 | ProtA |
| Fc Region EU | | | |
| I332E | 8.07 | | 0.71 |
| S239D/I332E | 57.87 | | 0.81 |

TABLE 5-continued

FCγR Binding Data for Fab/Fc Combination Variants

| Substitution(s) | Fold WT FcγRIIIa V158 | Fold WT FcγRIIIa F158 | ProtA |
|---|---|---|---|
| JL Region/Fc Region Kabat | | | |
| Q100P/I332E | 11.36 | 17.33 | 0.84 |
| Q100G/I332E | 9.50 | 9.49 | 1.37 |
| Q100K/I332E | 18.18 | 29.55 | 0.65 |
| K103R/I332E | 13.78 | 17.82 | 0.91 |
| K103D/I332E | 47.23 | 56.91 | 2.01 |
| K103L/I332E | 9.95 | 14.12 | 1.43 |
| E105D/I332E | 24.68 | 31.61 | 1.20 |
| E105K/I332E | 59.29 | 93.12 | 4.39 |
| E105I/I332E | 171.02 | 326.98 | 4.36 |
| I106L/I332E | 23.61 | 15.94 | 0.97 |
| CL Region/Fc Region EU | | | |
| R108Q/I332E | 57.83 | 94.56 | 1.55 |
| R108D/I332E | 56.03 | 75.48 | 2.64 |
| R108I/I332E | 51.43 | 73.60 | 3.42 |
| T109P/I332E | 13.88 | 18.63 | 1.61 |
| T109R/I332E | 16.60 | 18.87 | 1.72 |
| T109D/I332E | 20.39 | 32.21 | 2.35 |
| V110K/I332E | 70.72 | 86.60 | 2.20 |
| A111K/I332E | 13.42 | 15.59 | 0.83 |
| A112R/I332E | 6.44 | 7.83 | 0.70 |
| A112E/I332E | 8.35 | 10.16 | 0.74 |
| A112Y/I332E | 16.55 | 30.45 | 1.27 |
| S114K/I332E | 7.14 | 12.54 | 0.88 |
| S114I/I332E | 5.99 | 6.04 | 0.81 |
| Q124E/I332E | 7.20 | 7.38 | 0.84 |
| L125E/I332E | 20.34 | 27.70 | 1.13 |
| Q147K/I332E | 8.47 | 4.80 | 1.11 |
| D151K/I332E | 40.43 | 82.93 | 4.73 |
| N152S/I332E | 19.17 | 14.51 | 1.95 |
| Q155K/I332E | 8.00 | 8.23 | 0.87 |
| S156A/I332E | 4.72 | 4.62 | 0.82 |
| N158R/I332E | 2.67 | | |
| N158D/I332E | 7.03 | 8.97 | 0.89 |
| S159K/I332E | 8.30 | 11.80 | 21.25 |
| S159E/I332E | 13.71 | 13.32 | 1.69 |
| D185I/I332E | 10.36 | 13.51 | 0.79 |
| V191R/I332E | 1.97 | | |
| K207L/I332E | 3.22 | | |
| S208T/I332E | 4.19 | | |
| N210E/I332E | 6.35 | | |
| G212E/I332E | 4.86 | | |
| E213R/I332E | 3.96 | | |

Together the results for variants comprising mutations in the JL, JH, CL, and CH1 regions serve as a set of structure activity relationship (SAR) data with which to better understand the impact of these regions on effector ligand binding. These data may be used to guide additional experiments for further investigate the impact of these regions on effector properties, as well as for further engineering to obtain optimal variants. The present invention contemplates additional substitutions at these positions, and at other positions that are proximal to these positions in three-dimensional space. For example, all residues with one or more atoms that are within 3 Å, 5 Å, or 10 Å of one or more atoms belonging to heavy chain residues T110I, S112D, S113D, S113R (Kabat numbering), or A118K, A118E, A118Y, S119E, T120E, K121H, G122E, N201E, and P206E (EU numbering) may be substituted with any or all of the 19 remaining amino acids. Additionally, Table 4 also shows a number of positions at which mutation causes a significant loss in binding affinity to FcγRIIIa, suggesting that said position may play a role in determining binding affinity or specifity between an antibody and FcγR. Accordingly, further substitutions at these positions are contemplated to obtain variants with enhanced effector ligand properties.

Example 4

Engineered Hinge Variants

The IgG hinge region is the flexible linker that genetically connects the IgG CH1 domain to the CH2 domain. For the purposes of the present invention, the hinge is defined according to a structural definition. The C-terminus of the CH2 domain is defined structurally by C220, which forms a disulfide bond with the C-terminal disulfide of the CL domain. The N-terminus of the CH2 domain is defined herein according to the last heavy chain residue before the ordered region of CH2. Available structures of the Fc region show electron density for residues G237 (pdb 1 DN2, DeLano et al., 2000, Science 287(5456):1279-83) and P237 (pdb 1FC2, Deisenhofer, 1981, Biochemistry 20(9):2361-70). Therefore for the purposes of the present invention, the IgG1 hinge is defined as heavy chain constant region residues D221-G236, with numbering according to the EU numbering scheme. It is noted that according to this definition, the hinge comprises part of the Fc region (typically defined from 226 or 230 to the C-terminus of the heavy chain constant region). Similar to the JL, JH, CL, and CH1 regions, the hinge region is typically conserved among antibodies of the same subclass. Thus residues within this region that play a role in determining effector ligand affinity/specificity and effector function properties may be more consistent from antibody to antibody, and accordingly variants that alter these properties may be more generally applicable to therapeutically useful antibodies. In order to characterize the effector determinants in the hinge region, and to generate variants that modulate effector ligand binding and effector function, a series of variants were designed to explore a large variety of substitutions at positions within the hinge. These variants are provided in Table 6. Positions are numbered according to the EU numbering scheme.

TABLE 6

Designed Hinge Variants

| Position | WT | Substitution(s) (EU numbering) |
|---|---|---|
| 221 | D | K Y E N Q R S T H A V L I F M W P G |
| 222 | K | E Y D N Q R S T H V L I F M W P G (A)* |
| 223 | T | D N Q R S H A V L I F M Y W P G E K |
| 224 | H | D N Q K R S T V L I F M W P G E Y (A)* |
| 225 | T | D N Q R S H A V L I F M Y P G E K W |
| 226 | C | S |
| 227 | P | E K Y G D N Q R S T H A V L I F M W |
| 228 | P | K Y G D N Q R T H A V L I F M W |
| 229 | C | S |
| 230 | P | A E Y G D N Q K R S T H V L I F M W |
| 231 | A | K P D N Q R S T H V L I F M W |
| 232 | P | E K Y G D N Q R S T H A V L I F M W |
| 233 | E | D N Q R S T H A V L I F M Y W G |
| 234 | L | D E N Q T H Y I V F K R S A M G |
| 235 | L | D S N Q T H Y I V F E K R A M W P G |
| 236 | G | D E N Q K R S T H A V L I F M Y W P |

*K222A and H224A were designed as a double mutant K222A/H224A in the context of Herceptin, not Campath These hinge variants were constructed in the light and heavy chains of Campath in the pcDNA3.1Zeo vector using quick-change mutagenesis, expressed in 293T cells, and purified as described above. Binding affinity to human V158

Figure 20A:
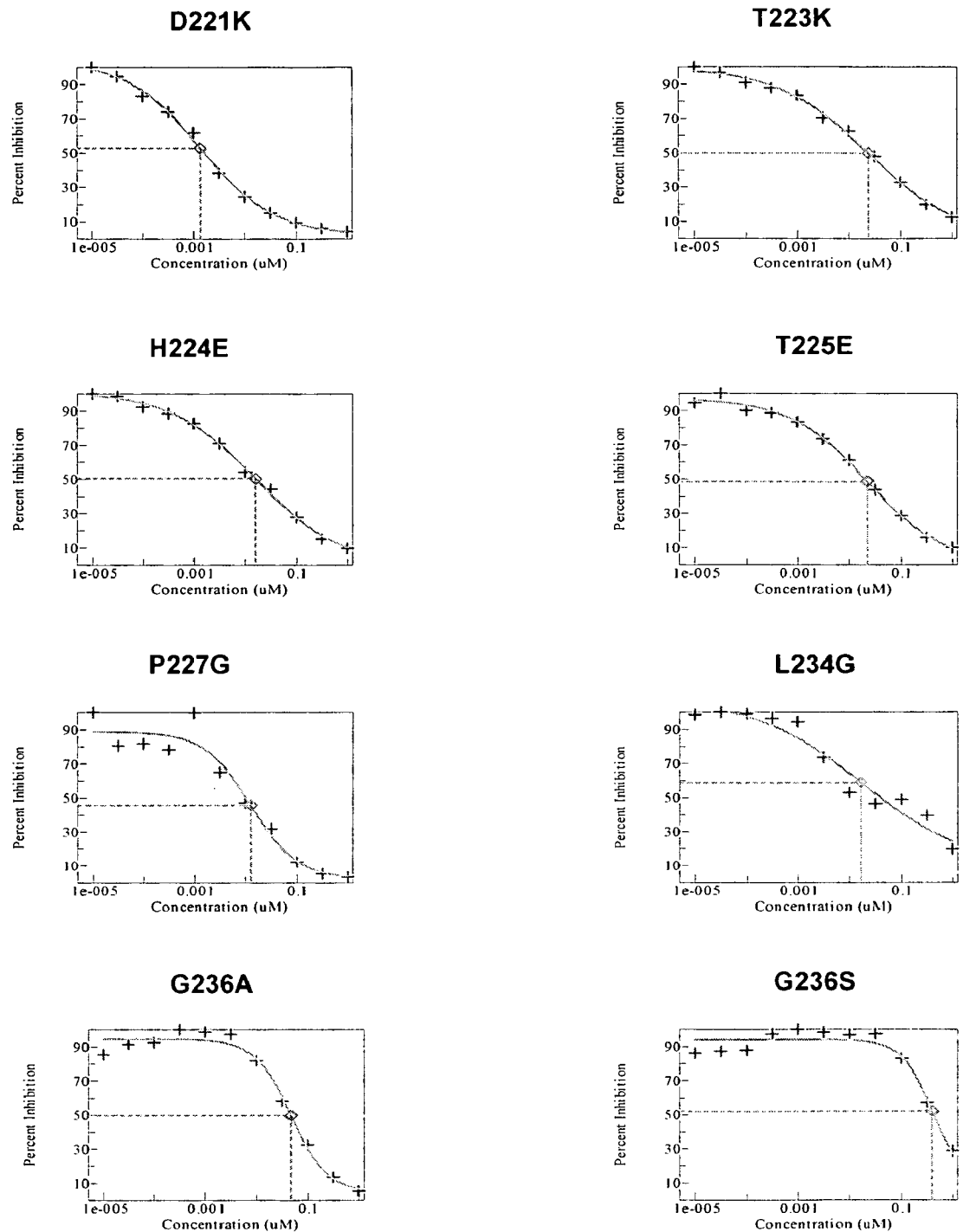
FIGS. 20a-20b. Binding to human effector ligands by select hinge variants as determined by the AlphaScreen assay.
Figure 20B:
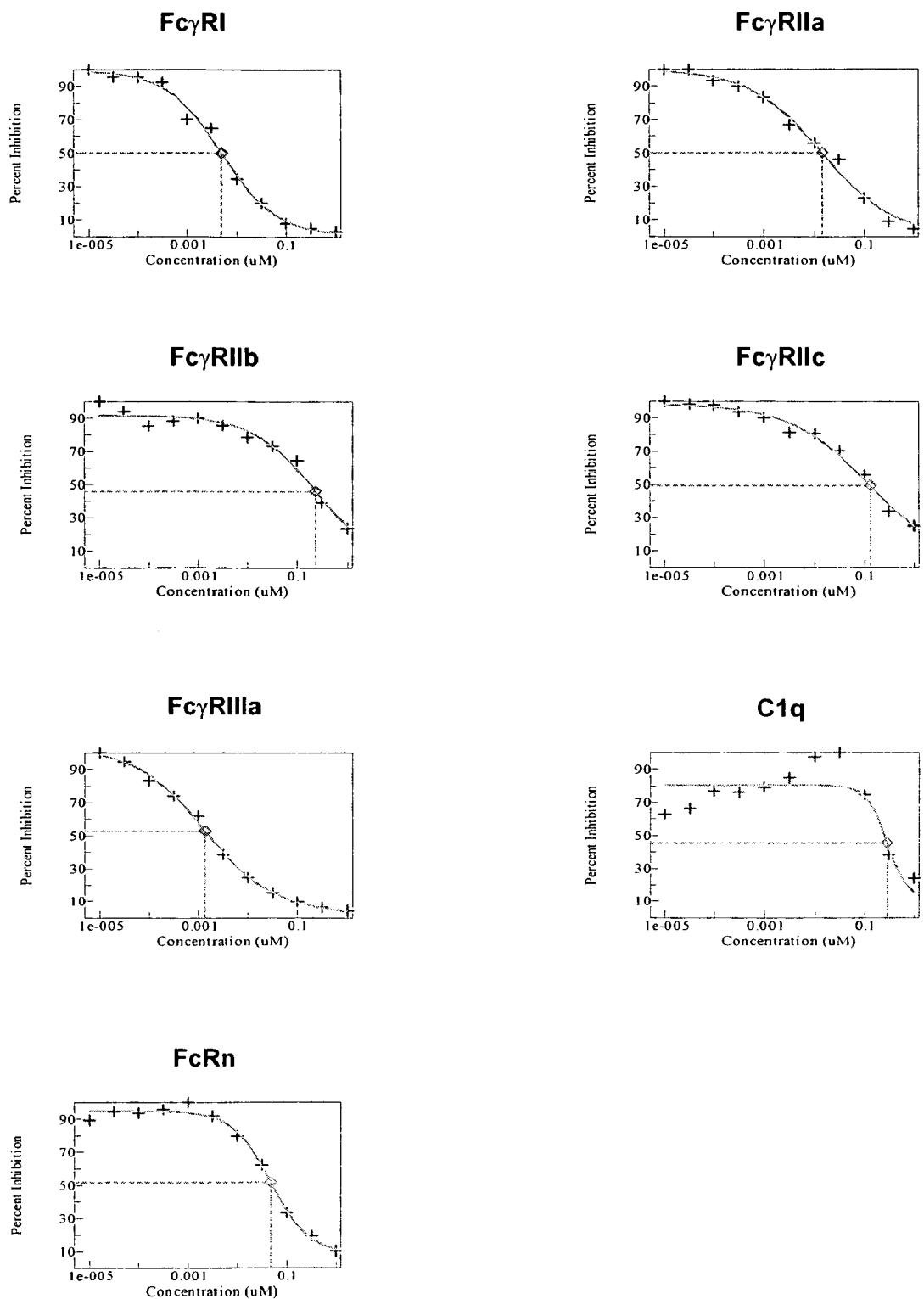

FcγRIIIa was measured using the AlphaScreen assay as described above. Some variants were also screened for binding to other effector ligands, including human FcγRI, FcγRIIa, FcγRIIb, FcγRIIc, FcRn, and C1q using the AlphaScreen; binding assays for these effector ligands were carried out similar to as described above for FcγRIIIa. FIG. 20a provides a representative set of raw data from this series of binding assays for select hinge variants that enhance FcγR binding. FIG. 20b shows the raw data from binding of the hinge variant D221K to full the spectrum of effector ligands tested. The Fold WT values provided by the fits to these data, generated as described provided in Table 6. Again, of particular importance are modifications that result in greater than 1-fold increase in affinity as compared to the wild-type (e.g. parent antibody) for any particular receptor. In some cases, as is true for the variants outlined in Tables 4 and 5 as well as Table 7, variants that provide higher affinity for at least one receptor, even if showing decreased affinity for a different receptor (all as compared to the parent antibody) are preferred embodiments. Similarly, variants that provide for higher affinity for more than one receptor are also desirable. It is an aspect of the invention to provide modifications that provide higher affinity for at least one receptor.

TABLE 7

Effector Ligand Binding Data for Hinge Variants

| Substitution(s) EU numbering | Fold WT | | | | | | |
|---|---|---|---|---|---|---|---|
| | FcγRIIIa V158 | FcγRI | FcγRIIa H131 | FcγRIIb | FcγRIIc | C1q | FcRn |
| D221K | 65.60 | 4.53 | 4.32 | 3.50 | 17.75 | 0.00 | 5.66 |
| D221Y | 0.56 | 2.43 | 2.62 | 2.41 | 10.01 | | 2.74 |
| D221E | 0.13 | | | | | | |
| D221N | | | | | | | |
| D221Q | 0.16 | | | | | | |
| D221R | | | | | | | |
| D221S | | | | | | | |
| D221T | | | | | | | |
| D221H | | | | | | | |
| D221A | | | | | | | |
| D221V | | | | | | | |
| D221L | | | | | | | |
| D221I | 0.24 | | | | | | |
| D221F | | | | | | | |
| D221M | | | | | | | |
| D221W | 0.84 | | | | | | |
| D221P | | | | | | | |
| D221G | | | | | | | |
| K222E | 1.51 | 1.77 | 1.26 | 1.04 | 1.22 | 1.23 | 0.64 |
| K222Y | 0.34 | 0.77 | 0.48 | 0.50 | 0.34 | 1.06 | 0.66 |
| K222D | | | | | | | |
| K222N | | | | | | | |
| K222Q | | | | | | | |
| K222R | 0.22 | | | | | | |
| K222S | 0.06 | | | | | | |
| K222T | 0.12 | | | | | | |
| K222H | | | | | | | |
| K222V | | | | | | | |
| K222L | | | | | | | |
| K222I | 0.87 | | | | | | |
| K222F | 0.32 | | | | | | |
| K222M | 0.44 | | | | | | |
| K222W | 0.12 | | | | | | |
| K222P | 0.14 | | | | | | |
| K222G | 0.12 | | | | | | |
| T223D | | | | | | | |
| T223N | 0.24 | | | | | | |
| T223Q | | | | | | | |
| T223R | 0.10 | | | | | | |
| T223S | 0.13 | | | | | | |
| T223H | | | | | | | |
| T223A | | | | | | | |
| T223V | | | | | | | |
| T223L | 0.17 | | | | | | |
| T223I | 0.23 | | | | | | |
| T223F | | | | | | | |
| T223M | 0.46 | | | | | | |
| T223Y | 0.19 | | | | | | |
| T223W | | | | | | | |
| T223P | 0.82 | | | | | | |
| T223G | | | | | | | |
| T223E | 0.75 | 2.12 | 2.37 | 1.74 | 3.70 | | 2.04 |
| T223K | 9.37 | 1.61 | 2.18 | | | 1.31 | 2.97 |
| H224D | 0.13 | | | | | | |
| H224N | 0.16 | | | | | | |
| H224Q | 0.32 | | | | | | |

TABLE 7-continued

Effector Ligand Binding Data for Hinge Variants

| | Fold WT | | | | | | |
|---|---|---|---|---|---|---|---|
| Substitution(s) EU numbering | FcγRIIIa V158 | FcγRI | FcγRIIa H131 | FcγRIIb | FcγRIIc | C1q | FcRn |
| H224K | 0.17 | | | | | | |
| H224R | | | | | | | |
| H224S | 0.39 | | | | | | |
| H224T | 0.50 | | | | | | |
| H224V | 0.87 | | | | | | |
| H224L | 0.95 | | | | | | |
| H224I | 0.48 | | | | | | |
| H224F | 0.69 | | | | | | |
| H224M | 0.39 | | | | | | |
| H224W | 0.91 | | | | | | |
| H224P | 0.57 | | | | | | |
| H224G | 1.27 | | | | | | |
| H224E | 14.28 | 1.91 | 3.67 | | | 2.80 | 5.11 |
| H224Y | 0.86 | 1.74 | 1.17 | | | 2.01 | 1.68 |
| T225D | 0.95 | | | | | | |
| T225N | 1.56 | | | | | | |
| T225Q | 0.77 | | | | | | |
| T225R | 1.93 | | | | | | |
| T225S | 0.60 | | | | | | |
| T225H | 1.19 | | | | | | |
| T225A | 0.96 | | | | | | |
| T225V | 2.09 | | | | | | |
| T225L | | | | | | | |
| T225I | | | | | | | |
| T225F | 1.10 | | | | | | |
| T225M | 0.29 | | | | | | |
| T225Y | 0.32 | | | | | | |
| T225P | 0.27 | | | | | | |
| T225G | | | | | | | |
| T225E | 9.84 | 2.28 | 2.75 | | | 1.96 | 4.89 |
| T225K | 0.22 | 0.30 | 0.37 | | | 1.12 | 5.68 |
| T225W | 0.59 | 2.30 | 1.04 | | | 1.92 | 6.89 |
| C226S | 0.37 | | | | | | |
| P227E | 2.10 | 1.47 | 1.55 | 1.55 | 1.67 | | 1.49 |
| P227K | 0.38 | 0.44 | 0.64 | | 3.04 | 0.92 | |
| P227Y | 0.44 | 1.06 | 0.89 | 0.79 | 0.73 | | 0.80 |
| P227G | 15.77 | 0.70 | 1.39 | | 6.56 | 0.59 | |
| P227D | | | | | | | |
| P227N | | | | | | | |
| P227Q | 0.81 | | | | | | |
| P227R | 0.60 | | | | | | |
| P227S | 0.47 | | | | | | |
| P227T | 0.30 | | | | | | |
| P227H | 0.33 | | | | | | |
| P227A | 0.31 | | | | | | |
| P227V | | | | | | | |
| P227L | 0.60 | | | | | | |
| P227I | 0.39 | | | | | | |
| P227F | 0.70 | | | | | | |
| P227M | 0.83 | | | | | | |
| P227W | | | | | | | |
| P228K | 1.28 | 1.91 | 1.31 | 1.14 | 1.13 | 1.62 | 1.55 |
| P228Y | 0.75 | 1.15 | 1.68 | 1.59 | 1.61 | 2.25 | 1.45 |
| P228G | 0.98 | 1.00 | 2.60 | 0.96 | 0.54 | 1.89 | 1.77 |
| P228D | | | | | | | |
| P228N | | | | | | | |
| P228Q | | | | | | | |
| P228R | | | | | | | |
| P228T | | | | | | | |
| P228H | | | | | | | |
| P228A | | | | | | | |
| P228V | | | | | | | |
| P228L | | | | | | | |
| P228I | | | | | | | |
| P228F | | | | | | | |
| P228M | | | | | | | |
| P228W | | | | | | | |
| C229S | | | | | | | |
| P230A | 0.55 | 1.28 | 0.99 | | | 2.53 | 0.77 |
| P230E | 1.40 | 2.07 | 1.25 | 2.34 | 1.47 | 2.70 | 1.01 |
| P230Y | 0.56 | 0.44 | 0.40 | 0.85 | 1.22 | 2.00 | 0.65 |
| P230G | 0.48 | 1.04 | 0.99 | 1.13 | 0.75 | 1.27 | 1.16 |

TABLE 7-continued

Effector Ligand Binding Data for Hinge Variants

| | Fold WT | | | | | | |
|---|---|---|---|---|---|---|---|
| Substitution(s) EU numbering | FcγRIIIa V158 | FcγRI | FcγRIIa H131 | FcγRIIb | FcγRIIc | C1q | FcRn |
| P230D | | | | | | | |
| P230N | | | | | | | |
| P230Q | | | | | | | |
| P230K | | | | | | | |
| P230R | | | | | | | |
| P230S | | | | | | | |
| P230T | | | | | | | |
| P230H | | | | | | | |
| P230V | | | | | | | |
| P230L | | | | | | | |
| P230I | | | | | | | |
| P230F | | | | | | | |
| P230M | | | | | | | |
| P230W | | | | | | | |
| A231K | 0.58 | 0.50 | 0.62 | 0.41 | 0.58 | 1.40 | 0.52 |
| A231P | 0.31 | 1.17 | | 0.81 | | | |
| A231D | | | | | | | |
| A231N | | | | | | | |
| A231Q | | | | | | | |
| A231R | | | | | | | |
| A231S | | | | | | | |
| A231T | | | | | | | |
| A231H | | | | | | | |
| A231V | | | | | | | |
| A231L | | | | | | | |
| A231I | | | | | | | |
| A231F | | | | | | | |
| A231M | | | | | | | |
| A231W | | | | | | | |
| P232E | 1.51 | 2.97 | 0.80 | 1.59 | 0.99 | 1.18 | 0.76 |
| P232K | 0.77 | 0.70 | 0.87 | 0.85 | 0.61 | 0.78 | 1.56 |
| P232Y | 0.99 | 1.91 | 1.51 | 1.49 | 0.96 | 0.87 | 0.68 |
| P232G | 0.04 | 0.10 | 0.05 | 0.11 | | 0.14 | 0.70 |
| P232D | | | | | | | |
| P232N | | | | | | | |
| P232Q | | | | | | | |
| P232R | | | | | | | |
| P232S | | | | | | | |
| P232T | | | | | | | |
| P232H | | | | | | | |
| P232A | | | | | | | |
| P232V | | | | | | | |
| P232L | | | | | | | |
| P232I | | | | | | | |
| P232F | | | | | | | |
| P232M | | | | | | | |
| P232W | | | | | | | |
| E233D | 0.64 | 0.85 | 0.81 | | | 2.66 | 0.76 |
| E233N | 0.48 | 0.16 | 0.50 | 0.34 | 0.46 | 1.28 | 0.74 |
| E233Q | 0.51 | 0.19 | 0.52 | 0.27 | 0.39 | 1.17 | 0.61 |
| E233R | 0.35 | 0.14 | 0.75 | 0.36 | 0.60 | 1.13 | 1.05 |
| E233S | 0.36 | 0.17 | 0.62 | 0.31 | 0.37 | 1.18 | 1.10 |
| E233T | 0.42 | 0.15 | 1.28 | 0.78 | 0.83 | 0.99 | 1.19 |
| E233H | 0.32 | 0.17 | 0.74 | 0.58 | 0.78 | 1.05 | 0.99 |
| E233A | 0.46 | 0.10 | 1.23 | 0.60 | 0.71 | 1.02 | 0.93 |
| E233V | 0.50 | 0.25 | 0.71 | 0.37 | 0.61 | 0.70 | 0.91 |
| E233L | 0.52 | 0.53 | 0.55 | 0.26 | 0.54 | 2.24 | 0.60 |
| E233I | 0.88 | 0.30 | 1.09 | 1.69 | 1.80 | 2.30 | 0.95 |
| E233F | 0.58 | 0.23 | 0.64 | 0.73 | 0.84 | 1.27 | 0.90 |
| E233M | 0.70 | 0.29 | 0.67 | 0.49 | 0.85 | 1.56 | 1.13 |
| E233Y | 0.37 | 0.31 | 0.96 | 0.97 | 0.55 | | 1.86 |
| E233W | 0.35 | 0.28 | 0.86 | 0.82 | 0.70 | 0.91 | 1.64 |
| E233G | 1.21 | 0.36 | 1.21 | 0.94 | 0.74 | 1.03 | 2.09 |
| L234D | 3.89 | 0.36 | 0.40 | 4.95 | | 0.96 | 1.54 |
| L234E | 1.86 | 0.42 | 0.24 | 4.78 | | 1.19 | 1.25 |
| L234N | 0.49 | 0.10 | 0.19 | 2.05 | | 1.18 | 1.06 |
| L234Q | 0.52 | 0.28 | 0.28 | 3.53 | | 0.94 | 0.97 |
| L234T | 0.26 | 0.49 | 0.20 | 1.79 | | 0.56 | 0.99 |
| L234H | 0.27 | 0.11 | 0.29 | 1.56 | | 0.65 | 1.48 |
| L234Y | 0.80 | 1.45 | 0.51 | 1.93 | | 0.99 | 1.90 |
| L234I | 1.30 | 1.20 | 0.78 | 2.57 | | 1.28 | 1.26 |
| L234V | 1.61 | 1.66 | 0.78 | 3.94 | | 0.64 | 1.45 |

TABLE 7-continued

Effector Ligand Binding Data for Hinge Variants

Fold WT

| Substitution(s) EU numbering | FcγRIIIa V158 | FcγRI | FcγRIIa H131 | FcγRIIb | FcγRIIc | C1q | FcRn |
|---|---|---|---|---|---|---|---|
| L234F | 0.37 | 0.74 | 0.47 | 2.36 |  | 0.72 | 1.46 |
| L234K | 0.53 | 0.43 | 0.65 | 1.42 | 1.09 | 2.02 | 0.62 |
| L234R | 0.73 | 0.38 | 0.87 | 1.49 | 1.52 | 1.72 | 1.19 |
| L234S | 0.69 | 0.49 | 1.01 | 1.40 | 1.30 |  | 0.93 |
| L234A | 0.35 | 0.44 | 0.80 | 0.85 | 0.62 | 0.88 | 0.58 |
| L234M | 0.49 | 0.64 | 0.89 | 0.90 | 0.65 | 0.88 | 0.55 |
| L234G | 2.17 | 0.70 | 3.26 | 3.62 | 3.48 | 1.91 | 2.54 |
| L235D | 1.61 |  | 0.76 | 5.48 |  | 1.05 | 0.90 |
| L235S | 0.95 |  | 0.27 | 2.99 |  | 0.66 | 1.51 |
| L235N | 0.37 | 0.06 | 0.21 | 1.59 |  | 0.70 | 1.32 |
| L235Q | 1.02 | 0.09 | 0.30 | 1.40 |  | 0.85 | 1.67 |
| L235T | 2.15 | 0.13 | 0.53 | 3.55 |  | 1.06 | 1.65 |
| L235H | 0.30 | 0.06 | 0.51 | 1.77 |  | 0.54 | 0.96 |
| L235Y | 1.74 | 0.24 | 3.32 | 4.44 |  | 0.86 | 1.02 |
| L235I | 1.47 | 0.16 | 0.67 | 1.24 |  | 0.68 | 0.81 |
| L235V | 0.58 | 0.16 | 0.43 |  |  | 0.94 | 1.31 |
| L235F | 0.56 |  | 1.25 | 1.62 |  | 0.71 | 0.80 |
| L235E | 1.06 | 0.34 | 0.63 | 0.83 | 0.80 | 0.93 | 0.78 |
| L235K | 0.63 | 0.42 | 0.56 | 1.28 | 1.34 | 1.55 | 0.96 |
| L235R | 0.62 | 0.35 | 0.71 | 1.93 | 1.15 | 1.73 | 0.53 |
| L235A | 0.41 | 0.34 | 0.62 | 0.84 | 0.78 | 1.00 | 0.97 |
| L235M | 0.46 | 0.38 | 0.79 | 0.89 | 0.64 | 1.05 | 0.69 |
| L235W | 0.32 | 0.11 | 0.90 | 0.77 | 0.50 | 0.83 | 0.46 |
| L235P | 0.78 | 0.13 | 1.16 | 1.16 | 0.89 | 1.31 | 0.86 |
| L235G | 0.43 |  | 0.99 | 1.02 | 0.74 | 1.12 | 0.68 |
| G236D | 0.11 | 0.15 | 5.01 | 3.77 | 4.74 | 1.64 | 1.53 |
| G236E | 1.41 | 0.06 | 4.88 |  | 3.39 | 0.48 |  |
| G236N | 0.07 | 0.07 | 0.26 | 0.69 | 0.79 |  | 1.89 |
| G236Q | 0.17 | 0.12 | 0.60 |  | 0.26 | 1.89 | 1.46 |
| G236K | 0.46 | 0.11 |  |  | 0.55 | 2.18 | 1.38 |
| G236R | 0.10 | 0.10 | 0.31 |  | 0.19 | 2.03 | 1.99 |
| G236S | 5.77 | 0.55 | 22.71 | 2.77 | 3.68 | 1.82 | 1.77 |
| G236T | 0.11 | 0.11 | 1.89 | 0.95 | 0.48 | 3.25 | 1.56 |
| G236H | 0.08 | 0.03 | 0.37 | 0.31 | 0.21 |  | 0.52 |
| G236A | 0.65 | 0.48 | 44.99 | 1.05 | 1.45 | 1.64 | 1.75 |
| G236V | 0.27 | 0.14 | 1.52 | 0.82 | 0.47 | 1.59 | 1.35 |
| G236L | 0.18 | 0.04 |  | 1.07 |  |  |  |
| G236I | 0.02 | 0.11 | 1.33 |  | 0.12 | 1.96 | 1.33 |
| G236F | 0.18 | 0.06 | 0.43 |  | 0.88 | 1.19 |  |
| G236M | 0.19 | 0.14 | 0.34 | 0.79 | 0.40 | 1.40 | 1.60 |
| G236Y | 0.14 | 0.17 | 0.78 |  |  | 1.34 | 1.52 |
| G236W | 0.29 | 0.78 | 2.13 | 0.70 | 0.29 | 1.40 | 1.52 |
| G236P | 0.10 | 0.15 | 0.11 | 0.24 | 0.15 | 1.38 | 1.41 |
| K222A/H224A* | 0.67* |  |  |  |  |  |  |

*The K222A/H224A double variant was constructed in the context of Herceptin, and its Fold WT FcγRIIIa binding was determined by SPR, not AlphaScreen.

The data show that some hinge variants provide selective binding of the antibody to the different effector ligands, in some cases with substantial enhancements in affinity. In one embodiment, variants that bind an effector ligand with greater than 1-fold affinity relative to WT may be considered as providing improved or enhanced binding. In a preferred embodiment, variants that bind with greater than 2-fold affinity may be considered. In a particularly preferred embodiment, variants that bind an effector ligand with greater than 3-fold affinity relative to WT may be considered as providing enhanced binding. In an embodiment of the present invention, any of these hinge variants may be combined to potentially obtain further optimized effector ligand properties. Likewise, similar to as shown above with the Fab variants, in a preferred embodiment any of the aforedescribed hinge variants may be combined with one or variants in the Fc region, particularly Fc variants that provide optimized or altered effector function, with Fc variants described in U.S. Ser. No. 10/672,280, U.S. Ser. No. 10/822,231, U.S. Ser. No. 60/627,774, and U.S. Ser. No. 60/642,477 being most preferred.

Whereas particular embodiments of the invention have been described above for purposes of illustration, it will be appreciated by those skilled in the art that numerous variations of the details may be made without departing from the invention as described in the appended claims. All references are herein expressly incorporated by reference.

We claim:

1. An antibody variant comprising at least one amino acid modification in the light chain, said modification selected from the group consisting of R108Q, R108D, R108I, T109P, T109R, and T109D, wherein said antibody variant has increased affinity for FcγRIIIa as compared to the parent antibody, and wherein the number is according to the EU numbering scheme.

* * * * *